(12) United States Patent
Brioschi et al.

(10) Patent No.: US 10,039,843 B2
(45) Date of Patent: Aug. 7, 2018

(54) PARAMAGNETIC SOLID LIPID NANOPARTICLES (PSLNS) CONTAINING METAL AMPHIPHILIC COMPLEXES FOR MRI

(71) Applicant: BRACCO IMAGING S.P.A., Milan (IT)

(72) Inventors: Chiara Brioschi, Varedo (IT); Claudia Cabella, Pecco (IT); Simona Ghiani, Almese (DK); Alessandro Maiocchi, Monza (IT); Luigi Miragoli, Dovera (IT); Massimo Visigalli, Settala (IT)

(73) Assignee: BRACCO IMAGING S.P.A., Milan (IT)

( * ) Notice: Subject to any disclaimer, the term of this patent is extended or adjusted under 35 U.S.C. 154(b) by 416 days.

(21) Appl. No.: 14/426,036

(22) PCT Filed: Sep. 6, 2013

(86) PCT No.: PCT/EP2013/068463
§ 371 (c)(1),
(2) Date: Mar. 4, 2015

(87) PCT Pub. No.: WO2014/037498
PCT Pub. Date: Mar. 13, 2014

(65) Prior Publication Data
US 2015/0258221 A1  Sep. 17, 2015

(30) Foreign Application Priority Data

Sep. 7, 2012  (IT) .............................. MI2012A1492

(51) Int. Cl.
*A61B 5/055* (2006.01)
*A61K 49/10* (2006.01)
*A61K 49/18* (2006.01)
*A61K 49/08* (2006.01)

(52) U.S. Cl.
CPC .......... *A61K 49/106* (2013.01); *A61K 49/085* (2013.01); *A61K 49/1881* (2013.01); *A61K 49/101* (2013.01)

(58) Field of Classification Search
None
See application file for complete search history.

(56) References Cited

U.S. PATENT DOCUMENTS

| | | |
|---|---|---|
| 6,342,598 B1 | 1/2002 | Anelli et al. |
| 2006/0018830 A1 | 1/2006 | Cappelletti et al. |
| 2007/0243136 A1 | 10/2007 | Fisher et al. |
| 2012/0294809 A1* | 11/2012 | Walters ................ A61K 49/106 424/9.322 |
| 2013/0309176 A1 | 11/2013 | Port et al. |
| 2014/0348755 A1* | 11/2014 | Weng ........................ B82Y 5/00 424/9.32 |

FOREIGN PATENT DOCUMENTS

| | | |
|---|---|---|
| EP | 0526666 A1 | 2/1993 |
| EP | 1803711 A1 | 7/2007 |
| EP | 2535326 A1 | 12/2012 |
| EP | 2639227 A1 | 9/2013 |
| FR | 2968999 A1 | 6/2012 |
| WO | 1997-000087 A1 | 1/1997 |
| WO | 2000-009170 A1 | 2/2000 |
| WO | 2000-030620 A1 | 6/2000 |
| WO | 2000-030688 A2 | 6/2000 |
| WO | 2004-039351 A2 | 5/2004 |
| WO | 2006002873 A2 | 1/2006 |
| WO | 2006-100305 A2 | 9/2006 |
| WO | 2006-136564 A1 | 12/2006 |
| WO | 2011-044545 A2 | 4/2011 |

OTHER PUBLICATIONS

Hak et al. (Eur. J. Pharm. Biopharm. 2009, 72, 397-404).*
Zhu et al. (J. Nanosci. Nanobiotech. 2006, 6, 996-1003).*
Office Action for Chinese application No. 201380046466.9, dated Aug. 19, 2016 (English translation) [B0666].
Jung, S.H. et al., "Gd(III)-DOTA-modified sonosensitive liposomes for ultrasound-triggered release and MR imaging," Nanoscale Res. Lett., 2012, 7(1):462.
Office Action for Japanese application No. 2015-530409, dated Apr. 4, 2017 (English translation) [B0666].
Ahlin, Pegi et al., "Optimization of procedure parameters and physical stability of solid lipid nanoparticles in dispersions", ACTA Pharmaceutica, 1998, No. 48, pp. 259-267, XP002901401, ISSN: 1330-0075.
Aime, Silvio et al., "[Gd-AAZTA]—: A New Structural Entry for an Improved Generation of M RI Contrast Agents", Inorganic Chemistry, 2004, vol. 43, No. 24, pp. 7588-7590, American Chemical Society.
Anelli, Pier Lucio et al., "Mixed micelles containing lipophilic gadolinium complexes as MRA contrast agents", MAGMA: Magnetic Resonance Materials in Physics, Biology and Medicine, 2001, vol. 12, pp. 114-120, Elsevier Science B.V.

(Continued)

*Primary Examiner* — Michael G Hartley
*Assistant Examiner* — Melissa J Perreira
(74) *Attorney, Agent, or Firm* — Vivicar Law, PLLC

(57) ABSTRACT

The present invention relates to paramagnetic solid lipid nanoparticles (pSLNs) comprising an amphiphilic paramagnetic metal chelating moiety selected from: a diazepine derivative of Formula I and a tetraazocyclododecane derivative of Formula (II): being said chelating moiety complexed to a paramagnetic metal ion selected from the group consisting of: Gd(III), Mn(II), Cr(III), Cu(II), Fe(III), Pr(III), Nd(III), Sm(III), Tb(III), Yb(III), Dy(III), Ho(III) and Er(III), or salts thereof. The invention further relates to the process for preparation of said solid lipid nanoparticles comprising amphiphilic complexes of paramagnetic metals (pSLNs) and to the use of pSLNs as MRI contrast agents in the diagnostic field.

26 Claims, 6 Drawing Sheets

(56) References Cited

OTHER PUBLICATIONS

Briley-Saebo, Karen C. et al., "Gadolinium Mixed-Micelles: Effect of the Amphiphile on in Vitro and in Vivo Efficacy in Apolipoprotein E Knockout Mouse Models of Atherosclerosis", Magnetic Resonance in Medicine, 2006, vol. 56, No. 6, pp. 1336-1346, XP055062964, ISSN: 0740-3194, DOI: 10.1002/mrm.21094, Wiley-Liss, Inc.

Briley-Saebo, Karen C. et al., "High relaxivity gadolinium modified high density lipoproteins as MRI contrast agents", The Journal Physical Chemistry B., 2009, vol. 113, No. 18, pp. 6283-6289, XP055062914, ISSN: 1520-6106, DOI: 10.1021/jp8108286, NIH Public Access, Author Manuscript.

Chapman, D., "The Polymorphism of Glycerides", Chem. Review, 1962, pp. 433-456, University Chemical Laboratory, Cambridge, England.

Feshitan, Jameel A. et al., "Theranostic Gd(III)-lipid microbubbles for MRI-guided focused ultrasound surgery", Biomaterials, 2012, vol. 33, No. 1, pp. 247-255, XP028333975, ISSN: 0142-9612, DOI: 10.1016/J.Biomaterials.2011.09.026, Elsevier Ltd.

Gianolio, Eliana et al., "A Novel Method of Cellular Labeling: Anchoring MR-Imaging Reporter Particles on the Outer Cell Surface", ChemMedChem, 2008, vol. 3, No. 1, pp. 60-62, XP055099329, ISSN: 1860-7179, DOI: 10.1002/cmdc.200700182, www.chemmedchem.org, Wiley-VCH Verlag GmbH & Co. KGaA, Weinheim.

Greene, Theodora W., "Protective Groups in Organic Synthesis", 1st Edition, Chapter 5, 1981, pp. 152-178, John Wiley & Sons, Inc.

Kielar, Filip et al., "Large Relaxivity Enhancement of Paramagnetic Lipid Nanoparticles by Restricting the Local Motions of the GdIII Chelates", Journal of the American Chemical Society, 2010, vol. 132, No. 23, pp. 7836-7837, XP055062913, ISSN: 0002-7863, DOI: 10.1021/ja101518v.

Kristl, J. et al., "Interactions of solid lipid nanoparticles with model membranes and leukocytes studied by EPR", International Journal of Pharmaceutics, 2003, vol. 256, No. 1-2, pp. 133-140, XP055063186, ISSN: 0378-5173, DOI: 10.1016/S0378-5173(03)00070-X, Elsevier Science B.V.

Levy, Stuart G. et al., "Development of a Multigram Asymmetric Synthesis of 2-(R)-2-(4,7,10-Tristert-Butylcarboxymethyl-1,4,7,10-tetraazacyclododec-1-yl)-pentanedioic Acid, 1-tert-Butyl Ester, (R)-tert-Bu4-DOTAGA1", Organic Process Research & Development., 2009, vol. 13, No. 3, pp. 535-542.

Longmire, Michelle et al., "Clearance Properties of Nano-sized Particles and Molecules as Imaging Agents: Considerations and Caveats", Nanomedicine, 2008, vol. 3, No. 5, pp. 703-717, doi:10.2217/17435889.3.5.703, NIH Public Acess, Author Manuscript.

Morel, Silvia et al., "NMR relaxometric investigations of solid lipid nanoparticles (SLN) containing gadolinium(III) complexes", European Journal of Pharmaceutics and Biopharmaceutics, 1998, vol. 45, No. 2, pp. 157-163, XP004256965, ISSN: 0939-6411, DOI: 10.1016/S0939-6411(97)00107-0, Elsevier.

Mukherjee, S. et al., "Solid lipid nanoparticles: A modern formulation approach in drug delivery system", Indian Journal of Pharmaceutical Sciences, 2009, vol. 71, No. 4, pp. 349-358, doi:10.4103/0250-474X.57282.

Mulder, Willem J. et al., "Lipid-based nanoparticles for contrast-enhanced MRI and molecular imaging", NMR in Biomedicine, 2006, vol. 19, pp. 142-164, Wiley InterScience, DOI:10.1002/nbm.1011.

Terreno, Enzo et al., "Paramagnetic Liposomes as Innovative Contrast Agents for Magnetic Resonance (MR) Molecular Imaging Applications", Chemistry & Biodiversity, 2008, vol. 5, pp. 1901-912, Verlag Helvetica Chimica Acta AG, Zurich.

Windbergs, Maike et al., "Investigating the Principles of Recrystallization from Glyceride Melts", AAPS PharmSciTech, 2009, vol. 10, No. 4, pp. 1224-1233, DOI:10.1208/s12249-009-9311-5, American Association of Pharmaceutical Scientists.

Winter, Patrick M. et al., "Improved Molecular Imaging Contrast Agent for Detection of Human Thrombus", Magnetic Resonance in Medicine, 2003, vol. 50, No. 2, pp. 411-416, XP055041703, ISSN: 0740-3194, DOI: 10.1002/mrm.10532, Wiley-Liss, Inc.

Yamakoshi, Yoko et al., "LDL-based nanoparticles for contrast enhanced MRI of atheroplaques in mouse models", Chemical Communications, 2011, vol. 47, No. 31, p. 8835-8837, XP055062912, ISSN: 1359-7345, DOI: 10.1039/c1cc10924c, www.rsc.org/chemcomm, The Royal Society of Chemistry.

PCT International Search Report and Written Opinion for PCT/EP2013/068463, dated May 27, 2014 [B0666 WO].

Office Action for Chinese application No. 201380046466.9, dated Dec. 5, 2017 (English translation) [B0666].

Office Action for Chinese application No. 201380046466.9, dated May 9, 2017 (English translation) [B0666].

\* cited by examiner

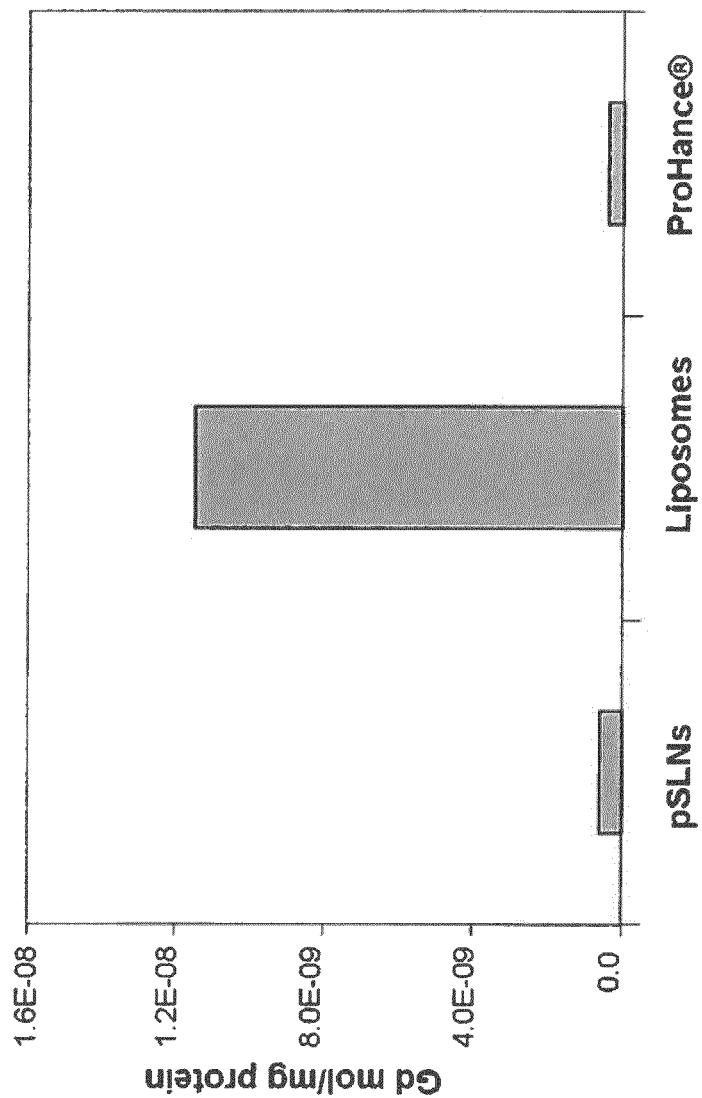

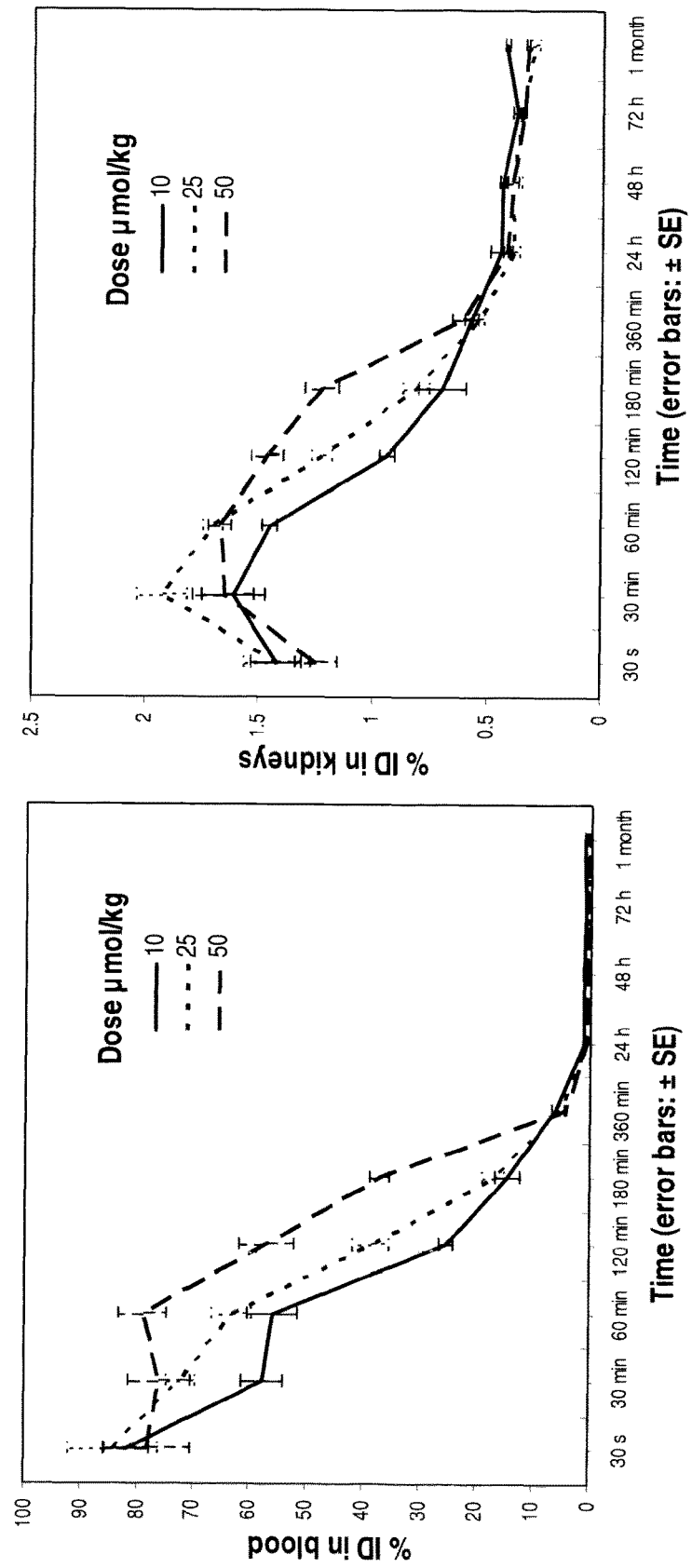
Figure 5 Panel (A)

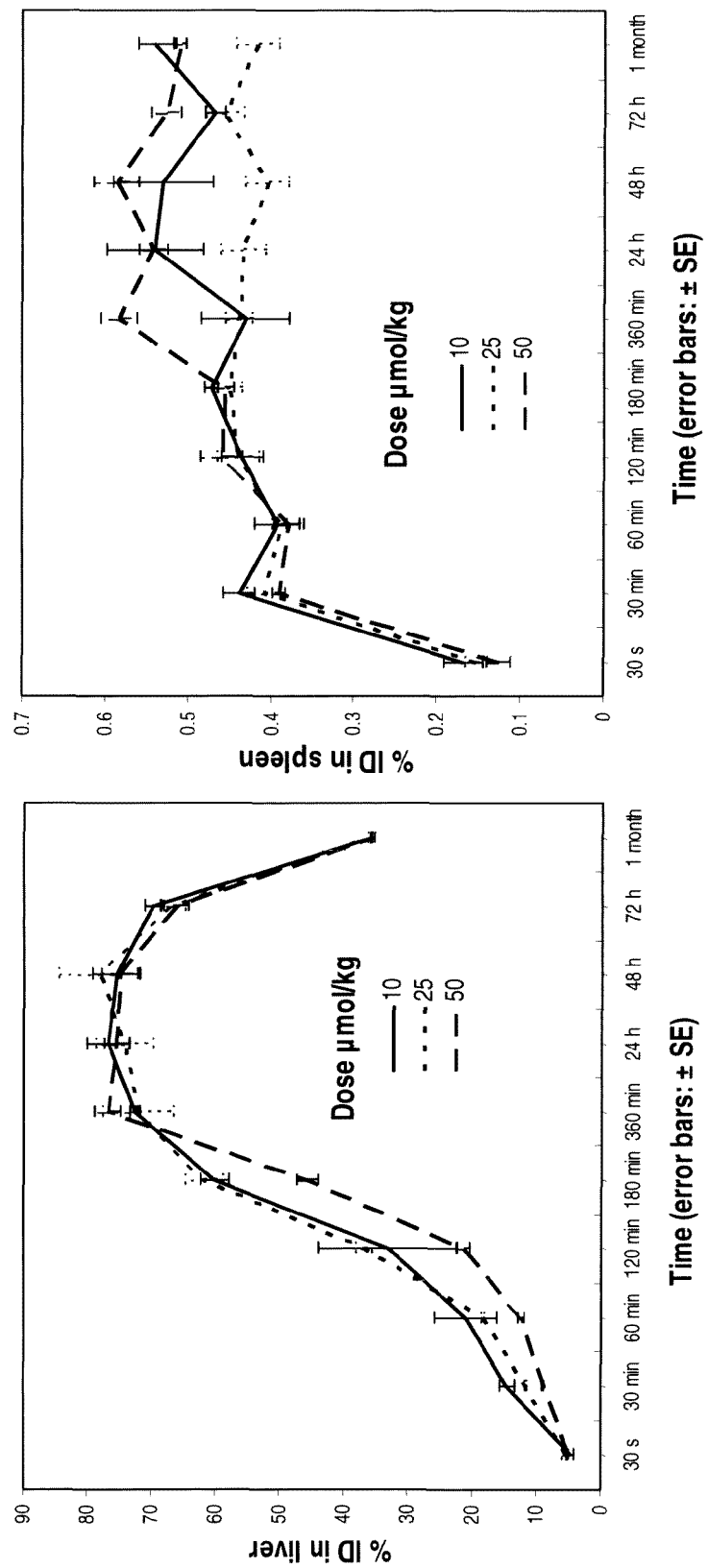
Figure 5 Panel (B)

PARAMAGNETIC SOLID LIPID NANOPARTICLES (PSLNS) CONTAINING METAL AMPHIPHILIC COMPLEXES FOR MRI

CROSS-REFERENCE TO RELATED APPLICATIONS

This application is the national stage application of corresponding international application number PCT/EP2013/068463, filed Sep. 6, 2013, which claims priority to and the benefit of Italian application no. MI2012A001492, filed Sep. 7, 2012, all of which are hereby incorporated by reference in their entirety.

FIELD OF THE INVENTION

The present invention relates to a novel process for the preparation of Solid Lipid Nanoparticles (SLNs) with paramagnetic properties (pSLNs) containing derivatives of paramagnetic metal ions chelating agents such as tetraazacyclododecanes and diazepine-derivatives for use as contrast agents in MRI (Magnetic Resonance Imaging).

STATE OF THE ART

Contrast agents commonly used in the clinical setting are low molecular weight hydrophilic gadolinium complexes which, after intravenous administration, are differentially distributed in the extracellular space, depending on differential vessel permeability in pathological tissues compared to healthy tissues. The different concentration reached in tissues, depending on the extent of extravasation, leads to different intensity of the magnetic resonance signal, which results in an increased positive contrast (white) in the image. The inherent ability of a contrast agent to generate a measurable signal by magnetic resonance imaging is due to a parameter termed relaxivity (r) which indicates the ability of the contrast agent to modify relaxation times of the magnetization vector of water protons.

There are two types of relaxation mechanisms referred to as "longitudinal" and "transverse" each with its own relaxivity parameter $r_1$ and $r_2$, respectively. The relaxivity parameter generally used to compare the effectiveness of a contrast agent in a clinical setting is normally $r_1$. The products currently used in the clinical setting have $r_1$ values in the range comprised between 4-6 $mM^{-1}s^{-1}$ when they are measured at 25° C. in water with an external magnetic field of 0.47 T. A second important feature of this class of products is the total absence of specific interactions with biomolecules except, in some cases, a weak interaction with serum albumin. As a result, blood clearance rates are high and elimination mainly occurs by glomerular filtration, i.e. via urine. It follows that this class of products is characterized by lack of specificity for bloodstream, tissues and cellular or molecular components. In recent years, the search for alternative MRI contrast agents has increasingly developed. The research for new contrast agents has been directed toward the development of technological platforms based on nanoparticles which provide a higher specificity for pathological tissues, due to their efficient accumulation and retention at the target site (EPR effect) and longer half-lives in the bloodstream. The commonly used scheme involves incorporation of numerous gadolinium complexes (1000-100000) in a nanoparticle (liposomes, mixed micelles, nanoemulsions, dendrimers, etc.).

In this regard, the use of chelating agents modified with >10 carbon atoms alkyl chains (medium-long alkyl chain) providing lipophilic properties to the chelating unit aimed at favouring their incorporation into lipid based particulate systems (i.e. emulsions, micelles, liposomes etc.) has already been described in the art.

In particular WO 00/09170 by the same Applicant describes the preparation of a micellar dual MRI contrast agent, comprising both a prevalently vascular MRI complex and a prevalently extravascular one. The preparation of the paramagnetic chelating agents with lipophilic moiety, described in WO97/00087, is used in WO00/09170 in association with one or more amphipatic organic compounds. Furthermore, the preparation of [10-[2-(Octadecylamino)-2-oxoethyl]-1,4,7,10-tetraaza-cyclododecane-1,4,7-triacetato-(3-)]gadolinium] is described.

Briley-Saebo, J Phys Chem, 2009, describes the conjugation of respectively alkyl and phospholipid derivatized AAZTA and DTPA Gd chelating agents to High Density Lipoproteins (HDL) for the preparation of MR labelled lipoproteins. On its turn, Yamakoshi et al. Chem. Comm. 2011, describes the conjugation of Gd DO3A-alkenyl chains with Low Density Lipoprotein (LDL) particles for MRI enhanced atheroplaques imaging.

U.S. Pat. No. 6,342,598 by the same Applicant, describes the preparation of polycarboxylic and macrocyclic chelating agents, modified via a carboxamido bond with a medium-long alkyl chain for the preparations of compositions that may form micellar compositions.

Kielar et al., JACS 2010 provides relaxivity measurements of liposomes prepared with DOTA complexes functionalized with two hydrophobic chains. Liposome relaxivity is greatly enhanced, confirming that supramolecular organization represents an attractive strategy for the development of high-relaxivity systems.

Furthermore, macromolecular systems offer a significantly flexible design, as it becomes possible to improve and modulate the properties of the particles produced by addition of specific molecular moieties for the recognition of receptor sites over-expressed in pathological tissues, or stealth agents which may limit recognition and consequent elimination/inactivation by reticulo-endothelial (RES) or immune systems. These properties together with the possibility to load the particles with a large number of imaging probes, allow to improve the sensitivity of the various imaging modalities, particularly those having a lower sensitivity such as magnetic resonance imaging. The use of paramagnetic nanoparticles makes magnetic resonance a valuable alternative to diagnostic techniques with radioactive probes typically used in molecular imaging procedures, providing the additional advantage of a better spatial resolution. Theoretically it is possible to make nanoparticles with high relaxivity values $(r_1)$ which are characterized by a satisfactory persistence in the bloodstream and are capable of recognizing molecular biomarkers, if appropriately modified.

In addition, the use of nanoparticles makes possible to design dual systems in which imaging probes with different properties can coexist to generate contrast agents usable for combined procedures, such as magnetic resonance imaging and positron emission tomography (PET/MRI) or X-ray computed tomography and single photon emission computed tomography (SPECT/CT).

However, nanoparticles (i.e. liposomes, quantum dots or iron oxide particles) have the disadvantage to accumulate not only in the sites of interest but also in the phagocytic cells of the reticuloendothelial system (especially Kupffer cells and macrophages) and for a long time.

Regardless of the strategies used for masking the particles from recognition by reticuloendothelial system, the result is usually a high accumulation of nanoparticles containing gadolinium in organs such as liver and spleen although with variable clearance times. Elimination from these organs is extremely slow resulting in increased exposure time of the human body to gadolinium, a substantially toxic ion (Longmire et al., Nanomedicine, 2008, 3: 703-717).

Therefore for nanoparticulate MRI agents, the challenge for an in vivo use is on one side the achievement of an optimal organ biodistribution and on the other a reduced toxicity due to Gd(III) accumulation. These properties have to combine with the ability of the nanoparticles to carry a high payload of imaging reporter, enabling a significant MR signal amplification, and thus, possibly reducing the dose of the paramagnetic metal administered.

Toxicity induced by increased exposure to gadolinium has been recently studied and a correlation between the onset of diseases such as the nephrogenic systemic fibrosis (NSF), also known as nephrogenic fibrosis dermopathy, and the administration of gadolinium complexes in patients with severe renal failure, found. This form of fibrosis leads to progressive and debilitating subcutaneous and muscular rigidity, associated with diffuse pain, which may lead to patient's death. The evidence of potential toxicity of contrast agents based on gadolinium complexes, due to their persistence in the human body, poses a major limitation to the possibility of developing applications using nanoparticles containing the aforementioned ion, even when it is in a chelated form. In addition, nanoparticles, as well as liposomes are not stable over time and are prepared with lipid components that may be considered unsafe for clinical use (Mukherje S. et al. Indian J Pharm Sci. 2009 July-August, 71(4): 349-358; doi: 10.4103/0250-474X.57282 e). In an attempt to identify safer and more flexible formulations of contrast agents, Morel (Morel S et al. Eur J Pharm Biopharm. 1998 March; 45 (2):157-63), for example, described the preparation of Solid Lipid Nanoparticles (pSLNs) containing gadolinium chelates complexes such as [GdDOTA]$^-$ and [GdDTPA]$^{2-}$, to explore the feasibility of this approach. However incorporation of the aforementioned gadolinium complexes into pSLNs is rather low.

The preparation of pSLNs described in Morel, exploiting methods originally described by Gasco (EP526666) which were primarily developed for the delivery of drugs or for their controlled release (WO 00/30 620) or to allow the delivery via particular administration routes (e.g. ocular route for the treatment of ophthalmic pathologies, such as in WO 2004/039 351) suffers from the low affinity of the hydrophilic Gd(III) complexes for the lipid core which results in a low SLN upload of Gd(III). Furthermore, the relaxation properties of such nanoparticles do not increase as expected, as confirmed by the relaxivity values for the pSLNs which are very close to those measured for the Gd complexes in solution (Kielar et al. J Am Chem Soc, 2010, cited; Mulder et al., NMR in Biomed, 2006, 19:142-164).

Therefore, is highly felt in the MR imaging field, the need to develop new strategies for the preparation of stable MR responsive nanoparticulate agents, solving the above mentioned problems.

The present approach for preparing SLNs with paramagnetic metal complexes, amphiphilic chelating agents specifically selected and designed as disclosed, overcome the above main limitations related to the preparation of Solid Lipid Nanoparticles as MRI agents (pSLNs).

In fact, the nanoparticles prepared according to the invention show a high Gd(III) payload and a good accessibility of the paramagnetic metal ions to the bulk water molecules, due to their orientation induced by the solid lipid core, resulting in a high nanoparticle relaxivity. Thus, lower doses of the paramagnetic metal for the achievement of the same image quality in their clinical use can be foreseen.

Furthermore, accumulation of Gd(III) in organs such as liver, spleen and kidney is limited and they show an optimal clearance time from these organs as observed by the present in vivo studies.

It is known, that nanoparticulate systems tend to accumulate in liver and spleen (Longmire et al. Nanomedicine, 2008, 3: 703-717) where the issue of Gd(III) toxicity becomes more relevant and highly limiting for the further development of these systems as MRI agents.

The pSLNs of the present invention have solved the above indicated problems: in vivo studies have shown that a limited accumulation of gadolinium in the reticulo-endothelial system in the medium/long term can be obtained by modulating the properties of the lipophilic chains of the metal chelating moiety and maintaining the relaxivity enhancement of these systems.

Thus, a higher safety compared to the various nanoparticle systems proposed in the art can be reasonably predicted.

SUMMARY OF THE INVENTION

The present invention relates to a paramagnetic solid lipid nanoparticle (pSLN) comprising an amphiphilic paramagnetic metal chelating moiety selected from: a diazepine derivative of Formula I and a tetraazocyclododecane derivative of Formula II:

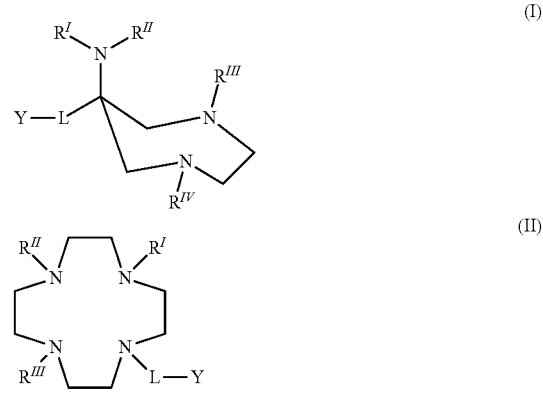

or salts thereof wherein:
Y is a group of formula Y'—NH— or (Y')$_2$—N—, where Y' is selected in the group consisting of: a linear or branched saturated or insaturated $C_8$-$C_{16}$ alkyl group; a $C_1$-$C_{10}$ alkyl group interrupted by a phosphate group —O—(HO—P=O)—O— optionally substituted by one or more groups selected from: hydroxy-OH, carboxy-COOR$_1$, oxycarbonil-($C_8$-$C_{16}$)alkyl and oxycarbonil-($C_8$-$C_{16}$)alkenyl; where R$_1$ is hydrogen H or a $C_1$-$C_4$ linear or branched alkyl group; or Y' is a monophosphate ester of a substituted or partially substituted glycerol, having at least one functional group of said glycerol esterified with an aliphatic fatty acid with saturated or unsaturated carbon chains, and the phosphoric acid function is either free or salified with an alkali or earth alkali metal;

L is a bivalent linker selected from: aliphatic $C_3$-$C_{10}$ cyclic and heterocyclic and a $C_1$-$C_6$ alkyl, $C_2$-$C_6$ alkenyl or alkynil, linear or branched group optionally substituted or interrupted with an atom or group selected from: carbonyl-C=O, thiocarbonyl-C=S, amino-$NR_1$—, carboxy-COO—, oxy-carbonyl-OCO—, amido-$NR_1$CO— or —$CONR_1$—, oxygen-O— and sulphur-S—, wherein $R_1$ is as defined above;

$R^{I-IV}$ and $R^{I-III}$ are each, independently a —($C_1$-$C_3$)alkylcarboxy group;

wherein said chelating moiety is complexed to a paramagnetic metal ion selected from the group consisting of: Gd(III), Mn(II), Cr(III), Cu(II), Fe(III), Pr(III), Nd(III), Sm(III), Tb(III), Yb(III), Dy(III), Ho(III) and Er(III).

The invention further relates to the process for preparation of said solid lipid nanoparticles comprising amphiphilic complexes of paramagnetic metals (pSLNs) and the resulting pSLNs as MRI contrast agents.

The process comprises the following steps:
a) preparing an organic phase (O) obtained by admixing in a low-boiling organic solvent, immiscible in water:
an amphiphilic component comprising a compound suitable for the coordination of metal ions, selected from a diazepine derivative of Formula I and a tetraazacyclododecane derivative of Formula II:

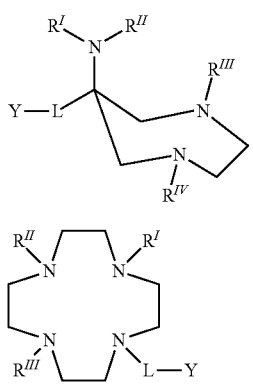

wherein:
Y Y is a group of formula Y'—NH— or (Y')$_2$—N—, wherein Y' is selected from the following groups: a linear or branched, saturated or unsaturated $C_8$-$C_{16}$ alkyl group; a $C_1$-$C_{10}$ alkyl group which can be interrupted by a phosphate group —O—(HO—P=O)—O— optionally substituted by one or more atoms or groups selected from: hydroxy-OH, carboxy-$COOR_1$, oxycarbonyl-($C_8$-$C_{16}$) alkyl and oxycarbonyl-($C_8$-$C_{16}$)alkenyl groups; wherein $R_1$ is selected from hydrogen H and a linear or branched $C_1$-$C_4$ alkyl group.

L is a bivalent linker selected from: aliphatic $C_3$-$C_{10}$ cyclic or heterocyclic, or $C_1$-$C_6$ alkyl, alkenyl or alkinyl, linear or branched group optionally substituted or interrupted with an atom or a group selected from: carbonyl-C=O, C=S thiocarbonyl-, amino-$NR_1$—, carboxy-COO—, oxy-carbonyl-OCO—, amido-$NR_1$CO— or —$CONR_1$—, oxygen-O— and sulphur-S—, wherein $R_1$ is as defined above;

$R^{I-Iv}$ and $R^{I-III}$ are each, independently, a —($C_1$-$C_3$)alkylcarboxy group, said chelating moiety complexed to a paramagnetic metal ion selected from the group consisting of: Gd (III), Mn (II), Cr (III), Cu (II), Fe (III), Pr (III), Nd (III), Sm (III), Tb (III), Yb (III), Dy (III), Ho (III) and Er (III);

an amphiphilic component selected from the group consisting of: a $C_6$-$C_{24}$ linear or branched saturated or unsaturated chain phospholipid, lysolipid, sphyngolipid and wherein surfactants such as a bile acid or derivatives thereof, a glycolipid, an aliphatic fat alcohol, a di-alkyl ether, tocopherol or mixtures thereof can also be present; and a lipid component comprising at least a glyceride selected from the group consisting of: monoglycerides, diglycerides and triglycerides with linear or branched, saturated or unsaturated hydrocarbon chains with length comprised between 12-24 carbon atoms, or mixtures thereof, and optionally a saturated $C_{12}$-$C_{22}$ fatty acid or an ester thereof, b) preparing an aqueous solution (W) comprising one or more ionic or -non-ionic surfactant and optionally a co-surfactant selected from a $C_3$-$C_8$ poly-alkyl alcohol and a fat saturated $C_5$-$C_{12}$ acid;

c) mixing the organic phase (O) prepared in a) with the aqueous solution (W) prepared in b), to obtain a micro-emulsion (W/O) stable and transparent at a temperature comprised between 20° C. to 40° C.;

d) adding the micro-emulsion (W/O) according to step c) to a second aqueous solution ($W_1$) comprising at least one ionic or non-ionic surfactant as tensioactive, at a temperature comprised between 20° C.-40° C. to obtain a multiple emulsion (W/O/$W_1$);

e) evaporating the organic solvent from the multiple emulsion and obtaining a suspension of lipid nanoparticles, f) cooling the suspension obtained at step e) to a temperature lower than the crystallization point of the lipid component as defined in step a) to obtain pSLNs.

Injectable compositions comprising the pSLNs of the invention are also described.

BRIEF DESCRIPTION OF THE DRAWINGS

FIG. 4. MR image acquired after administration of pSLNs at a dose of 0.05 mmol/kg.

FIG. 5. a) and b): In vivo organ biodistribution after administration of pSLNs containing B22286 complex in healthy C57BL/6 mice.

DETAILED DESCRIPTION OF THE INVENTION

Figure 1:
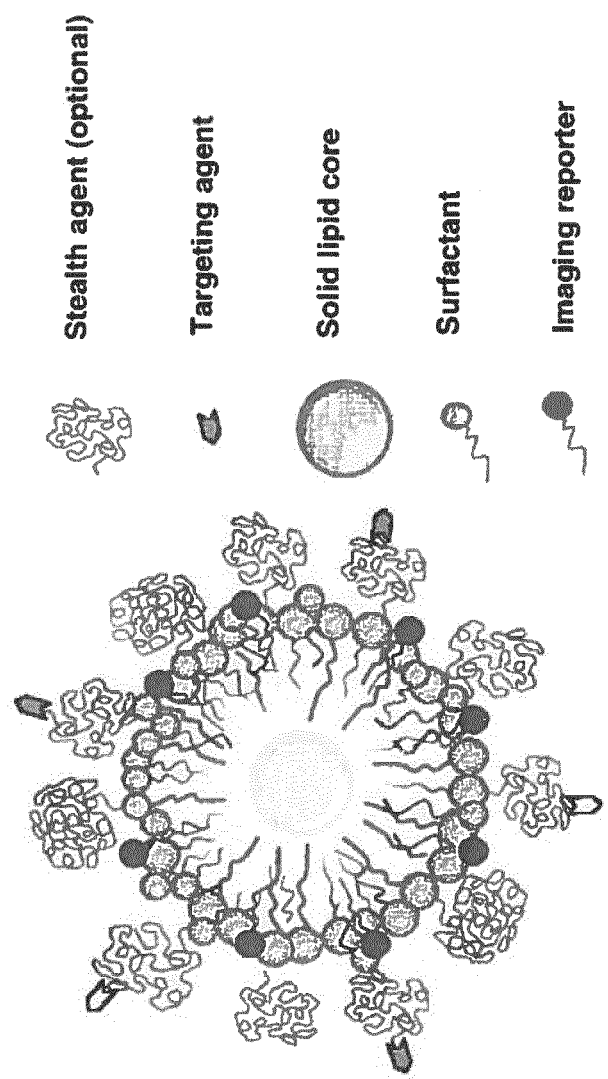
FIG. 1. Scheme of a paramagnetic solid lipid particle, optionally containing a stealth agent.

The present invention relates to a paramagnetic Solid Lipid Nanoparticle (pSLN) comprising an amphiphilic paramagnetic metal chelating moiety selected from: a diazepine derivative of Formula I and a tetraazocyclododecane derivative of Formula II:

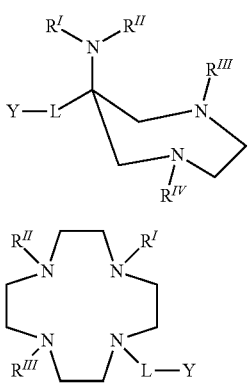

or salts thereof, wherein:

Y is a group of formula Y'—NH— or (Y')$_2$—N—, where Y' is selected in the group consisting of: a linear or branched saturated or insaturated $C_8$-$C_{16}$ alkyl group; a $C_1$-$C_{10}$ alkyl group interrupted by a phosphate group —O—(HO—P=O)—O— optionally substituted by one or more groups selected from: hydroxy-OH, carboxy-COOR$_1$, oxycarbonil-($C_8$-$C_{16}$)alkyl and oxycarbonil-($C_8$-$C_{16}$)alkenyl; where R$_1$ is hydrogen H or a $C_1$-$C_4$ linear or branched alkyl group; or Y' is a monophosphate ester of a substituted or partially substituted glycerol, having at least one functional group of said glycerol esterified with an aliphatic fatty acid with saturated or unsaturated carbon chains, and the phosphoric acid function is either free or salified with an alkali or earth alkali metal;

L is a bivalent linker selected from: aliphatic $C_3$-$C_{10}$ cyclic and heterocyclic and a $C_1$-$C_6$ alkyl, $C_2$-$C_6$ alkenyl or alkynil, linear or branched group optionally substituted or interrupted with an atom or group selected from: carbonyl-C=O, thiocarbonyl-C=S, amino-NR$_1$—, carboxy-COO—, oxy-carbonyl-OCO—, amido-NR$_1$CO— or —CONR$_1$—, oxygen-O— and sulphur-S—, wherein R$_1$ is as defined above;

R$^{I\text{-}IV}$ and R$^{I\text{-}III}$ are each, independently a —($C_1$-$C_3$)alkylcarboxy group;

wherein said chelating moiety is complexed to a paramagnetic metal ion selected from the group consisting of: Gd(III), Mn(II), Cr(III), Cu(II), Fe(III), Pr(III), Nd(III), Sm(III), Tb(III), Yb(III), Dy(III), Ho(III) and Er(III).

The pSLNs of the invention have on average the following composition:

Lipid component (which is mainly in the solid lipid core), represents about 30-50% (weight/weight), preferably 35-45%, and comprises at least one glyceride selected from the group consisting of: monoglycerides, diglycerides or triglycerides with saturated or unsaturated, linear or branched hydrocarbon chains with length ranging from 12-24 carbon atoms, with melting temperatures greater than 37° C., or mixtures thereof, and optionally a saturated or unsaturated, linear or branched fatty acid chain, containing from 12 to 24 carbon atoms, or an ester thereof. Preferably the fatty acid is selected from: myristic acid, palmitic acid, stearic acid, behenic acid or mixtures thereof. The fatty acid ester component can be represented, for example, by cetyl-palmitate. Optionally mono- or diesters of polyethylene glycol fatty acids and aliphatic alcohols may also be present which contain from 12 to 24 carbon atoms. In pSLNs the lipid component is in solid and crystalline form.

amphiphilic component which is primarily found around the lipid core and which is preferably a phospholipid, a lyso-lipid or a sphingolipid, linear or branched, saturated or unsaturated chain containing from 6 to 24 carbon atoms. It represents 27-45% (weight/weight) of pSLN, as defined in step a) of the process. It is preferably a phospholipid and even more preferably represents about 33-38% of pSLN. As said above it is primarily found around the lipid core, together with the amphiphilic component of the paramagnetic complex; and the amphiphilic component consisting in a paramagnetic complex, which represents 5-14%, more preferably 8-12%, of the pSLN and is a complex of Formula I and/or Formula II.

For the purposes of the present invention, by "solid lipid core" it is intended a lipid core which is solid up at least to body temperature (37° C.) (this value included), preferably up to a temperature of 42° C. and even more preferably up to a temperature of 55° C. (all intermediate values comprised). A schematic is shown in FIG. 1.

In a preferred embodiment of pSLNs, where the surfactant in the amphiphilic component is a phospholipid or a derivative thereof, it's possible to express the content of amphiphilic complex relative to the content of phosphorus present in the system. In this case, the amphiphilic complex is about 10-30% and preferably 17-23% molar with respect to phospholipids. In fact, for a representative pSLNs comprising the complex 9b, the P/Gd (III) ratio is less than 6, preferably 5 and corresponds, as better detailed in the experimental part to a load (payload) of Gd (III) of at least 10000, or more preferably at least 11000, 12000 molecular units of complex per particle.

The pSLNs optionally comprise polymeric coatings with "stealth" function eg. PEG (Poly Ethylene Glycol) preferably having a molecular weight comprised from 500 to 10,000 daltons and more preferably from 2,000 to 5,000 daltons, as such or derivatized with alkyl functions and/or phospholipid, specific ligands for cellular receptors, non-derivatized or derivatized with alkyl functions, such as for example vitamins or peptides with ligand function. In a particularly preferred embodiment pSLNs includes DSPE-PEG 2000-Folate.

Contrast agents in the so-formulated pSLNs generally have a much higher relaxivity than commercially available low molecular weight macrocyclic complexes (see Table I) and are therefore able to provide a magnetic resonance image of diagnostic value with lower doses of the paramagnetic metal complex. Generally, with currently available MRI contrast agents the administered dose in the clinical setting is 0.1 mmol Gd/kg, while preclinical data with pSLNs show that it is possible to obtain diagnostic images with lower doses. Moreover, high relaxation rate, i.e. high relaxivity values, ensure a fast acquisition of diagnostic information and a clear identification of the contrast medium in the examined region with lower doses as compared to traditional MRI contrast agents.

In general, the pSLNs according to the present invention are characterized by high relaxivity values $r_{1p}$ both in aqueous solution (data not shown) and under physiological conditions (from 25-50 mM$^{-1}$s$^{-1}$) as better described in the experimental section (Tables 3 and 4). In fact pSLN relaxivity values $r_{1p}$ at 0.47 T are typically higher than 25 mM$^{-1}$s$^{-1}$, preferably higher than 30 mM$^{-1}$s$^{-1}$, more preferably comprised from 25-50 mM$^{-1}$s$^{-1}$ measured in physiologic conditions.

Figure 2:
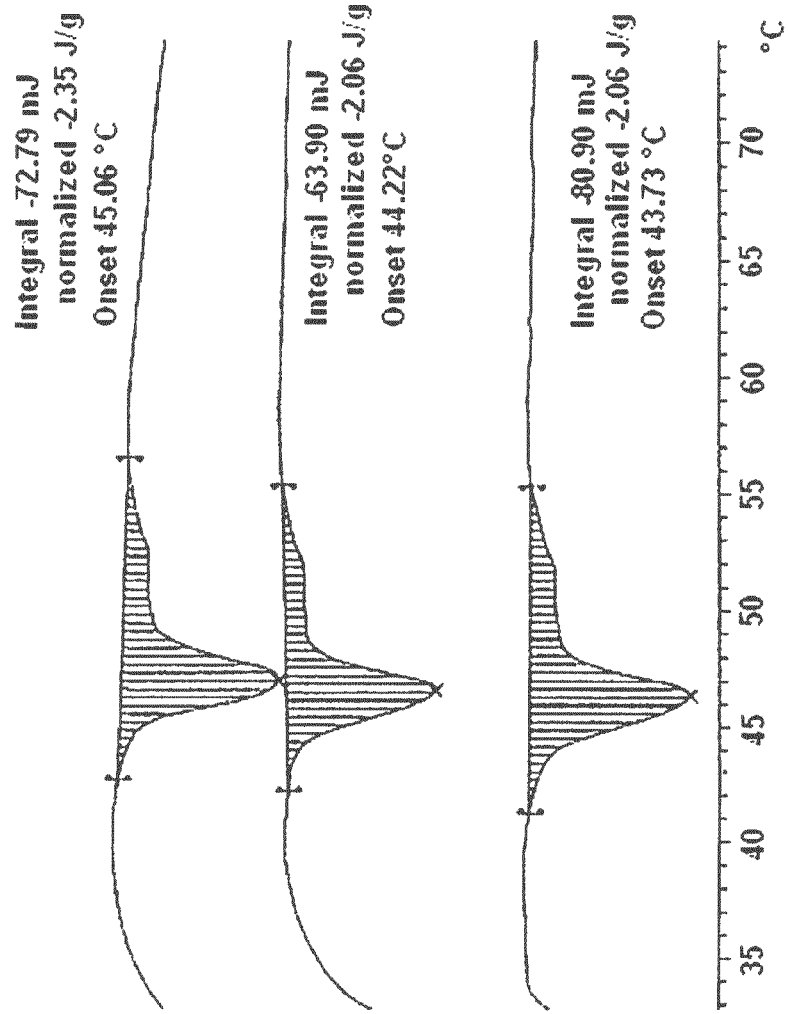
FIG. 2. DSC scanning and endothermic peak of a typical pSLNs. Curve above immediately after the preparation, curve in the middle after one month, curve below two months after the end of the preparation.

The pSLN of the invention are characterized by a solid core as demonstrated by the data shown in FIG. 2.

The endothermic melting peak of a preferred pSLNs formulation, comprising essentially tripalmitin in the lipid core, is comprised from 42° C. to 55° C. This is consistent with the melting peak of tripalmitin which is around 47° C. (and onset value of 45° C.) and which corresponds to the melting temperature of one of the metastable polymorphic form of tripalmitin (see Chapman D. "The polymorphism of glycerides" 1962 and Windbergs et al. AAPS PharmSciTech, 2009, 10: 1224-1233). DSC scanning as shown in FIG. 2, allows to qualitatively define the presence of a solid structure in the core of the SLNs.

For more complex compositions of the solid lipid core, the melting peak should be comprised from 37° C. to 55° C. The pSLNs can also be characterized by more than one melting peaks, when one or more polymorphic forms of a single lipid component or of different polymorphic forms of a mixture of two or more lipid forms are present.

Without wishing to be bound to a particular theory, the pSLNs of the present invention are more stable than nanoemulsions or liposomes due to the presence of the solid core in their inner structure. This also allows an optimal orientation of the chelated Gd (III) ions toward the external environment and a better accessibility of the water protons with consequent high effectiveness in reducing both longitudinal and transverse water proton relaxation time.

As better shown in the Experimental Section, Table 10, pSLNs according to the invention show optimal biodistribution and Gd accumulation properties in the medium long time range (10 days). They show, in general, a higher tropism for the liver (in particular for hepatocytes) than other lipid-based particulate systems (e.g. mixed micelles, see Anelli et al. MAGMA 2001, 12: 114-120). Liver is the organ where pSLNs are mostly concentrated within 6 hours after intravenous administration, although they have an equally high clearance rate allowing reduced accumulation in the medium-long term range (at the time-points used gadolinium measurement is the indicator of the amount of complex present in the organs due to the extremely high kinetic stability of the coordination cages of amphiphilic complexes, in particular those in the complexes of Formula I which are therefore particularly preferred). Noteworthy the accumulation of gadolinium in the spleen (the other nanoparticles storage organ) is very low, and is generally lower than for other lipid based nanoparticulate system e.g. mixed micelles, see Anelli et al. MAGMA 2001, 12: 114-120. This is an important behaviour of pSLNs which directly demonstrates their capability to escape from the uptake of phagocytic cells in the spleen. This is also in agreement with the in vitro observation of a low uptake of the pSLNs of the invention by a monocytic-macrophage cell line U937 as compared to other lipid based particulate systems (liposomes). These experimental observations demonstrate the improved ability of the pSLNs of the invention to escape from the recognition of the phagocytic cells of the reticuloendothelial system (RES), which affects their biodistribution particularly increasing the amount of pSLNs delivered to the hepatocytes in the liver. Across the hepatocytes the gadolinium chelates can be eliminated from the body with a clearance which is dependent by the amphiphilicity of their chemical structure. The low accumulation of pSLNs in the phagocytic cells of the RES (Kupfer cells, monocytes and macrophages) is a key factor for their effective use in vivo. As the elimination processes of Gd(III) from the phagocytic cells can require a long time, the risk of toxic effects produced by the metal ion increases. Although the mechanisms of biodistribution and clearance of nanoparticles, in particular pSLNs have not yet been fully elucidated, it is proposed that the improved properties the pSLNs of the present invention may depend primarily on their optimized surface properties, which reduce their uptake in the phagocytic cells and secondarily by the properties of the selected paramagnetic metal complexes transported into the liver by pSLNs.

Clearance of Gd(III) complex in the liver was found to be modulated by the lipophilicity of the metal complexes incorporated in the pSLNs (i.e. by the length of their alkyl chains), as the in vivo results suggest.

In fact, biodistribution studies show that pSLNs prepared with different types of amphiphilic complexes have elimination profiles depending also on the chain length. Tables 8-9 and 10 show some examples of biodistribution measurements following administration of 50 μmol/kg of pSLNs in healthy C57BL/6 mice. The amount of metal in different organs has been reported as % relative to the administered dose (% injected dose, % ID). The results obtained with the different amphiphilic complexes used to prepare pSLNs according to the invention, seem to indicate that the difference in structure of the alkyl chains (such as length) and their nature (such as the presence of hydrolysable groups, such as phosphate, that makes chains more biodegradable) are together with the above, important factors to modulate their biodistribution and to adjust the uptake rate in hepatocytes and the subsequent efflux into the bile ducts.

Therefore, according to a preferred aspect, the invention relates to pSLNs prepared with the following amphiphilic compounds: 37a, 12d, 25a, 9b, 9c in order of preference with regard to their biodistribution (see Tables 8-9 in the experimental part). Particularly preferred are the compounds 37a and 12d.

According to an even more preferred aspect the above pSLNs contain molecular targeting and stealth agents, eg. receptor-specific ligands, such as preferably the DSPE-PEG 2000-Folate. Results of cellular uptake experiments show that pSLNs containing the folic acid derivative are characterized by higher affinity for cell lines over-expressing the folate receptor (eg. IGROV-1), by which they are efficiently internalized resulting, as expected, in a more intense MRI signal than those without folate. It's in fact generally known that tissue and organ distribution can be optimized by targeting agents to endogenous biological structures.

However, even in the absence of targeting molecules, the pSLNs of the invention give a detectable signal and represent a MRI diagnostic agent that can be used in vivo, as shown in the experimental part (FIG. 4).

As already pointed out for other SLNs-based systems, biodistribution and organ clearance of these extremely complex systems is also strongly affected by nanoparticle size and surface properties, such as surface charge density. In this regard the pSLNs of the invention are characterized by a particle distribution comprised between 10 and 220 nm, an average diameter (z-average)<100 nm and a polydispersity index (PdI)<0.2. Preferably pSLNs are characterized by an average diameter comprised from 50 to 70 nm and PdI comprised between 0.12-0.18 (see Experimental Part, Tables 5 and 6).

These properties are obtained according to the process of the present invention, where optimal dispersion of the amphiphilic complexes and their distribution around the lipid core can be standardly achieved. The process also has been found to optimize amphiphilic metal complexes incorporation, which results in an incorporation efficiency always higher than 55%.

In particular the higher incorporation efficiencies are obtained with complexes with a length of the alkyl and/or carboxyalkyl chains of at least 8 carbon atoms or more preferably between and 8-16 carbon atoms or even more preferably between 10-14 carbon atoms.

This results in a high payload of pSLNs with metal complexes, hence with the paramagnetic metal itself. This parameter, measured for some typical compounds as representative examples of Formula I and Formula II complexes, turns out to be greater than or equal to about 10000, 11000, 12000 molecular units of gadolinium per particle.

The pSLNs according to the invention also offer the advantage of an improved stability compared to micellar systems, since the solid core provides an anchorage factor for the layer of surfactant substances and the paramagnetic amphiphilic complexes. In fact, unlike known micellar systems, pSLNs do not modify their structure upon dilution.

The higher stability allows a more easily and a longer storage, also in the form of low concentration pSLNs dispersion ready for injection.

As mentioned above, pSLNs usually show very high relaxivity in physiological medium, higher than values typically found in non-derivatized hydrophilic gadolinium complexes, in particular when formulated in SLNs, as better detailed in the experimental part for some representative compounds. As an example, relaxivity values for some Gd(III)complexes are indicated below, where values measured in physiologic conditions refer to those in obtained HSA 4% in NaCl 0.9%. Some of these compounds are commercially available or do not contain lipophilic chains or have been formulated in SLNs (Ref. e).

TABLE I

Relaxivity values of some known compounds for MRI

| determined at 0.47 T, 25° C., pH 7 | Water | HSA 4% $r_{1p}$ (mM$^{-1}$s$^{-1}$) | Human plasma (HP) |
|---|---|---|---|
| Gd-DOTA$^a$ | 3.61 | 4.11 | 4.51 |
| Gd-HP-DO3A$^b$ | 3.32 | 3.85 | 4.80 |
| Gd-BT-DO3A$^c$ | 3.75 | 4.31 | 5.76 |
| Gd-AAZTA $^d$ | 7.64 | 8.72 | — |
| Gd-DOTA in SLN $^e$ | 4.9 | — | — |

$^a$Gadoterato meglumine [[1,4,7,10-tetraazacyclododecane-1,4,7,10-tetraacetate (4-)] gado-linate (1-)] meglumine
$^b$Gd-HP-DO3A: Gadoteridol[10- (2-hydroxyprop-1-yl) -1,4,7,10-tetraazacyclododecane-1,4,7-triacetate(3-)] gadolinium
$^c$Gd-BT-DO3A: Gadobutrol
$^d$ Aime et al. Inorganic chemistry, 43 (24), 2004
$^e$ Morel et al. E.J. Pharm. and Biopharm., 1998, 45: 157-163

As shown in Tables 3 and 4 pSLNs show higher relaxivity values than the chelated amphiphilic compounds in solution i.e. not formulated in pSLNs, as better detailed in the Experimental Part.

For this reason and for the characteristics mentioned above, the pSLNs of the invention are suitable as contrast agents for MRI.

Therefore, the present invention also comprises pharmaceutical compositions comprising the described pSLNs suspended in a suitable solution with physiologically compatible excipients, diluents or the like for diagnostic use.

They are particularly suitable as "blood pool" agents for their biodistribution characteristics, and for imaging studies of the cerebral microcirculation, in angiographic applications and whenever tissues permeability is altered, as in inflamed tissues also as a result of tumor pathologies.

The imaging method consists in deriving an MRI image after administration of a suitable dose of pSLNs according to the invention or physiologically compatible and sterile compositions thereof. A suitable quantity for obtaining a MRI image by using the pSLNs the invention is for example 25-100 µmol/kg.

The invention further relates to an optimized process for the preparation of solid lipid nanoparticles with the amphiphilic complexes of paramagnetic metals (pSLNs paramagnetic Solid Lipid Nanoparticles) defined above, comprising the following steps:

a) an organic phase (O) is initially prepared by dissolving in an organic solvent, immiscibile in water, the following components: an amphiphilic component represented by a complex of a paramagnetic metal and a surfactant selected from the group consisting of: phospholipids, sphingolipids and lysolipids characterized by linear or branched, saturated or unsaturated chains containing from 6 to 24 carbon atoms and wherein surfactants such as a bile acid or derivatives thereof, a glycolipid, an aliphatic fat alcohol, a di-alkyl ether, tocopherol or mixtures thereof can also be present as better detailed in the following, a lipid component, and optionally other amphiphilic and/or hydrophilic components (eg. polymers for surface coating, such as PEG, preferably PEG-2000, optionally further modified with appropriate ligands for specific recognition of endogenous biomolecules and/or lipophilic or amphiphilic components). Solubilization of these components is carried out by heating the organic phase (O) at a temperature comprised between 20° C. and 40° C., more preferably between 25-37° C., even more preferably between 30-35° C. The organic solvent used, immiscible in water, is low boiling, with an evaporation temperature comprised between 20° C. and 70° C. under atmospheric pressure or under controlled vacuum conditions. According to a preferred embodiment, the solvent is preferably selected from: methylene chloride, diethyl ether, ethyl acetate, ethyl formiate or mixtures thereof. Particularly preferred is methylene chloride.

The lipid component is selected from the group consisting of monoglycerides, diglycerides or triglycerides or mixtures thereof, with hydrocarbon chains of length comprised between 12-24 carbon atoms, with melting temperatures greater than 37° C. Monoglycerides are eg. glyceryl-1-monopalmitate or glyceryl-1-monostearate; diglycerides are eg. glyceryl-1,3-dilaurate, glyceryl-1,3-dipalmitate, glyceryl-1,3-distearate. The hydrocarbon chains may be saturated or unsaturated and may be branched or unbranched. Preferably the lipid component consists of triglycerides such as trimyristin, tripalmitin, tristearin and triarachidin or mixtures thereof. The lipid component may also be composed of a mixture of mono, di- or tri-glycerides such as for example the commercial mixtures known by the name of SOFTISAN® and Witepsol® preferably Witepsol® W35, H42, E76, E85 or SOFTISAN® 138, 142, 154.

Preferably the lipid component comprises one or more saturated or unsaturated, linear or branched fatty acid chains containing from 12 to 24 carbon atoms. Preferably fatty acids may be myristic acid, palmitic acid, stearic acid, behenic acid. The lipid component may also optionally be composed of esters of fatty acids such as, for example, cetylpalmitate. Polyethylene glycol mono- or diesters of fatty acids and aliphatic alcohols containing from 12 to 24 carbon atoms may optionally also be included. According to a particularly preferred embodiment, the lipid component comprises tripalmitin and stearic acid, even more preferably in a weight ratio comprised between 8-9.9 and 2-0.1 respectively. More preferably the ratio between tripalmitin and stearic acid is 9:1. According to a particularly preferred embodiment an amphiphilic component such as DSPE-PEG 2000 is added to the lipid component. In addition when the insertion of a component is needed which is able to specifically recognize tumor cells over-expressing the folate receptor, an amphiphilic component derivatized with folate (eg. DSPE-PEG 2000-Folate) may be further added.

The amphiphilic complex of a paramagnetic metal is selected from the group consisting of derivatives of Formula I and/or Formula II, coordination compounds of metal ions, characterized by a lipophilic aliphatic part and a coordination cage.

Such coordination cage mainly belongs to two classes: diazepine derivatives (Formula I) and tetraazacyclododecane derivatives (Formula II).

The amphiphilic structures derived from the diazepine-type coordination-cage are characterized by the formula (I) or a salt thereof:

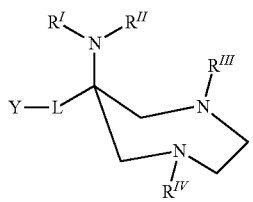
(I)

The amphiphilic structures with a tetraazacyclododecane-type coordination cage are characterized by the formula (II), or a salt thereof:

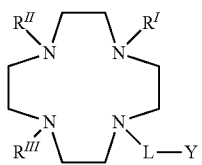
(II)

wherein for both formula I and II:
Y is a group of formula Y'NH— or (Y')$_2$N—, wherein Y', which in case of (Y')$_2$N— can be the same or different is selected from the following: a linear or branched saturated or unsaturated $C_8$-$C_{16}$ alkyl group, a $C_1$-$C_{10}$ alkyl group, optionally interrupted by a group —O—(HO—P=O)—O, or optionally substituted by one or more atoms or groups selected from the group consisting of: hydroxy-OH, carboxy-COOR$_1$, oxycarbonyl-($C_8$-$C_{16}$)alkyl and oxycarbonyl-($C_8$-$C_{16}$)alkenyl groups; wherein R$_1$ is selected from hydrogen H and a linear or branched $C_1$-$C_4$ alkyl group; or Y' is a monophosphate ester of a substituted or partially substituted glycerol, having at least one functional group of said glycerol esterified with an aliphatic fatty acid with saturated or unsaturated carbon chains, and the function of phosphoric acid is either free or salified with alkali or earth alkali metal.
L is a bivalent linker selected from: aliphatic $C_3$-$C_{10}$, cyclic or heterocyclic or a linear or branched $C_1$-$C_6$ alkyl or alkinyl group, optionally substituted or interrupted with an atom or a group selected from: carbonyl-C=O, thiocarbonyl-C=S, amino-NR$_1$—, carboxy-COO—, oxycarbonyl-OCO—, amide-NR$_1$CO— or —CONR$_1$—, oxygen-O— and sulphur-S—, wherein R$_1$ is as defined above;

R$^{I\text{-}IV}$ and R$^{I\text{-}III}$ are each, independently a —($C_1$-$C_3$)alkylcarboxy group, The Y group is linked to the L group preferably by means of an amide bond between a terminal nitrogen atom of the Y group and a carbonyl (—C=O) or thyocarbonyl (—C=S), present at the terminal end connecting with Y. Preferably, the Y group is in the form: (Y')$_2$—N— wherein the Y' residues are the same or different and are alkyl chains, with length $C_8$-$C_{16}$, preferably $C_{10}$-$C_{14}$, and are more preferably $C_{10}H_{21}$ and $C_{12}H_{25}$.

According to a preferred embodiment, the Y group has therefore formula:

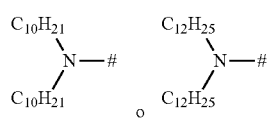

wherein # indicates the point of attachment to the linker L.

Alternatively, the Y group may also have the formula: Y'—NH—, wherein Y' is a $C_8$-$C_{16}$ alkyl group, more preferably a $C_{10}$-$C_{14}$ alkyl group, interrupted by one or more phosphate groups of formula:

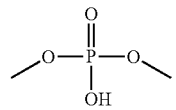

According to this embodiment, Y is a phospholipid having the formula: Y'—NH— wherein Y' is a $C_{10}$-$C_{14}$ alkyl group, interrupted by one or more phosphate group as defined above, further substituted with at least one and preferably 2 or 3 carboxyalkyl groups containing 8-16 carbon atoms, or more preferably 10-14 carbon atoms.

In a further alternative embodiment, Y is a monophosphate ester of a substituted or partially substituted glycerol, having at least one functional group of said glycerol esterified with an aliphatic fatty acid with saturated or unsaturated C—C chains, and the other function of phosphoric acid being either free or salified with alkali or earth alkali metals.

According to this further alternative embodiment, Y is selected from the following groups:

a)
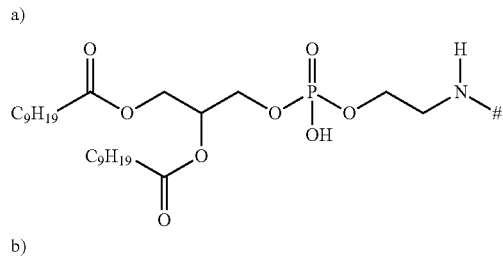

b)
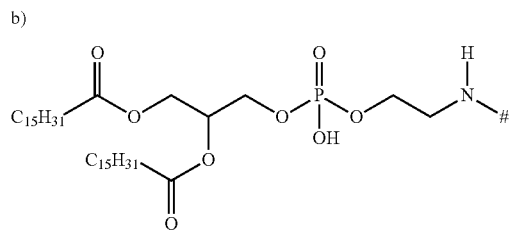

c)

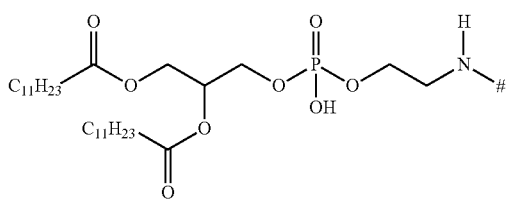

wherein # indicates the point of attachment to the linker L.

Particularly preferred are the complexes that use chelating agents of Formula I.

The linker L is a bivalent group which in the derivatives of formula (I) connects the diazepine moiety to the Y group and, similarly, in the derivatives of formula (II) connects the tetraazacyclododecane to the Y group.

L is a group selected from: a linear or branched $C_1$-$C_6$ alkyl, alkenyl or alkynyl group, optionally functionalized at one terminal side with a thiocarbonyl group (—C=S), or more preferably with a carbonyl group (—C=O) as a point of attachment for the terminal nitrogen atom of the Y residue in the formula (I).

Preferably, the linker L is a carbonyl-alkyl derivative selected from: substituted or non-substituted linear $C_1$-$C_6$ alkyl derivatives and $C_6$-$C_8$ cycloalkyl derivatives, having a carbonyl function at the terminal side connected to the Y group. Some examples of linkers are: methylcarbonyl, ethylcarbonyl, propylcarbonyl, butylcarbonyl, pentylcarbonyl and linear or cyclic hexylcarbonyl.

For the compounds of formula (I), more preferably the linker L is selected from: butyl-carbonyl of formula d) and cyclohexyl-carbonyl of formula e).

d)

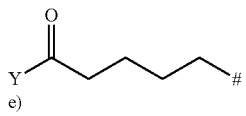

e)

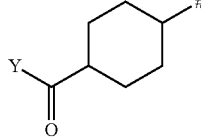

wherein # indicates the point of attachment to a diazepine of formula (I).

For the compounds of formula (II), the linker L is preferably selected from: methyl carbonyl of formula f) and carboxypropylcarbonyl of formula g)

f)

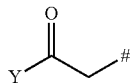

g)

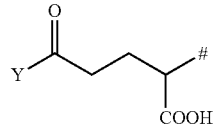

wherein # indicates the point of attachment to tetraazacyclododecane of formula (II).

As indicated above, the linker L is attached on one end to the Y group and on the other end to the diazepine or tetraazacyclododecane. The Y group of formula Y'—NH— or (Y')$_2$—N— has a terminal nitrogen atom to which the linker L is attached through an amide bond.

For compounds of formula (I), preferably LY-systems are selected from:

h)

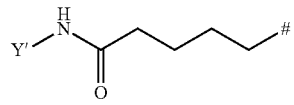

i)

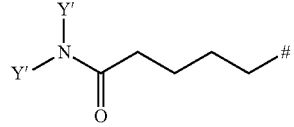

l)

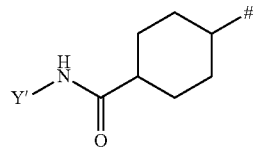

m)

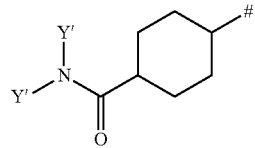

wherein Y' is in agreement with the above definitions and # indicates the point of attachment to diazepine of the derivative of formula (I).

For the compounds of formula (II), L-Y-systems are preferably selected from:

n)

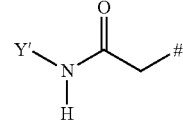

o)
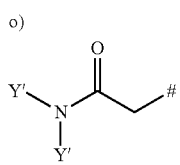
p)
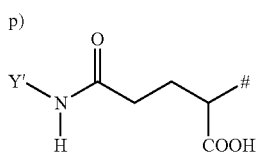
q)
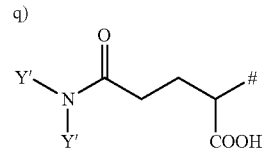
wherein Y' is defined as above and # indicates the point of attachment to tetraazacyclododecane of the derivative of formula (II).
According to a preferred embodiment the pSLN preferably comprises compounds of formula (I) selected from the group consisting of:
(VI)
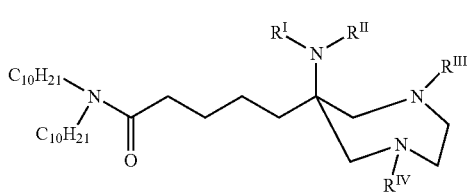
(VII)
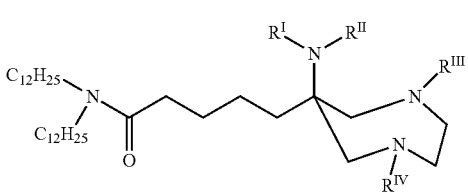
(VIII)
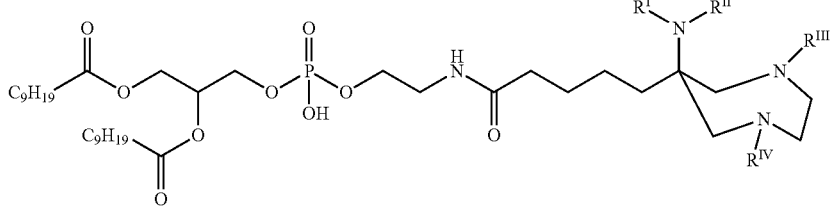
(IX)
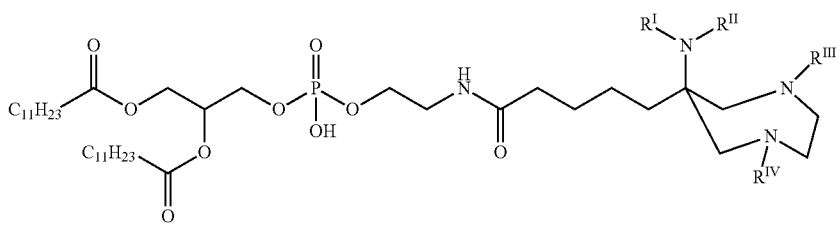
(II)
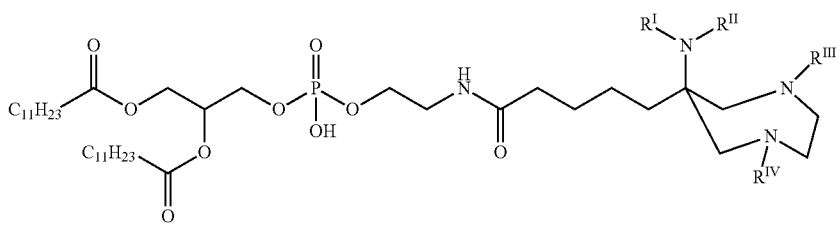
(X)
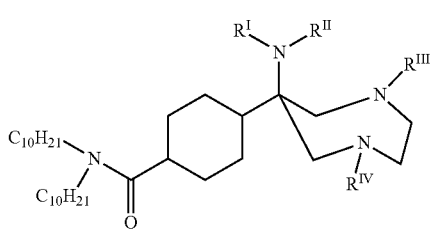

-continued

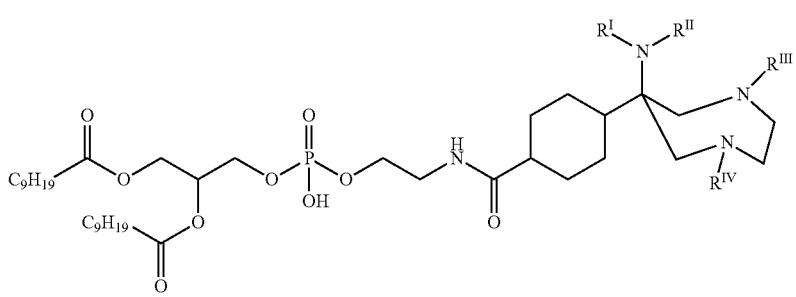

(XII)

wherein $R^{I-IV}$ are as above defined.

According to a preferred embodiment, the groups $R^{I-IV}$ are the same and are: $CH_2$—COOH. The chelating moiety is complexed to a paramagnetic metal ion selected from the group consisting of: Gd(III), Mn(II), Cr(III), Cu(II), Fe(III), Pr(III), Nd(III), Sm(III), Tb(III), Yb(III), Dy(III), Ho(III) and Er(III), wherein preferred is Gd(III).

Therefore, the preferred chelating agents of formula (I) are defined by the general formula (I'):

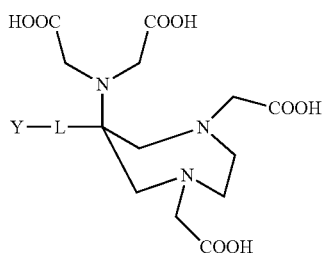

(I')

or a salt thereof, preferably in the form of a complex with a paramagnetic metal ion, preferably $Gd^{3+}$, wherein L and Y and their combination of L-Y are as in the preferred embodiments described above.

Similarly the preferred chelating agents of formula II have general formula II', or of a salt thereof as defined above:

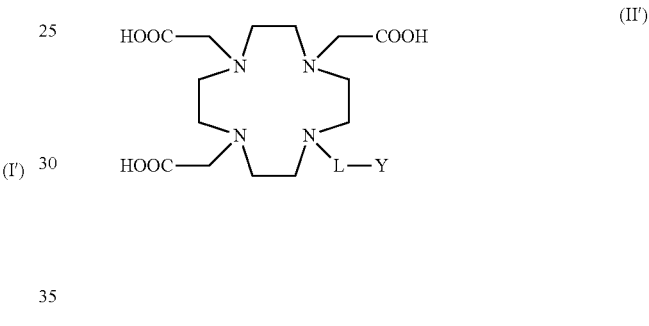

(II')

wherein L and Y, and their combination L-Y, are as in their preferred realizations described above.

Therefore, in agreement with the structure of Y and L, the compounds of formula (I') preferred for the preparation of pSLNs, in a form complexed to a paramagnetic metal ion selected from the group consisting of: Gd(III), Mn(II), Cr(III), Cu(II), Fe(III), Pr(III), Nd(III), Sm(III), Tb(III), Yb(III), Dy(III), Ho(III) and Er(III), preferably $Gd^{3+}$, and/or in the form of their physiologically compatible salt, are selected in the group consisting of:

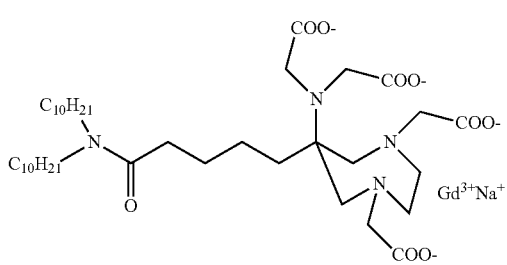

12 d

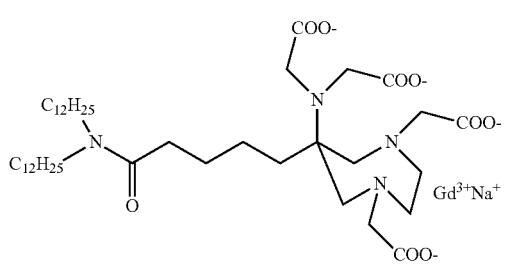

12 e

-continued
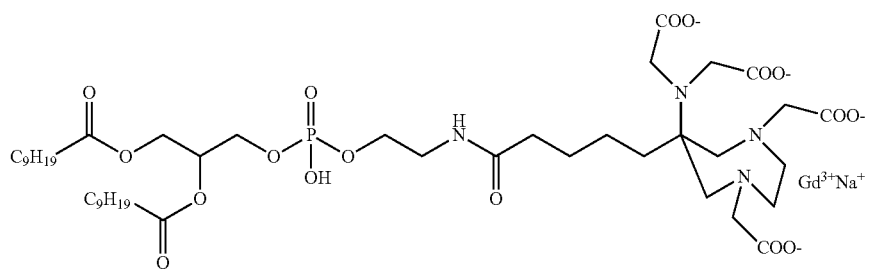
9a
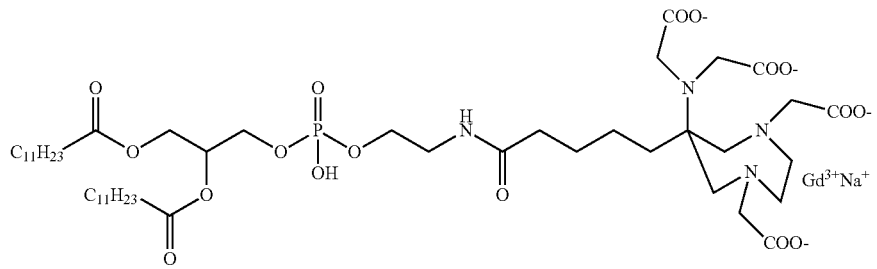
9b
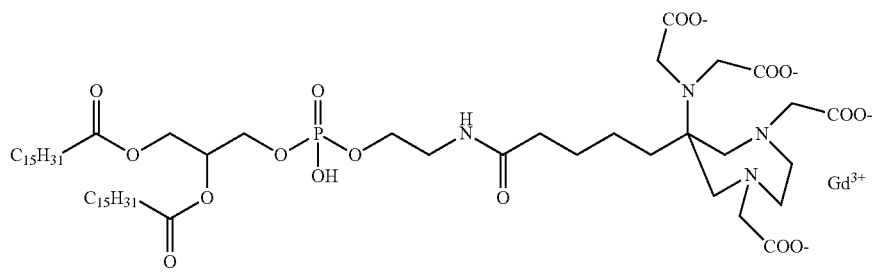
9c
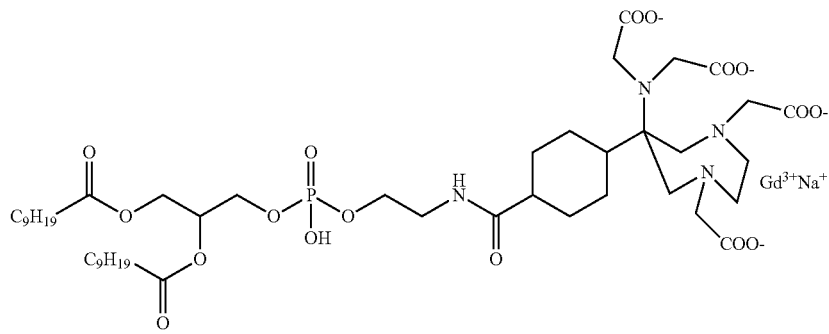
25c
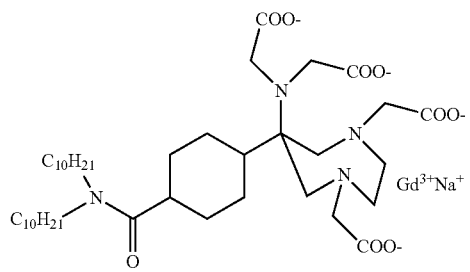
25a Preferred complexes of Formula II' are selected from the group consisting of:

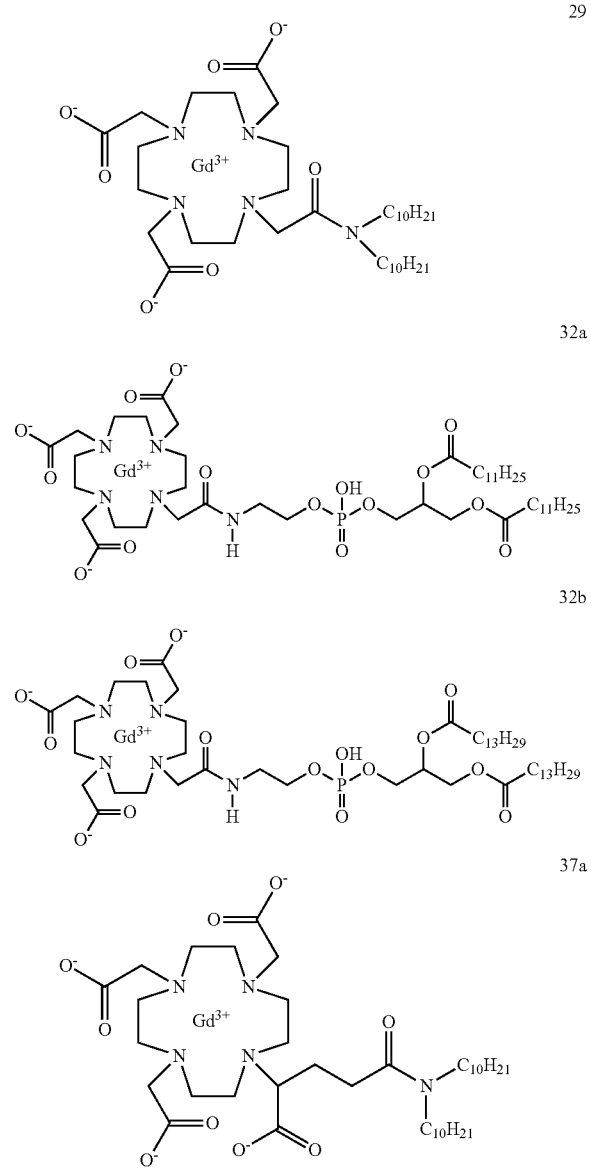

Particularly preferred are complexes: 37a and 32a and 32b.

The use of the above preferred complex of Formula I' and II' and of the above reported Gd(III) chelated complexes as particularly suitable for the preparation of pSLNs, is therefore also disclosed in the present invention.

The synthesis of amphiphilic chelating compounds is carried out according to methods briefly summarized in the following, or detailed in the experimental part.

As said above, in the method step a), one of the amphiphilic component is represented by a surfactant selected from the group consisting of:

phospholipids, sphingolipids and lysolipids characterized by linear or branched, saturated or unsaturated chains containing from 6 to 24 carbon atoms. This component is preferably a phospholipid, among which preferred are phosphatidylcholine, phosphatidylserine, phosphatidylethanolamine, phosphatidyl-inositol or mixtures thereof. Even more preferably the phospholipids are of natural origin such as soy or egg lecithin, both commercially available (Epikuron 200®, Epikuron 170® or Epikuron 100®, Lipoid® S 75, Lipoid® S 100 or egg lecithin Lipoid® E80).

The amphiphilic component with surfactant properties in step a) may also comprise bile acids or their salts, glycolipids, fatty acids, aliphatic alcohols, dialkyl ethers or tocopherol.

Other surfactants such as mono- or oligo-glycosides and their ethoxylated analogs mono, di- and tri-esters of glycerol with low melting point and preferably melted at room temperature can optionally be included during solubilization.

According to a preferred embodiment, reagents concentration in the organic phase O prepared in step a) can be summarized as follows:
lipid:
of which glycerides: 0.115-0.170 M,
of which phospholipid, when present: 0.115-0.170 M,
fatty acid, when present: 0.032-062 M
polymeric coating (i.e. PEG) when present: 0-0.018 M
paramagnetic complex: 0.014-0.038 M;
b) in parallel or subsequently, an aqueous phase (W) containing one or more surfactants and optionally a co-surfactant substance typically a poly-alkyl alcohol useful for increasing the solvating properties of the solvent used in step a), is prepared. Preferred surfactant substances in this phase are selected from low molecular weight ionic substances, even more preferably anionic surfactant substances selected from the group consisting of: cholic acid and derivatives thereof, eg. taurocholic acid or its hydrated salts, sodium cholate, sodium glycolate and sodium taurodeoxycholate. According to a particularly preferred embodiment sodium taurocholate (as emulsifier) is used, even more preferably combined with 1-butanol as co-solvent, dissolved to form the aqueous phase (W). Among anionic surfactants poly-alkyl-phosphates, alkyl-sulfates or sulfonates or alkyl-sulfosuccinates, such as dioctyl-sodium succinate can also be used.

As co-surfactant substances, poly alkyl alcohols containing from 3 to 8 carbon atoms such as monovalent alcohols (eg. 1-propanol, 1-butanol, 1-pentanol, 1-hexanol, 1-heptanol, 1-octanol, 3-heptanol and 4-pentanol), or diols such as esadiol or low molecular weight fatty acids such as butyric acid are used.

Optionally, the further hydrophilic components (eg. targeting agents, or polymeric systems, such as PEG) can be added in this phase;
c) the organic phase (0) prepared in a) is then gently mixed with the aqueous phase (W) prepared in b), to obtain a micro-emulsion (W/O) stable and transparent at the temperature defined in step a). The mixing time is generally about 20-30 minutes;
d) the micro-emulsion (W/O) obtained in step c) is then added to an aqueous solution ($W_1$) comprising at least an ionic or non-ionic surfactant or their mixtures at a temperature preferably selected from those defined in step a), to obtain a multiple emulsion (W/O/$W_1$).

Among non-ionic surfactants added in $W_1$ step d) as tensioactive, preferred ones are mono, di- and tri-ester derivatives of saturated and unsaturated fatty acids containing from 6 to 24 carbon atoms of sorbitan and analogous ethoxylated derivatives. More preferably, the formulation comprises polyoxymethylene sorbitan monooleate, commercially available as Polysorbate 80 (Tween® 80) and/or similar compounds such as Polysorbate 60 (Tween® 60), Polysorbato 40 (Tween® 40). Additional sorbitan derivatives such as Sorbitan monopalmitate (Span® 40) Sorbitan monostearate (Span® 60), Sorbitan monooleate (Span® 80) may also be included. Among non-ionic surfactant substances mono-di- or triester derivatives of $C_6$-$C_{24}$ fatty acids are preferred, for example ethoxylates. More preferably the non-ionic surfactant substance is polyoxyethylene sorbitan monooleate (Tween 80);

e) the organic solvent is removed from the multiple emulsion preferably by evaporation at atmospheric pressure or under controlled vacuum conditions. The evaporation can also be obtained by increasing the temperature of the multiple emulsion, up to a temperature above the evaporation temperature of the solvent used;

f) the suspension is slowly cooled in about 2 hours until reaching a temperature below the crystallization point of the lipid core; preferably the dispersion is cooled to 10° C. at a rate comprised between 0.1 and 0.4° C./min, preferably between 0.2 and 0.4° C./min even more preferably between 0.22 and 0.3° C./min and more preferably at 0.25° C./min.

A suspension of pSLNs is obtained that can be used, after suitable dilution, as a MR contrast agent and e.g. for research purposes.

In agreement with a preferred embodiment for the preparation of injectable contrast agents, the dispersion is then purified from the excess of non-incorporated components in the SLNs (step g) and sterilized (step h). The purification procedures may include dialysis, ultrafiltration or ultracentrifugation. Preferably the formulation is ultrafiltered by 30 kDa ultrafiltration membrane, preferably using an isotonic solution of glucose, and concentrated to a final gadolinium concentration comprised from 8 to 12 mM, more preferably from 9 to 11 mM. The formulation is then sterilized, for example by filtration through 0.22 μm filters.

With these compounds, the incorporation efficiency of the contrast agent in pSLNs, calculated as % metal complex included in pSLNs compared to the initial quantity dissolved in step a) of the preparation, is generally greater than or equal to 55%, preferably greater than 60%, 70% even more preferably greater than 80%.

In particular, at the end of the purification step, preferably carried out by direct ultrafiltration in a physiologically compatible and injectable liquid, a colloidal dispersion for injection is obtained in which the particulate phase is preferably about 5-16%, more preferably from 6-12% of the dispersion.

The particulate phase, consisting of a pSLNs whose structure is schematically represented in FIG. 1, is constituted by a solid crystalline core, formed by the lipid component (as identified in step a) of the preparation process comprising: monoglycerides, diglycerides or triglycerides having chain length $C_{12}$-$C_{24}$, saturated or unsaturated, linear or branched, or their mixtures. Preferably, the crystalline core comprises a single triglyceride, preferably selected among saturated triglycerides, more preferably tripalmitin. The core may also contain a saturated or unsaturated, linear or branched fatty acid or a fatty alcohol, with a $C_{12}$-$C_{24}$ chain, or their mixtures. Fatty acids such as mono- or di-ester of ethylene oxide may also be present, although a particularly preferred fatty acid is stearic acid or its salts. The lipid core is solid up at least to body temperature (37° C.) (this value included), preferably up to a temperature of 42° C. and even more preferably up to a temperature of 55° C. (all intermediate values comprised).

The core is surrounded by the components with amphiphilic characteristics and the surfactants as defined in steps a)-d) of the process for the pSLNs preparation, thus representing the interface with the external medium, generally aqueous, such as the blood or the pharmaceutical formulation. As outlined in FIG. 1, the amphiphilic component may optionally comprise a polymeric coating (stealth agent).

Following the purification and/or washing procedures, the dispersion of pSLNs should be considered free of the hydrophilic low molecular weight ionic surfactants used.

Accordingly, a further aspect of the invention relates to pharmaceutical compositions comprising the paramagnetic SLNs, prepared as described and comprising a metal ion chelating complex selected in the groups of general formula Formula I, Formula II, or more preferably of general Formula I' and II'.

For the purposes of the invention, formulas in the Description apply to the compounds in their optically pure form and to their racemic mixtures. Moreover, in general the term "complex" defines the amphiphilic compound with two types of coordination cages, when "complexed" with the paramagnetic metal, unless different specific definitions are provided in the description of the invention, obvious to a technician in the field. The preparation of the complexes with the metal is known in the art (see for example WO00/30688).

Furthermore compounds of formula I and I' and II or II' as defined herein may be in the form of a salt with physiologically acceptable bases or ions of organic or inorganic acids.

Particularly preferred bases are selected from primary, secondary or tertiary amines, basic amino acids and inorganic hydroxides of sodium potassium, magnesium, calcium or mixtures thereof. Anions of organic acids are: acetate, succinate, fumarate, maleate, oxalate; anions of inorganic acids are: sulphates, phosphates, phosphonates etc. Among amino acids are preferred lysine, arginine, ornithine, aspartic acid or glutamic etc.

According to a further embodiment the invention also relates to amphiphilic chelating agents of Formula (II'):

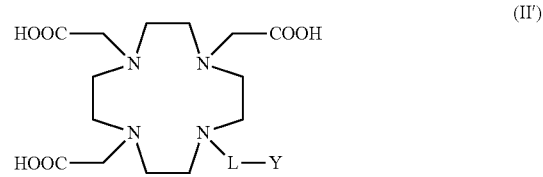

wherein:

Y is a group of formula Y'—NH— or (Y')$_2$—N—, wherein Y' is selected from the following groups: linear or branched, saturated or unsaturated $C_8$-$C_{16}$alkyl group; $C_1$-$C_{10}$ alkyl group which can be interrupted by a phosphate group —O—(HO—P=O)—O— optionally substituted by one or more atoms or groups of atoms selected from: hydroxy-OH, carboxy-COOR$_1$, oxycarbonyl-($C_8$-$C_{16}$)alkyl and oxycarbonyl-($C_8$-$C_{16}$)alkenyl groups; wherein R$_1$ is selected from hydrogen H and a linear or branched $C_1$-$C_4$ alkyl group, or a salt thereof.

L is a bivalent linker containing a linear or branched $C_1$-$C_6$ alkyl group, optionally substituted or interrupted with a group or an atom selected from: carbonyl-C=O, —NR$_1$-amino, carboxy-COO—, amide-NR$_1$CO— or —CONR$_1$— wherein R$_1$ is as defined above.

More preferred are the compounds:
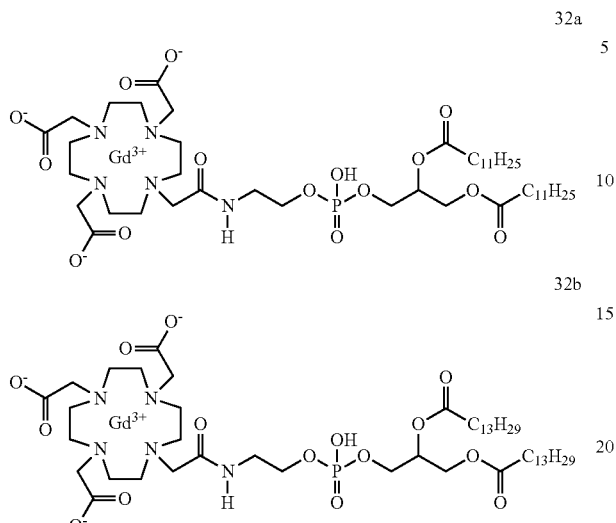
32a
32b
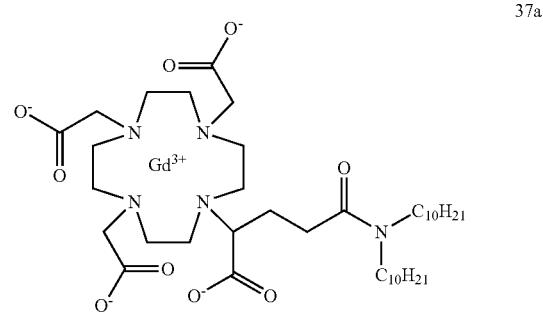
37a
Moreover, the invention comprises the use of the following compounds for the preparation of lipid nanoparticles, preferably solid, characterized by a high incorporation efficiency into the lipid layer or core, when used in the process of the invention:
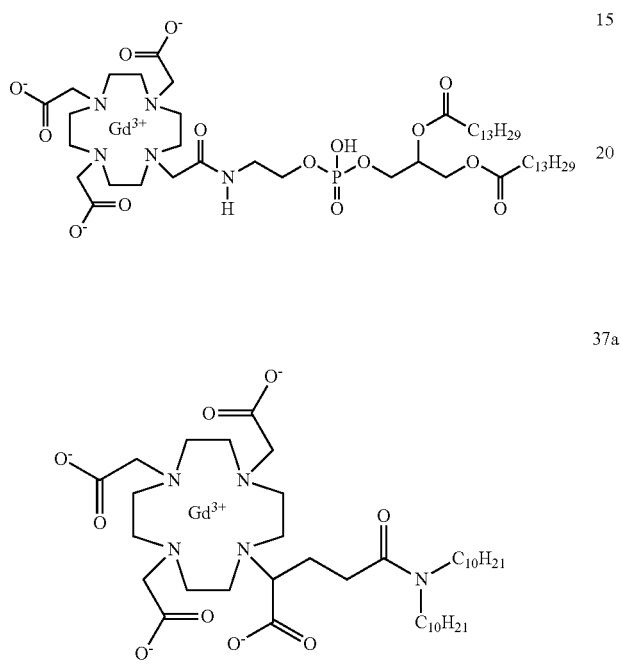
37a
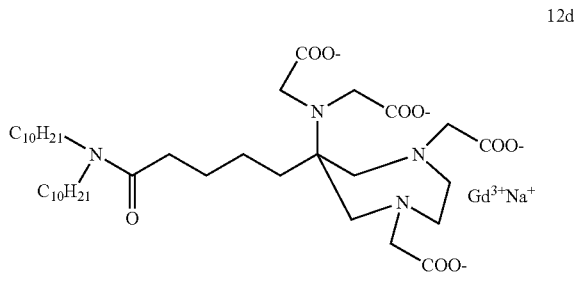
12d
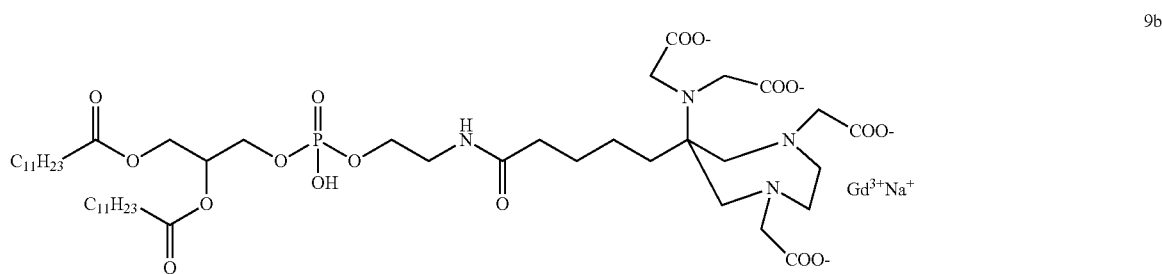
9b Synthesis of the Compounds of Formula I and II. General Scheme The compounds of formula (I) of the invention can be prepared by a process comprising at first the formation of an adduct between the selected linker L and the diazepine moiety, followed by activation of the carboxylic function on the terminal side of the linker, and subsequent amidation with the selected Y group. Finally, the protecting groups, where present in the obtained product, are removed and the derivative is optionally complexed with a selected paramagnetic metal.

The adduct between the linker L and the diazepine moiety referred as "reagent" of the synthetic process is obtained by reaction of a suitable nitro derivative, which is a precursor of the selected linker, with N,N'-dibenzylethylenediamine, which is the precursor of the diazepine. Subsequently the nitro group is reduced and functionalized, typically by hydrogenation and subsequent N-alkylation under basic conditions. Said adduct between the linker and the diazepine moiety can advantageously be prepared and used as building block for the preparation of a series of derivatives of formula (I) by varying the selected moiety Y.

Therefore, the synthesis for the preparation of a compound defined by formulas (I) and (II)

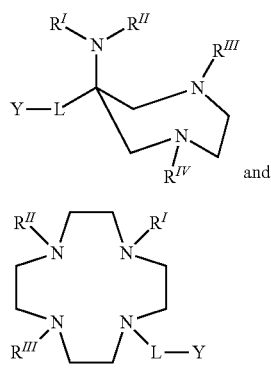

(I)

and

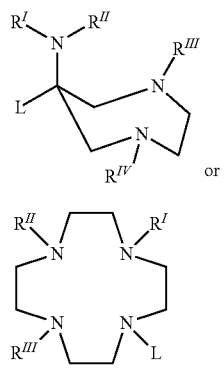

(II)

comprises the following steps:
a) preparation of an adduct of formula:

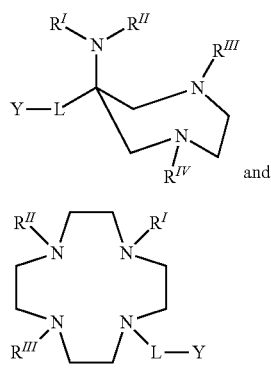

(I)

or

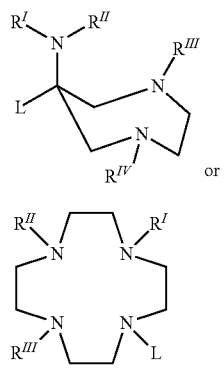

(II)

wherein $R^{I-IV}$ are as above defined and L is the linker comprising a terminal carboxylic function,
b) activation of said terminal carboxylic function of the linker
c) amidation reaction between the product of step b) and the Y group as above defined.

d) cleavage of any protecting group to give the derivative of formula (I) or (II);

e) chelation with a paramagnetic metal ion, to give the derivative of formula (I) or (II) in the form of a paramagnetic complex.

According to an illustrative example, the process of the invention can be generally represented by the processes for the preparation of derivative 12a, wherein the compound 5 is the starting adduct, as indicated below:

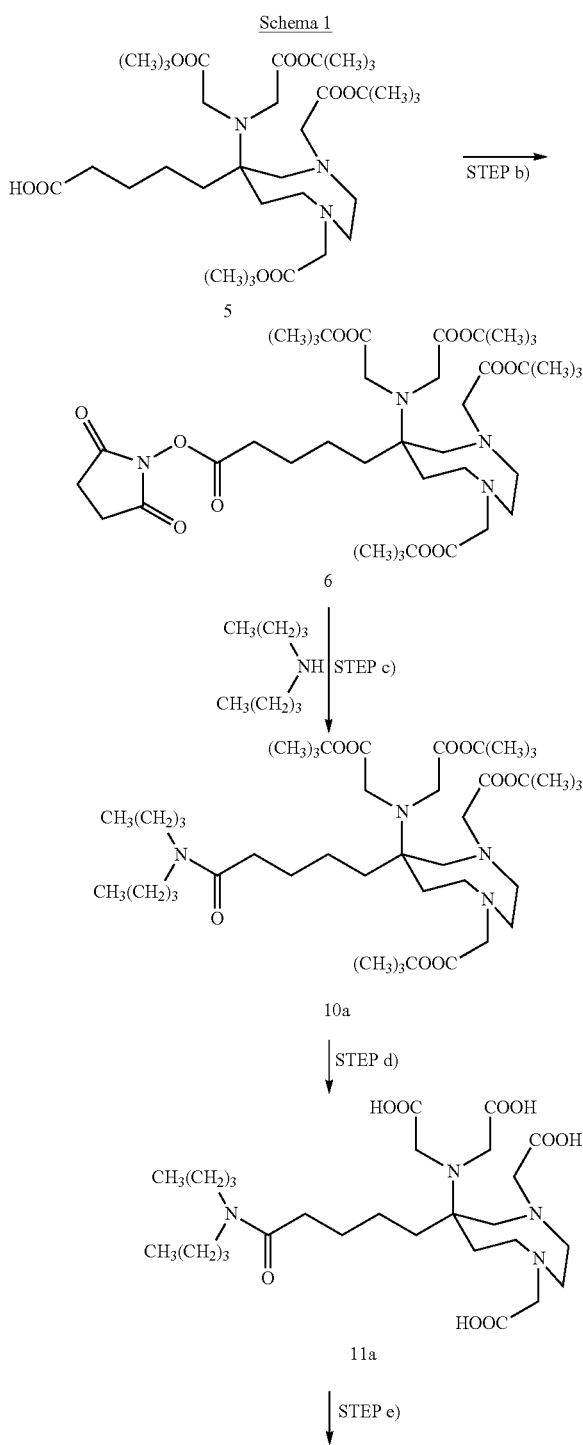

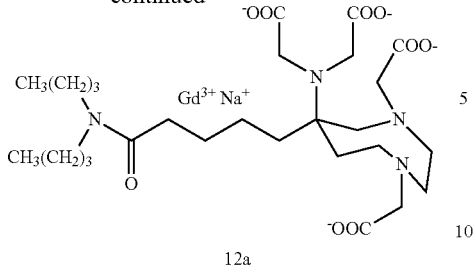

12a

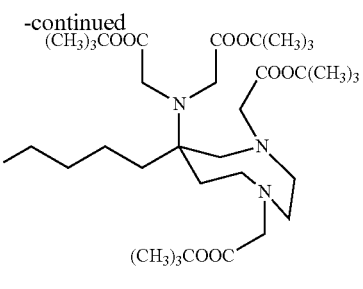

5

In particular, the adduct 5 between the linker and the diazepine moiety is prepared by reaction of N,N'-dibenzyethylenediamine diacetate and an alcoholic solution of 6-nitrohexanoic acid methyl ester 1, in the presence of paraformaldehyde followed by: reduction of the nitro group 2, functionalization of the amino derivative 3 and selective cleavage of the terminal carboxylic group 4, as indicated in Scheme 2, herein below:

Schema 2

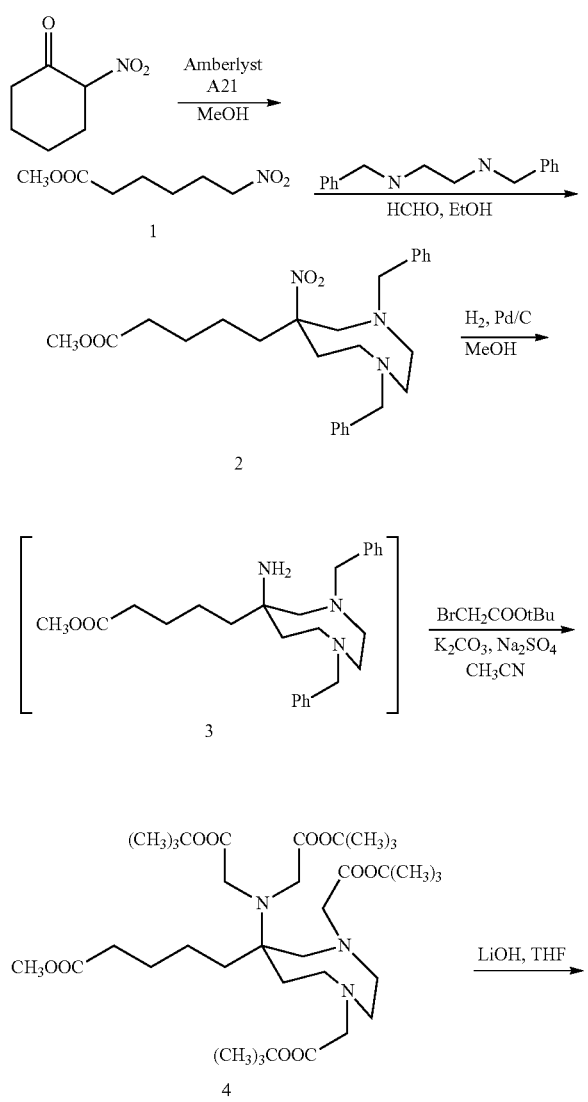

The diazepine derivative, as generally represented by compound 5, is subjected to the activation of the terminal carboxylic function as per step b) of the present process. The activation can be carried out according to procedures generally known in organic chemistry for the activation of carboxylic functions, typically by reaction with a carboxyl activating agent, such as N-hydroxysuccinimide (NHS) in the presence of a carbodiimide such as dicyclohexylcarbodiimide (DCC) or 1-ethyl-3-(3-dimethylaminopropyl)carbodiimide (EDC), in a molar ratio of at least 1:1 or preferably in a slight excess with respect to the starting material, e.g. in a molar ratio up to 1:1.5, in a proper organic solvent, such as an apolar organic solvent selected from: $CHCl_3$, $CH_2Cl_2$ and the like. Preferably, step b) is conducted in the presence of N-hydroxysuccinimide (NHS) and EDC in a molar ratio from 1:1 to 1:1.1 with respect to the starting material, and in the presence of $CH_2Cl_2$. The so-obtained derivative is then subjected according to step c) to an amidation reaction between the activated carboxylic terminal group of the linker L and the nitrogen atom of the selected Y residue for instance dibutylamine, generally in the presence of a diisopropylethylamine (DIPEA).

Preferably, the amidation reaction is carried out by dissolving the activated compound obtained after step b) in $CHCl_3$ and adding for instance dibutylamine and DIPEA in this order in a molar ratio from 1:1 to 1:1.7 with respect to the starting material. The solution is then stirred for a proper frame of time at a selected temperature, typically at room temperature (e.g. at a temperature comprised from 15 to 30° C.) generally for a period up to 20-24 hours. The thus formed amide product is then purified, e.g. by washing with water and by evaporating the separated organic phase, generally under vacuum or by distillation procedure. After purification, for instance by chromatography, the product of formula (I) is obtained in a protected form, e.g. preferably as tert-butyl ester derivative, in high yield (about 80%) and with a high degree of purity (about 95-99% HPLC).

According to step d) the derivatives of formula (I) obtained in their carboxylic protected form, can be readily deprotected under conditions known in the art, and dependent for instance on the kind of protecting group actually employed in step a). For a general reference on the choice of possible protecting groups, see "Greene's protective groups in organic synthesis" Wiley 14th Ed.

In a preferred embodiment, the carboxylic function is protected as tert-butyl ester, and the deprotection is carried out under acidic conditions, typically in the presence of trifluoroacetic acid (TFA) and an organic apolar solvent such as $CH_2Cl_2$.

The synthesis of the compounds of formula (II) was carried out starting from commercially available 1,4,7,10-tetraazacyclododecane-1,4,7,10-tetraacetic acid tris (1,1-dimethyl)ethyl ester 26, or from α-(2-carboxyethyl)-1,4,7,10- tetraazacyclododecane-1,4,7,10-tetraacetic acid tetra(1,1-dimethyl)ethyl ester 33 prepared according to the literature [Stuart G. Levy, Vincent Jacques, Kevin Li Zhou, Shirley Kalogeropoulos, Kelly Schumacher, John C. Amedio, Jonathan E. Scherer, Steven R. Witowski, Richard Lombardy, and Karsten Koppetsch Org. Process. Res. Dev. 2009, 13(3), 535-542].

Compounds 26 and 33 as defined in the experimental part have been subjected to activation of the carboxylic function, amidation reaction and deprotection of the protected carboxylic functions.

After deprotection, the so-obtained compounds of formula (I) and (II) can be suitably reacted with a metal ion containing compound in order to obtain the corresponding metal complex derivatives. Said transformation is typically carried out by reaction with an inorganic or organic salt or oxide of the selected metal, operating in the presence of a solvent such as water or organic solvent, e.g. $CHCl_3$ or MeOH, or mixture thereof. Preferred counter ions of the metal are chloride or acetate, and preferred salts are: $GdCl_3$, $Gd(OAc)_3$, whereas among preferred oxides: $Gd_2O_3$.

EXPERIMENTAL PART

Preparation of Compounds of Formula (I)

Esempio 1: Preparation of Compounds 9a-c According to the Scheme 3

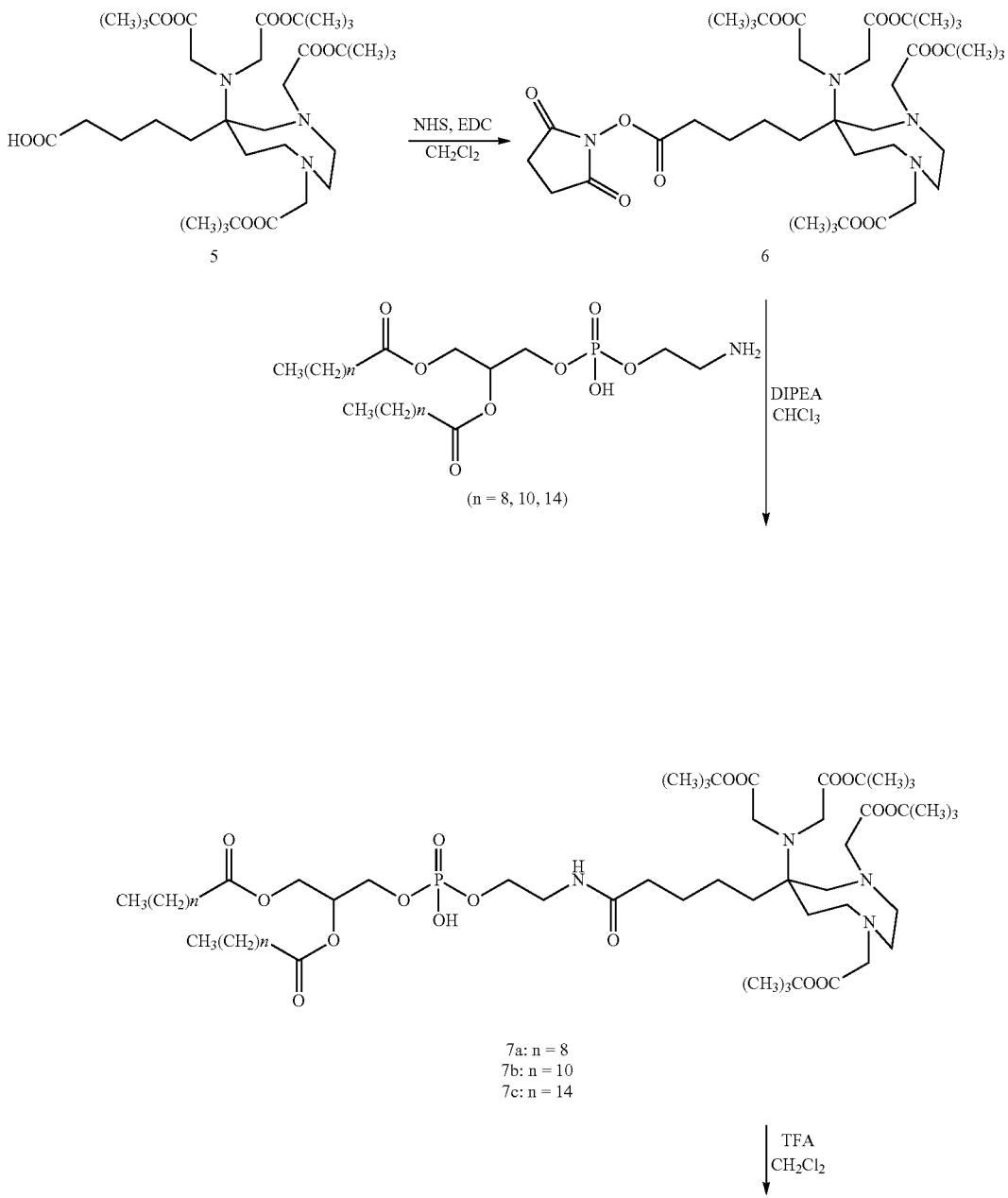

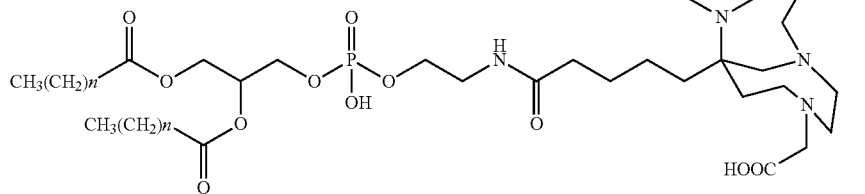
8a: n = 8
8b: n = 10
8c: n = 14
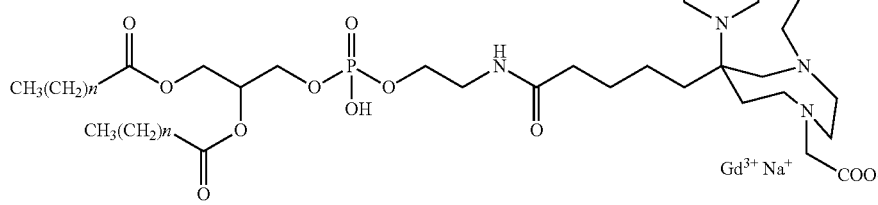
9a: n = 8
9b: n = 10
9c: n = 14
Example 1.1: Preparation of Compound 5
Compound 5 was prepared in five steps according to the procedure described in US2006018830 as illustrated in the Scheme 2 below.
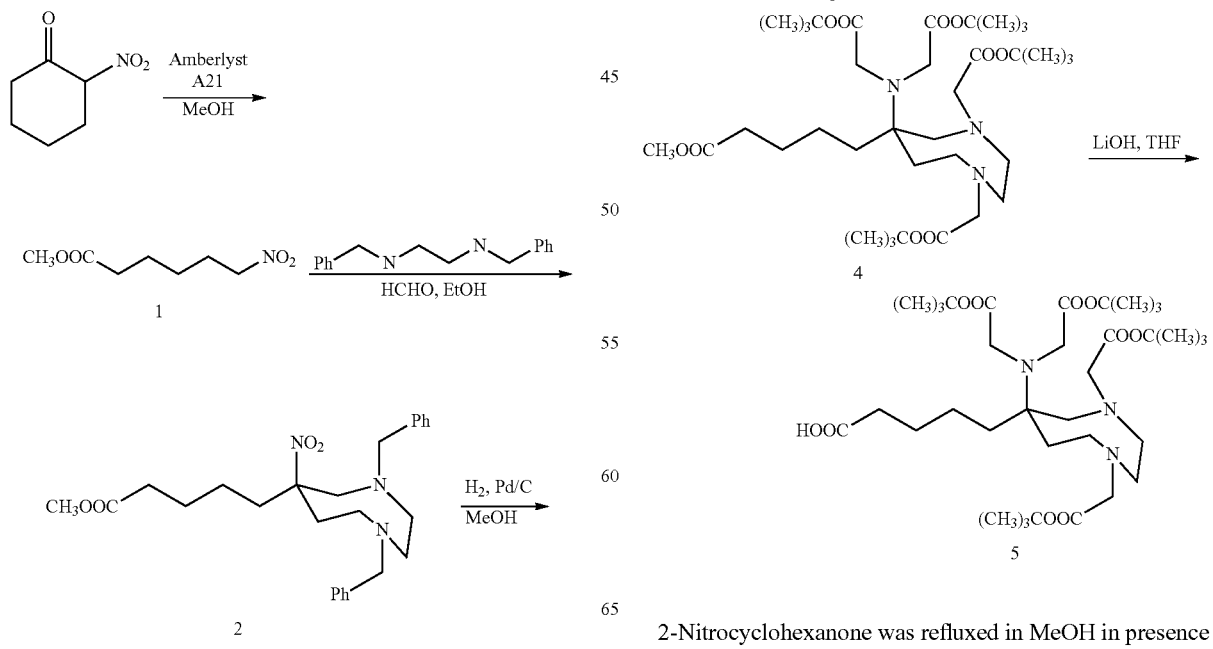
Schema 2
2-Nitrocyclohexanone was refluxed in MeOH in presence of Amberlyst A21 to give 6-nitrohexanoic acid methyl ester 1. Reaction of 1 with N,N'-dibenzylethylenediamine diacetate and paraformaldehyde gave diazepine 2 which was firstly hydrogenated to 3 and then alkylated with t-butyl bromoacetate to give pentaester 4. Selective hydrolysis of 4 by means of LiOH in THF/H$_2$O gave 5. Overall yield 13%.

Example 1.1a: Preparation of Compound 6

6-[Bis[2-[(1,1-dimethyl)ethoxy]-2-oxoethyl]amino]-6-[(2,5-dioxo-1-pyrrolidinyl)oxy]-5-oxopent-1-yl] tetrahydro-1H-1,4-diazepine-1,4(5H)-diacetic acid bis [(1,1-dimethyl)ethyl]ester Compound 5 (14.6 g; 0.022 mol) was dissolved in CH$_2$Cl$_2$ (350 mL), then NHS was added (3.75 g; 0.033 mol) and the mixture was cooled to 0° C. in an ice-bath. A solution of EDC (6.25 g; 0.033 mol) in CH$_2$Cl$_2$ (150 mL) was added dropwise, then the reaction solution was stirred for 24 h at room temperature. The mixture was washed with H$_2$O (3×150 mL). The organic phase was dried (Na$_2$SO$_4$), filtered and evaporated to give 6 as a yellow oil (15.42 g; 0.020 mol).
Yield 92%.
Analytical data:
Mr: 768.94 (C38H64N4O12)
1H- and 13C-NMR and MS are compatible with the structure Example 1.2: Preparation of Compounds 7a-c. General Procedure Compound 6 (1 eq) was dissolved in CHCl$_3$ (concentration 1% w/v). A suitable phosphoethanolamine (1 eq) (1,2-didecanoyl-sn-glycero-3-phosphoethanolamine, 1,2-dilauroyl-sn-glycero-3-phosphoethanolamine DLPE or dipalmitoyl-sn-glycero-3-phosphoethanolamine DPPE) and diisopropylethylamine (DIPEA) (1.7 eq) were added in this order. The solution was stirred at room temperature from 3 h to 24 h. The mixture was sequentially washed with H$_2$O (1×50 mL), acidified H$_2$O (pH 4-5 with HCl; 1×50 mL) and H$_2$O (1×50 mL). The organic phase was dried (Na$_2$SO$_4$), filtered and evaporated. The crude material thus obtained was purified by flash chromatography to give compounds 7a-c as a white solid material.

Esempio 1.2a: Preparation of Compound 7a

6-[Bis[2-[(1,1-dimethyl)ethoxy]-2-oxoethyl]amino]-6-[(13R)-10-hydroxy-10-oxido-5,16-dioxo-13-(1-oxodecyl)oxy]-9,11,15-trioxa-6-aza-10-phosphapentacos-1-yl]tetrahydro-1H-1,4-diazepine-1,4(5H)-diacetic acid bis[(1,1-dimethyl)ethyl]ester Reagents: Compound 6 (797 mg; 1.04 mmol); 1,2-didecanoyl-sn-glycero-3-phosphoethanolamine (543 mg; 1.04 mmol).
Compound 7a (937 mg; 0.796 mmol). Yield 77%.
Analytical data:
HPLC-ELSD: 100% (area %);
Mr: 1177.50 (C59H109N4O17P)
$^1$H- and $^{13}$C-NMR and MS are compatible with the structure.

Example 1.2b: Preparation of Compound 7b

6-[Bis[2-[(1,1dimethyl)ethoxy]-2-oxoethyl]amino]-6-[(13R)-10-hydroxy-10-oxido-5,16-dioxo-13-(1-oxodecyl)oxy]-9,11,15-trioxa-6-aza-10-phosphaeptacos-1-yl]-tetrahydro-1H-1,4-diazepine-1,4(5H)-diacetic acid bis[(1,1-dimethyl)ethyl]ester Reagents:
Compound 6 (700 mg; 0.91 mmol); 1,2-dilauroyl-sn-glycero-3-phosphoethanolamine DLPE (500 mg; 0.86 mmol)
Compound 7b (927 mg, 0.751 mmol). Yield 87%.
Analytical data:
HPLC-ELSD: 100% (area %); Mr: 1233.61 (C63H117N4O17P)
$^1$H- and $^{13}$C-NMR and MS are compatible with the structure.

Example 1.2c: Preparation of Compound 7c

6-[Bis[2-[(1,1dimethyl)ethoxy]-2-oxoethyl]amino]-6-[(13R)-10-hydroxy-10-oxido-5,16-dioxo-13-(1-oxodecyl)oxy]-9,11,15-trioxa-6-aza-10-phosphanonacos-1-yl]-tetrahydro-1H-1,4-diazepine-1,4(5H)-diacetic acid bis[(1,1-dimethyl)ethyl]ester Reagents:
Compound 6 (1.92 g; 2.50 mmol); 1, 2-dipalmitoyl-sn-glycero-3-phosphoethanolamine DPPE (1.73 g; 2.50 mmol).
Compound 7c (2.79 g; 2.07 mmol). Yield 83%.
Analytical data:
HPLC-ELSD: 100% (area %); Mr: 1345.82 (C71H133N4O17P)
$^1$H- and $^{13}$C-NMR and MS are compatible with the structure.

Example 1.3 Cleavage of t-Butyl Esters. General Procedure

Compound 7a-c (1 eq) was dissolved in CH$_2$Cl$_2$ (concentration 2-4% w/v) and the solution was stirred and cooled at 0° C., then TFA (6 eq) was added dropwise. The reaction mixture was stirred for 1 h at room temperature. The solution was evaporated and the residue dissolved in fresh TFA (30 eq). This solution was stirred for 80 h at room temperature; the reaction was monitored by MS analysis and HPLC-ELSD. The mixture was evaporated and the residue was treated with diisopropyl ether to obtain a white solid that was centrifuged and washed with diisopropyl ether (2×30 mL). That solid was suspended in H$_2$O, dissolved at pH 6-7 by addition of 5% aq NaHCO$_3$ and precipitated at pH 2 by addition of 1M HCl. The solid was filtered and dried at reduced pressure (P$_2$O$_5$) to obtain the ligands 8 a-c according to the data below.

Example 1.3a: Preparation of Compound 8a

6-[Bis[2-[(1,1dimethyl)ethoxy]-2-oxoethyl]amino]-6-[(13R)-10-hydroxy-10-oxido-5,16-dioxo-13-(1-oxodecyl)oxy]-9,11,15-trioxa-6-aza-10-phosphapentacos-1-yl]-tetrahydro-1H-1,4-diazepine-1,4(5H)-diacetic acid Reagents: Compound 7a (885 mg; 0.752 mmol).
Compound 8a (669 mg; 0.702 mmol); Yield 93%.

Analytical data:
HPLC-ELSD: 92.3% (area %)
Mr: 953.07 (C43H77N4O17P)
Complexometric titer (1.001 mM GdCl3): 95.7%
$^1$H- and $^{13}$C-NMR and MS are compatible with the structure.

Example 1.3b: Preparation of Compound 8b

6-[Bis[(carboxymethyl)amino]-6-[(13R)-10-hydroxy-10-oxido-5,16-dioxo-13-(1-oxodecyl)oxy]-9,11,15-trioxa-6-aza-10-phosphaeptacos-1-yl]-tetrahydro-1H-1,4-diazepine-1,4(5H)-diacetic acid Reagents: Compound 7b (875 mg, 0.709 mmol).
Compound 8b (750 mg; 0.642 mmol); Yield 91%.
Analytical data:
HPLC-ELSD: 75.5% (area %)
Mr: 1009.18 (C47H85N4O17P)
$^1$H- and $^{13}$C-NMR and MS are compatible with the structure.

Example 1.3c: Preparation of Compound 8c

6-[Bis[(carboxymethyl)amino]-6-[(13R)-10-hydroxy-10-oxido-5,16-dioxo-13-(1-oxodecyl)oxy]-9,11,15-trioxa-6-aza-10-phosphanonacos-1-yl]-tetrahydro-1H-1,4-diazepine-1,4(5H)-diacetic acid Reagents: Compound 7c (2.79 g; 2.07 mmol)
Compound 8c (1.77 g; 1.58 mmol); Yield 76%.
Analytical data:
HPLC-ELSD: 95.3% (area %)
Mr: 1121.39 (C55H101N4O17P)
Complexometric titer (1.001 mM GdCl3): 95.7%
$^1$H- and $^{13}$C-NMR and MS are compatible with the structure.

Example 1.4: Complexation in Aqueous Media. General Procedure

The ligands 8(a-c) (1 eq) were resuspended in H2O (concentration 5%; pH 1-2) and dissolved at pH 6.5-7 by addition of 5% NaHCO3 aqueous solution. A titrated solution of GdCl3 (1 eq) was added in portions. The solution was stirred at room temperature and pH was kept constant by addition of a 5% NaHCO3 solution. The complexation was monitored by HPLC-ELSD and with a Xylenol Orange assay. The complex was isolated by lyophilization and purified from salts by size exclusion chromatography to give compounds 9 a-c.

Example 1.4a: Preparation of Compound 9a

[[6-[Bis[(carboxymethyl)amino]-6-[(13R)-10-hydroxy-10-oxido-5,16-dioxo-13-(1-oxodecyl)oxy]-9,11,15-trioxa-6-aza-10-phosphapentacos-1-yl]-tetrahydro-1H-1,4-diazepine-1,4(5H)-diacetate(4-)] gadolinate(1-)]sodium Reagents: Compound 8a (400 mg, 0.438 mmol)
Compound 9a (257 mg, 0.228 mmol); Yield 52%.
Analytical data:
HPLC-ELSD: 98.9% (area %)
Mr: 1129.28 (C43H73GdN4NaO17P)
MS is compatible with the structure.

Example 1.4b: Preparation of Compound 9b

[6-[Bis[(carboxymethyl)amino]-6-[(13R)-10-hydroxy-10-oxido-5,16-dioxo-13-(1-oxodecyl)oxy]-9,11,15-trioxa-6-aza-10-phosphaeptacos-1-yl]-tetrahydro-1H-1,4-diazepine-1,4(5H)-diacetate(4-)] gadolinate(1-)]sodium Reagents: Compound 8b (690 mg, 0.590 mmol)
Compound 9b (614 mg; 0.518 mmol); Yield 88%.
Analytical data:
HPLC-ELSD: 95.6% (area %)
Mr: 1185.39 (C47H81GdN4NaO17P)
MS is compatible with the structure.

Example 1.4c: Preparation of Compound 9c

[6-[Bis[(carboxymethyl)amino]-6-[(13R)-10-hydroxy-10-oxido-5,16-dioxo-13-(1-oxodecyl)oxy]-9,11,15-trioxa-6-aza-10-phosphanonacos-1-yl]-tetrahydro-1H-1,4-diazepine-1,4(5H)-diacetate(4-)] gadolinate(1-)]sodium Reagents: Compound 8c (500 mg, 0.435 mmol)
Compound 9c (517 mg, 0398 mmol); Yield: 92%
Analytical data:
HPLC-ELSD: 99.2% (area %) [8]
Mr: 1297.60 (C55H97GdN4NaO17P)
MS is compatible with the structure.

Example 2: Preparation of Compounds 12d-e

Compounds 12d-e are prepared according to the scheme 4:

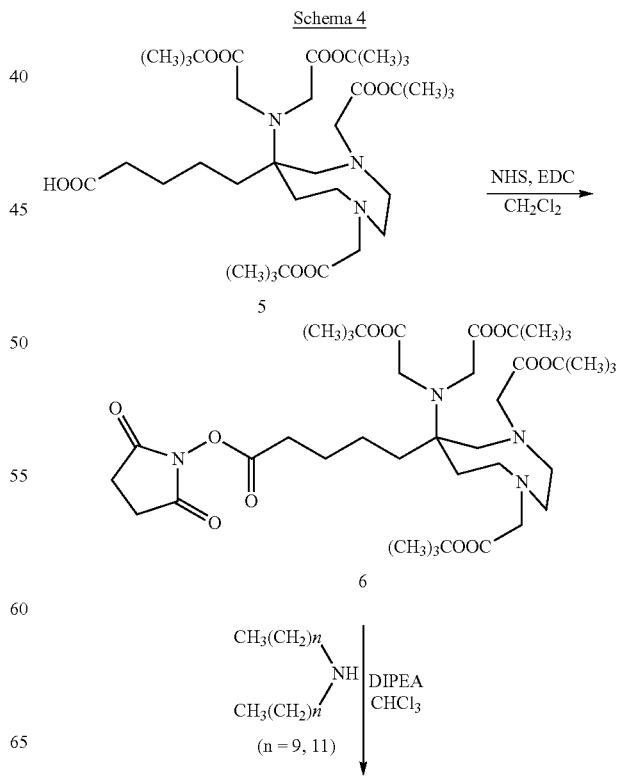

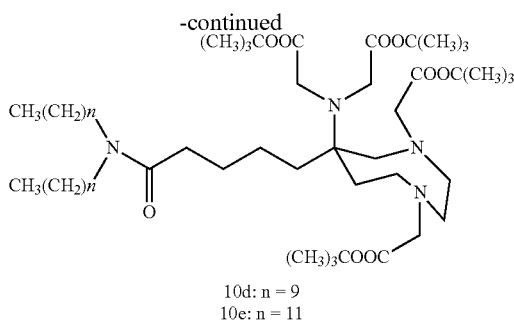

10d: n = 9
10e: n = 11

TFA
CH₂Cl₂

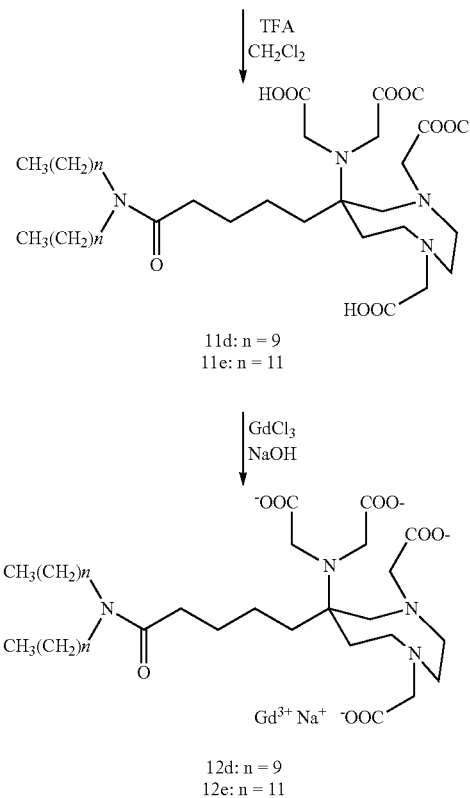

11d: n = 9
11e: n = 11

GdCl₃
NaOH

12d: n = 9
12e: n = 11

Example 2.1: Preparation of Compounds 10d-e.
General Procedure

Compound 6 prepared according to Example 1.1a (1 eq) was dissolved in CHCl₃ (concentration 1-3% w/v) with the dialkylamine (1 eq) and DIPEA (1.7 eq). The reaction solution was stirred at room temperature for 24 h and was subsequently washed with H₂O (1×50 mL), acidified H₂O (pH 4-5 with HCl; 1×70 mL) and H₂O (1×50 mL). The organic phase was dried (Na₂SO₄), filtered and evaporated. The so-obtained product was purified by flash chromatography to give compounds 10(d-e) as an oil, according to the results indicated below:

Example 2.1d: Preparation of Compound 10d

6-[Bis[2-[(1,1-dimethyl)ethoxy]-2-oxoethyl]amino]-6-[5-(didecylamino)-5-oxopent-1-yl]-tetrahydro-1H-1,4-diazepine-1,4(5H)-diacetic acid bis[(1,1-dimethyl)ethyl]ester Reagents: Compound 6 (1.92 g; 2.50 mmol); didecylamine (0.743 g; 2.50 mmol)
Compound 10d (2.26 g; 2:38 mmol). Yield: 95%.

Analytical data:
HPLC-ELSD: 95.3% (area %); Mr: 951.42 (C54H102N4O9)
¹H- and ¹³C-NMR and MS are compatible with the structure Example 2.1e: Preparation of Compound 10e 6-[Bis[2-[(1,1-dimethyl)ethoxy]-2-oxoethyl]amino]-6-[5-(dodecylamino)-5-oxopent-1-yl]-tetrahydro-1H-1,4-diazepine-1,4(5H)-diacetic acid-bis[(1,1-dimethyl)ethyl]ester Reagents: Compound 6 (3.13 g; 4.07 mmol); didodecylamine (1.44 g; 4.07 mmol)
Compound 10e (4.30 g, 4.27 mmol). Yield: 105% (solvent residue).
Analytical data:
HPLC-ELSD: 89.7% (area %); Mr: 1007.53 (C58H110N4O9).
¹H- and ¹³C-NMR and MS are compatible with the structure.

Example 2.2. Preparation of Compounds 11d-e.
General Procedure

Compounds 10d-e (1 eq) were dissolved in CH₂Cl₂ (20-50 mL) and the so-obtained solution was stirred and cooled to 0° C., then TFA (6 eq) was added dropwise. The reaction mixture was stirred for 1 h at room temperature. The solvent was evaporated and the obtained residue was dissolved in fresh TFA (50 eq). This solution was stirred for 80 h. The mixture was evaporated and the residue was treated with diisopropyl ether (70 mL) to obtain a white precipitate that was filtered or centrifuged, washed with diisopropyl ether (2×20 mL) and dried at reduced pressure (P₂O₅; NaOH pellets) to obtain ligands 11d and 11e as white solids. The crude product was resuspended in H₂O, dissolved at pH 6-7 by addition of 2N NaOH and precipitated at pH 2 by addition of 1M HCl.

Example 2.2d: Preparation of Compound 11d

6-[Bis[(carboxymethyl)]amino]-6-[5-(didecylamino)-5-oxopent-1-yl]-tetrahydro-1H-1,4-diazepine-1,4(5H)-diacetic acid Reagents: Compound 10d (2.20 g, 2.31 mmol)
Compound 11d (1.08 g; 1:48 mmol) Yield: 64%.
Analytical data:
HPLC-ELSD: 95.7% (area %)
Mr: 726.99 (C38H70N4O9)
Complexometric titer (1.001 mM GdCl3): 94%.
¹H- and ¹³C-NMR and MS are compatible with the structure.

Example 2.2e: Preparation of Compound 11e

6-[Bis[(carboxymethyl)amino]-6-[5-(dodecylamino)-5-oxopent-1-yl]-tetrahydro-1H-1,4-diazepine-1,4 (5H)-diacetic acid Reagents: Compound 10e (4.30 g, 4.27 mmol);
Compound 11e (2.83 g, 3.61 mmol) Yield: 85%.

Analytical data:
HPLC-ELSD: 82.4% (area %).
Mr: 783.10 (C42H78N4O9).
$^1$H- and $^{13}$C-NMR and MS are compatible with the structure.

Example 2.3: Preparation of Compounds 12d-e. General Procedure

The ligands 11d-e (1 eq) were suspended in H$_2$O (concentration 5% w/v; at pH 1-2), and dissolved at pH 6.5-7 by addition of 2N NaOH. A titrated solution of GdCl$_3$ (1 eq) was added in portions. The mixture was stirred at room temperature and pH was kept constant by addition of 0.1N NaOH. The reaction solution was concentrated to obtain precipitation; complexes 12d-e were isolated by filtration.

Example 2.3d: Preparation of Compound 12d

[(6-[Bis[(carboxymethyl)amino]-6-[5-(didecylamino)-5-oxopent-1-yl]-tetrahydro-1H-1,4-diazepine-1,4(5H)-diacetate[4-)]gadolinate(1-)]sodium Reagents: Compound 11d (1.1 g; 1:48 mmol);
Compound 12d (1.12 g; 1.24 mmol); Yield 90%.
Analytical data:
HPLC-ELSD: 94.6% (area %)
Mr: 903.20 (C38H66GdN4NaO9)
MS is compatible with the structure.

Example 2.3e: Preparation of Compound 12e

[[6-[Bis[(carboxymethyl)amino]-6-[5-(dodecylamino)-5-oxopent-1-yl]-tetrahydro-1H-1,4-diazepine-1,4(5H)-diacetate(4-)]gadolinate(1-)]sodium Reagents: Compound 11e (1.10 g, 1.37 mmol);
Compound 12e (1.02 g; 1.06 mmol); Yield: 78%.
Analytical data:
HPLC-ELSD: 94.3% (area %)
Mr: 959.31 (C42H74GdN4NaO9).
MS is compatible with the structure.

Example 3: Preparation of Compound 21

6-[Bis[2-[(1,1-dimethyl)ethoxy]-2-oxoethyl]amino]-6-[(1R,4R)-4-carboxycyclohexane-1-yl]tetrahydro-1H-1,4-diazepine-1,4(5H)-diacetic acid bis[(1,1-dimethyl)ethyl]ester The compound 21 was prepared according to the scheme 5:

Schema 5

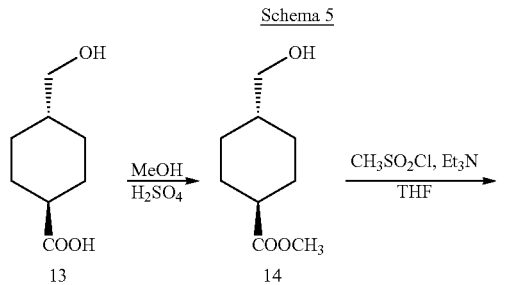

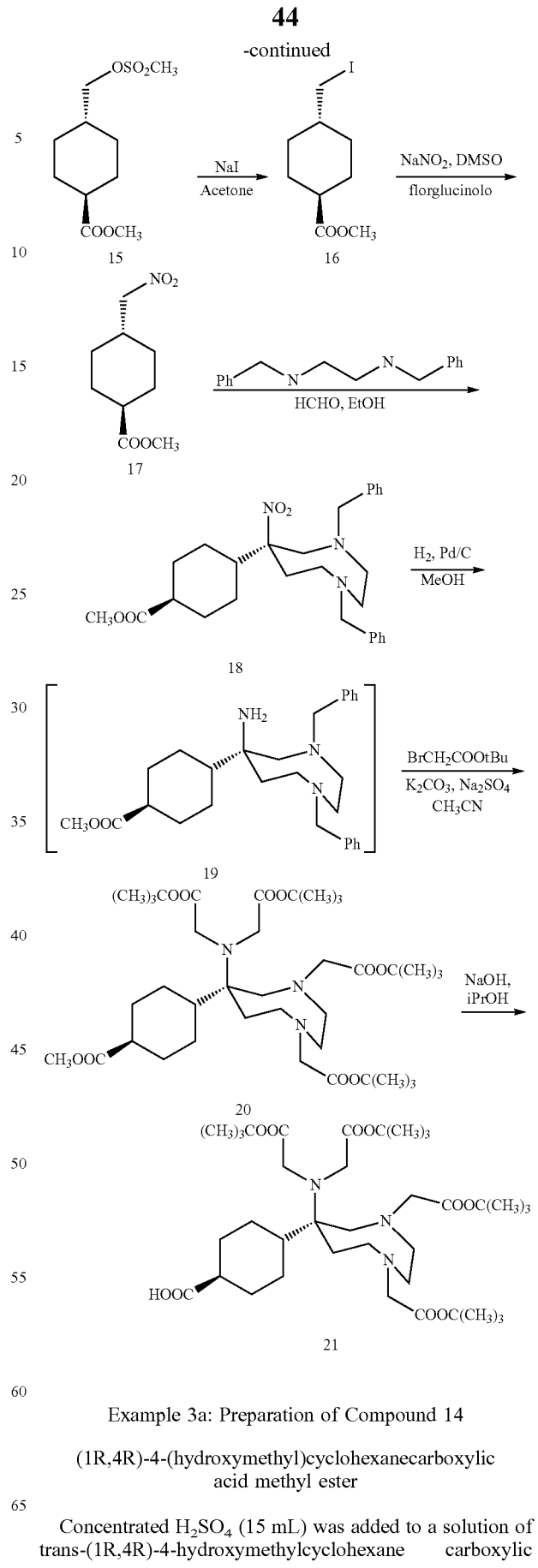

Example 3a: Preparation of Compound 14

(1R,4R)-4-(hydroxymethyl)cyclohexanecarboxylic acid methyl ester

Concentrated H$_2$SO$_4$ (15 mL) was added to a solution of trans-(1R,4R)-4-hydroxymethylcyclohexane carboxylic acid 13 (15 g; 94.8 mmol) in MeOH (300 mL) then the reaction mixture was stirred and refluxed for 4 h. The solution was concentrated and then basified by addition of NH$_4$OH aqueous solution; the white solid was filtered off and the mother liquor was extracted with EtOAc (3×70 mL). The combined organic layers were washed with saturated NaCl aqueous solution, dried (Na$_2$SO$_4$) and evaporated at reduced pressure to give 14 as a yellow liquid (17.26 g) that was employed in the following reaction without further purification.
Quantitative yield.
Analytical data:
Mr: 172.22 (C9H16O3)
$^1$H- and $^{13}$C-NMR and MS are compatible with the structure.

Example 3b: Preparation of Compound 15

(1R,4R)-4-(methylsulfonyloxy)methyl]cyclohexanecarboxylic acid methyl ester

To a solution of compound 14 (17.26 g) in THF (450 mL) cooled at 0° C. triethylamine (39.4 mL; 284.5 mmol) was added followed by methanesulfonyl chloride (14.9 mL; 151.7 mmol). The mixture was stirred at 0° C. for additional 10 min then the reaction mixture was stirred at room temperature for 2 h. The reaction mixture was filtered through a Celite (0.01-0.04 mm) bed that was then washed with fresh THF. The resulting solution was evaporated under reduced pressure to give compound 15 as a yellow oil (30.95 g) that was employed in the following reaction without further purification.
Quantitative yield.
Analytical data:
Mr: 250.30 (C10H18O5S)
$^1$H- and $^{13}$C-NMR and MS are compatible with the structure.

Example 3c: Preparation of Compound 16

(1R,4R)-4-(Iodomethyl)cyclohexanecarboxylic acid methyl ester

A solution of compound 15 (30.95 g) and sodium iodide (42.64 g; 284.5 mmol) in acetone (450 mL) was stirred at room temperature for 2 h then refluxed for 3.5 h. After 60 h at room temperature additional NaI (5 g; 17.7 mmol) was added and the solution was refluxed for further 7 hours. The solvent was evaporated under reduced pressure and the yellow residue was treated with diethyl ether; the insoluble salts were filtered off and washed with fresh diethyl ether. The ether solution was evaporated and the crude product was purified by flash chromatography to give compound 16 as a yellow liquid (22.43 g; 79.5 mmol).
Yield: 84%
Analytical data:
Mr: 282.12 (C9H15IO2)
$^1$H- and $^{13}$C-NMR and MS are compatible with the structure Example 3d: Preparation of Compound 17

(1R,4R)-4-(Nitromethyl)cyclohexanecarboxylic acid methyl ester

Compound 16 (21.92 g; 77.7 mmol) was added to a solution of sodium nitrite (10.72 g; 155.4 mmol) and phloroglucinol (10.78 g; 85.4 mmol) in DMSO (1 L) The solution was stirred at room temperature under N$_2$ atmosphere for 48 h. The reaction mixture was diluted with H$_2$O (3 L) and extracted with Et$_2$O. The organic layer was dried (Na$_2$SO$_4$) and evaporated to give a crude product that was purified by flash chromatography. The compound 17 (10.35 g; 51.4 mmol) was obtained as a pale yellow liquid.
Yield: 66%
Analytical data:
HPLC: 97.9% (HPLC Area %)
Mr: 201.22 (C9H15NO4)
$^1$H- and $^{13}$C-NMR and MS are compatible with the structure Example 3e: Preparation of Compound 18

6-[(1R,4R)-4-(methoxycarbonyl)cyclohexane-1-yl]-6-nitro-1,4-bis(phenylmethyl)-tetrahydro-1H-1,4-diazepine A suspension of N,N'-dibenzylethylenediamine diacetate (18.29 g; 50.7 mmol) in EtOH (400 mL) was stirred at 60° C. until a clear solution was obtained; paraformaldehyde (4.57 g; 152.2 mmol) was added and the suspension was heated at 80° C. for 1.5 h to give a dark orange clear solution. A solution of compound 17 (10.21 g; 50.7 mmol) in EtOH was added dropwise and the final solution was stirred at 80° C. for 6 h. After 15 h at room temperature, the resulting precipitate was filtered, washed with EtOH and dried under vacuum to give compound 18 as a white solid material (17.88 g; 38.4 mmol).
Yield: 76%.
Analytical data:
HPLC: 99.61% (area %)
Mr: 465.59 (C27H35N3O4)
$^1$H- and $^{13}$C-NMR and MS are compatible with the structure.

Example 3f: Preparation of Compound 19

6-Amino-4-(methoxycarbonyl)cyclohexane-1-yl] tetrahydro-1H-1,4-diazepine

A suspension of compound 18 (17.88 g; 38.4 mmol) in THF (200 mL) was stirred at 40° C. until a clear solution was obtained; the solution was then diluted with MeOH (150 mL). A suspension of 5% Pd/C (10.66 g) in MeOH (50 mL) was added and the mixture was hydrogenated at 40° C. for 11 h at ambient pressure. The catalyst was removed by filtration and the solution was evaporated to give compound 19 as a greenish oil (9.57 g; 37.4 mmol). The product obtained was used without further purification.
Yield: 98%.
Analytical data:
Mr: 255.36 (C13H25N3O2)
$^1$H- and $^{13}$C-NMR and MS are compatible with the structure Example 3g: Preparation of Compound 20

6-[Bis[2-[(1,1-dimethyl)ethoxy]-2-oxoethyl]amino]-6-[(1R,4R)-4-(methoxycarbonyl)-cyclohexane-1-yl] tetrahydro-1H-1,4-diazepine-1,4(5H)-diacetic acid bis[(1,1-dimethyl)ethyl]ester The compound 19 (9.52 g; 37.3 mmol) was dissolved in CH$_3$CN (400 mL), then K$_2$CO$_3$ (23.19 g; 167.8 mmol) and Na₂SO₄ (15.88 g; 111.8 mmol) were added. Subsequently, t-butyl bromoacetate (24.6 mL; 167.8 mmol) was added and the mixture was stirred at 80° C. for 16 h. The salts were filtered off, and the filtrate was evaporated to residue that was dissolved in EtOAc (200 mL) and the solution washed with H₂O (3×70 mL) and NaCl saturated aqueous solution (70 mL). The organic phase was dried (Na₂SO₄), filtered and evaporated. The crude product (27.36 g) was purified by flash chromatography to give the compound 20 as a pale yellow oil (5.34 g; 7.5 mmol).

Yield: 20%

Analytical data:

Mr: 711.93 (C37H65N3O10)

¹H- and ¹³C-NMR and MS are compatible with the structure

Example 3h: Preparation of Compound 21

6-[Bis[2-[(1,1-dimethyl)ethoxy]-2-oxoethyl]amino]-6-[(1R,4R)-4-carboxy-cyclohexane-1-yl]tetrahydro-1H-1,4-diazepine-1,4(5H)-diacetic acid bis[(1,1-dimethyl)ethyl]ester 2N NaOH (7.12 mL; 14.2 mmol) was added to a solution of compound 20 in i-PrOH (100 mL) stirred at room temperature and then H₂O (5.5 mL) was added until a homogenous mixture was obtained. The solution was stirred for 5.5 h at room temperature, as the reaction was not completed, the solution was stored at −20° C. for 15 h. The temperature was allowed to raise to room temperature and the reaction mixture was stirred for further 3 h. The pH was corrected to 7 with 2N HCl (7.12 mL) and the solution was evaporated under reduced pressure at room temperature. The residue was resuspended in H₂O (80 mL), acidified with 2N HCl (7.12 mL) and extracted with EtOAc. The organic layer was dried (Na₂SO₄) and evaporated to give compound 21 as a white solid (4.5 g; 6.45 mmol).

Yield: 90%.

Analytical data:

Mr: 697.91 (C36H63N3O10).

¹H- and ¹³C-NMR and MS are compatible with the structure.

Example 4: Preparation of Compounds 25a-c

Compounds 25a-c were prepared according to the Scheme 6:

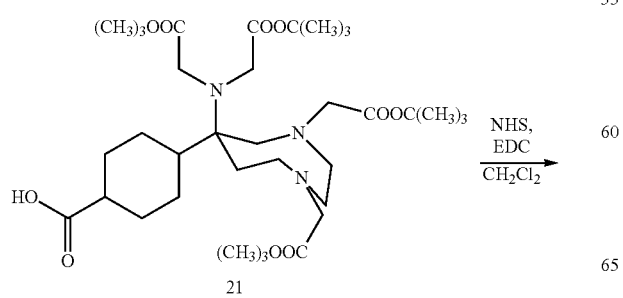

Schema 6

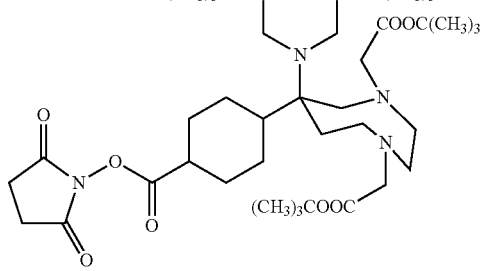

22

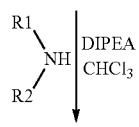

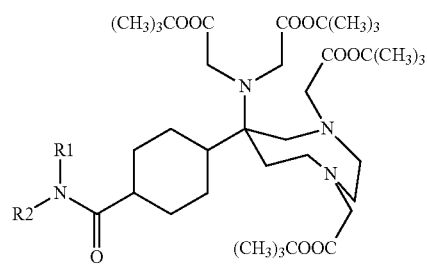

23a-c

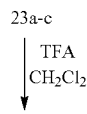

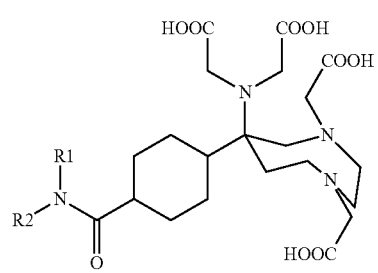

24a-c

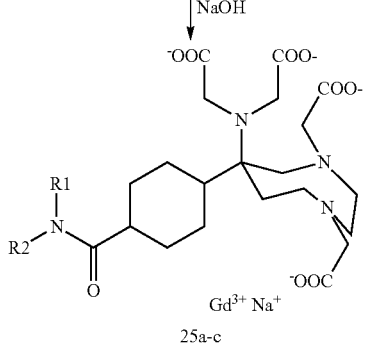

25a-c

-continued a: $R_1 = R_2 = CH_3(CH_2)_9$
c: $R_1 = H$

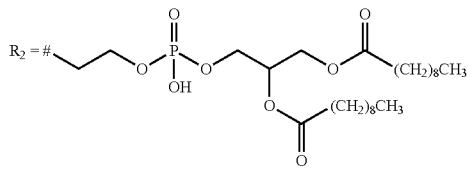

Example 4.1: Preparation of Compound 22

6-[Bis[2-[(1,1-dimethyl)ethoxy]-2-oxoethyl]amino]-6-[(1R,4R)-4-[[(2,5-dioxopirrolidin-1-yl)oxy]carbonyl]cyclohexane-1-yl]tetrahydro-1H-1,4-diazepine-1,4(5H)-diacetic acid bis[(1,1-dimethyl)ethyl]ester NHS (0.27 g; 2.3 mmol) was added to a solution of compound 21 (1.09 g; 1.6 mmol) in $CH_2Cl_2$ (50 mL) stirred at 0° C., then a solution of EDC (0.45 g; 2.3 mmol) in $CH_2Cl_2$ (50 mL) was added dropwise. The reaction mixture was stirred at room temperature for 49 h. The final solution was washed with $H_2O$ (3×40 mL) and the organic layer was dried ($Na_2SO_4$) and evaporated to give 22 as a solid (1.35 g) that was used in the next step without further purification. Quantitative yield.

Example 4.2: Preparation of Compounds 25a-c. General Procedure

The selected amine (1-1.3 eq) was added to a solution of compound 22 (1 eq) in $CHCl_3$ (concentration 2%) followed by addition of DIPEA (1.7 eq) The mixture was stirred at room temperature for 64-72 h. As the reaction solution became neutral, additional DIPEA (1.7 eq) was added and the reaction mixture was stirred at room temperature for further 2-21 h. The reaction mixture was then washed subsequently with $H_2O$ (35 mL), with diluted HCl until pH of washing was acid (3×40 mL) and with $H_2O$ (35 mL) The organic phase was dried ($Na_2SO_4$) and evaporated to give a viscous yellowish crude that was purified by flash chromatography to give compound 23 a-c as a yellow oil, according to the following data:

Example 4.2a: Preparation of Compound 23a

6-[Bis[2-[(1,1-dimethyl)ethoxy]-2-oxoethyl]amino]-6-[(1R,4R)-4-[(didecylamino)-carbonyl]cyclohexane-1-yl]tetrahydro-1H-1,4-diazepine-1,4(5H)-diacetic acid bis[(1,1-dimethyl)ethyl]ester Reagents: Compound 22 (1.18 g; 1:48 mmol) didecylamine (0.44 g; 1.48 mmol)
Compound 23a (075 g, 0.77 mmol). Yield: 52%.
Mr: 977.46 (C56H104N4O9)
$^1H$- and $^{13}C$-NMR and MS are compatible with the structure.

Example 4.2c: Preparation of Compound 23c

6-[Bis[2-[(1,1-dimethyl)ethoxy]-2-oxoethyl]amino]-6-[(1R,4R)-4-[[[(7R)-4-hydroxy-4-oxido-10-oxido-10-oxo-7-[(1-oxodecyl)oxy]-3,5,9-trioxa-4-phosphanonadec-1-yl]amino]carbonyl]cyclohexane-1-yl]tetrahydro-1H-1,4-diazepine-1,4(5H)-diacetic acid bis [(1,1-dimethyl)ethyl]ester Reagents: Compound 22 (1.35 g; 1.56 mmol); 1,2-didecanoyl-sn-glycero-3-phosphoethanolamine (0.81 g; 1.56 mmol)

Compound 23c (0.84 g; 0.70 mmol). Yield: 45%.
Mr: 1203.54 (C61H111N4O17P)
$^1H$- and $^{13}C$-NMR and MS are compatible with the structure.

Example 4.3: Preparation of Compounds 24a-c. General Procedure

TFA (6 eq) was added dropwise to a solution of compound 23a or 23c (1 eq) in $CH_2Cl_2$ (50 mL) stirred at 0° C. The reaction mixture was stirred for 1 hour at room temperature then evaporated to residue that was dissolved with fresh TFA (350 eq); the solution was then stirred at room temperature for 24-28 h. TFA was evaporated and the residue was treated with $iPr_2O$ (40-60 mL) to give a white solid that was isolated by centrifugation and dried (at reduced pressure and at 30° C. in the presence of NaOH pellets) to give compound 24a-c according to the following data:

Example 4.3a: Preparation of Compound 24a

6-[[Bis(carboxymethyl)]amino]-6-[(1R,4R)-4-[(didecylamino)carbonyl]cyclohexane-1-yl]tetrahydro-1H-1,4-diazepine-1,4(5H)diacetic acid Reagents: Compound 23a (0.75 g, 0.77 mmol)
Compound 24a (0.41 g; 0.54 mmol) Yield: 70%.
Analytical data:
HPLC-ELSD: 94.1% (% area)
Mr: 753.03 (C40H72N4O9)
Complexometric titer: (0.001 M GdCl3): 81.7%
$^1H$- and $^{13}C$-NMR and MS are compatible with the structure.

Esempio 4.3c: Preparation of Compound 24c

6-[[Bis(carboxymethyl)]amino]-6-[[[(7R)-4-hydroxy-4-oxido-10-oxo-7-[(1-oxodecyl)oxy]-3,5,9-trioxa-4-phosphanonadec-1-yl]amino]carbonyl]cyclohexane-1-yl]tetrahydro-1H-1,4-diazepine-1,4 (5H)-diacetic acid Reagents: Compound 23c (0.84 g, 0.70 mmol)
Compound 24c (0.67 g; 0.69 mmol); Yield: 98%.
Analytical data:
HPLC-ELSD: 96.2% Area %)
Mr: 979.11 (C45H79N4O17P)
Complexometric titer: (0.001 M GdCl3): 96.9%
$^1H$- and $^{13}C$-NMR and MS are compatible with the structure.

Example 4.4: Preparation of Compounds 25a-c. General Procedure

The titrated compounds were prepared according to the procedures described in example 2.3.

Example 4.4a: Preparation of Compound 25a

[[6-[[Bis(carboxymethyl)]amino]-6-[(1R,4R)-4-(didecylamino)carbonyl]cyclohexane-1-yl]tetrahydro-1H-1,4-diazepine-1,4(5H)-diacetate(4-)]gadolinate(1-)]sodium Reagents: Compound 24a (0.32 g, 0.43 mmol)
Compound 25a (0.33 g; 0.35 mmol) Yield: 83%.

Analytical data:
HPLC-ELSD: 95.2% (area %)
Mr: 929.24 (C40H68GdN4NaO9)
TGA: 5.7%
MS is compatible with the structure.

Example 4.4c: Preparation of Compound 25c

[[6-[[Bis(carboxymethyl)]amino]-6-[(1R,4R)-4-[[(7R)-4-hydroxy-4-oxido-10-oxo-7-[(1-oxodecyl)oxy]-3,5,9-trioxa-4-phosphanonadec-1-yl]amino]carbonyl]cyclohexane-1-yl]tetrahydro-1H-1,4-diazepine-1,4(5H)-diacetate(4-)]gadolinate(1-)] sodium Reagents: Compound 24c (0.35 g, mmol 0.36)
Compound 25c (0.31 g; 0.27 mmol) Yield: 77%
Analytical data:
Mr: 1155.32 (C45H75GdN4 NaO17P)
MS is compatible with the structure.

Preparation of Formula (II) Compounds

Example 5: Preparation of [10-[2-(didecylamino)-2-oxoethyl]-1,4,7,10-tetraazacyclododecane-1,4,7-triacetate(3-)]gadolinium (29)

room temperature for 30 min; didecylamine was added (2.32 g; 7.8 mmol) and the mixture was kept under stirring at room temperature for 24 h.

The reaction mixture was evaporated and the residue was dissolved in CHCl$_3$ and washed sequentially with H$_2$O (100 mL), acidified H$_2$O (pH 4-5 with HCl; 100 mL) and H$_2$O (100 mL). The organic layer was dried (Na$_2$SO$_4$), filtered and evaporated, and the resulting crude material was purified by flash chromatography to obtain compound 27 as a colorless oil (5.36 g; 7.24 mmol). Yield 93%.
Analytical data
HPLC-ELSD: 96.9% (area %)
Mr: 740.08 (C40H77N5O7)
$^1$H- and $^{13}$C-NMR and MS are compatible with the structure Example 5.b: Preparation of 10-[2-(didecylamino)-2-oxoethyl]-1,4,7,10-tetraazacyclododecane-1,4,7-triacetic acid (28)

TFA (6 eq) was added dropwise to a solution of compound 27 (5.02 g; 5.89 mmol) in CH$_2$Cl$_2$ (100 mL) cooled to 0° C.; the resulting solution was stirred at room temperature for 1 h and then evaporated. The residue was dissolved in fresh TFA (50 eq) and the so-obtained solution was kept under stirring at room temperature for 96 h.

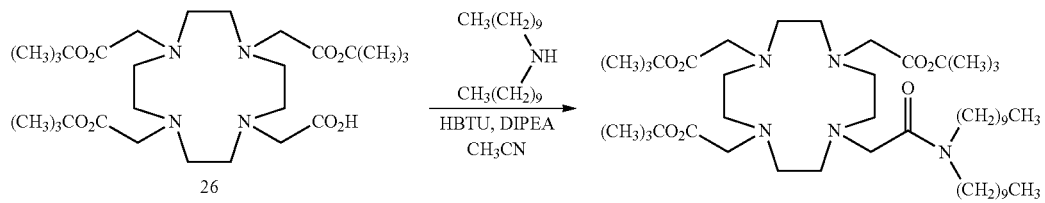

Schema 7

Example 5.a: Preparation of 10-[2-(didecylamino)-2-oxoethyl]-1,4,7,10-tetraazacyclododecane-1,4,7-triacetic acid tris [(1,1-dimethyl)ethyl]ester (27)

HBTU (g; mmol) and DIPEA (g; mmol) were sequentially added to a suspension of compound 26 (5 g; 7.8 mmol) in CH$_3$CN (500 mL) and the mixture was left under stirring at The reaction mixture was evaporated and the residue was treated with iPr$_2$O (150 mL) to give a white solid material which was centrifuged, washed with iPr$_2$O (2×40 mL). Such solid was resuspended in H$_2$O, dissolved at pH 6-7 by addition of 1M NaOH and the so-obtained solution was purified by percolation of Amberlite® XAD1600 resin using a H$_2$O/CH$_3$CN gradient as eluent. The fractions containing the desired product were combined and lyophilized to obtain the ligand 28 as a white solid material (2.04 g; 2.99 mmol). Yield 51%.

Analytical data
HPLC-ELSD: 99.5% (area %)
Mr: 683.97 (C36H69N5O7)
Complexometric titer (0.01 M ZnSO4): 98.8%
$^1$H- and $^{13}$C-NMR and MS are compatible with the structure Example 5.c: Preparation of [10-[2-(didecylamino)-2-oxoethyl]-1,4,7,10-tetraazacyclododecane-1,4,7-triacetate(3-)]gadolinium (29)

A solution of 0.1 M GdCl$_3$ (14.5 mL; 1.45 mmol) was added in portions to a solution of ligand 28 (1.01 g; 1.45 mmol) in H$_2$O (50 mL) at pH 5-6 and the solution was kept under stirring at room temperature, maintaining the pH between 6.5 and 7.5 by addition of 0.1 M NaOH. The solution was desalted by elution on Amberlite® XAD1600 resin using a H$_2$O/CH$_3$CN gradient as eluent. Fractions containing the desired product were combined and lyophilized to obtain complex 29 as a white solid material (1.08 g; 1.29 mmol). Yield 89%.

Analytical data
HPLC-ELSD: 99.0% (area %)
Mr: 838.20 (C36H66GdN5O7)
MS is compatible with the structure Example 6: Preparation of Complexes 32a-b Schema 8

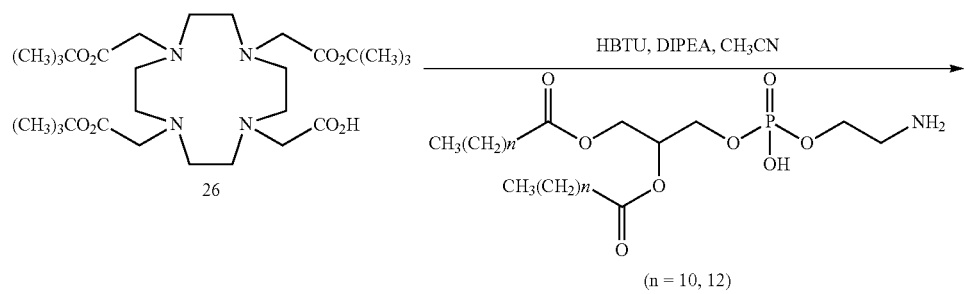

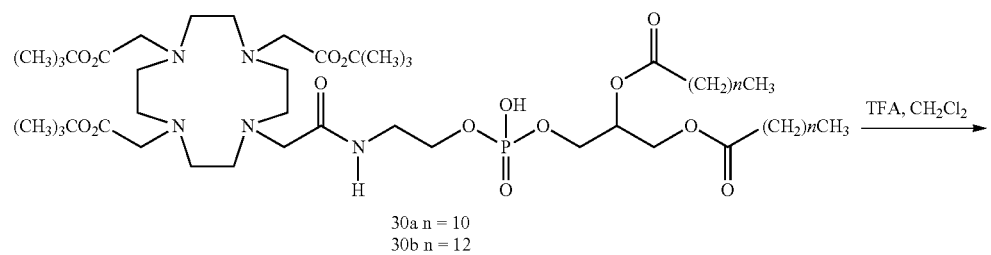

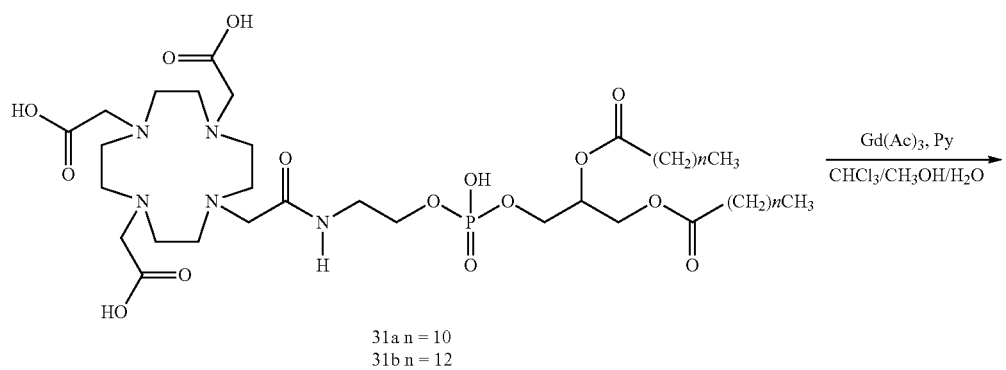

-continued

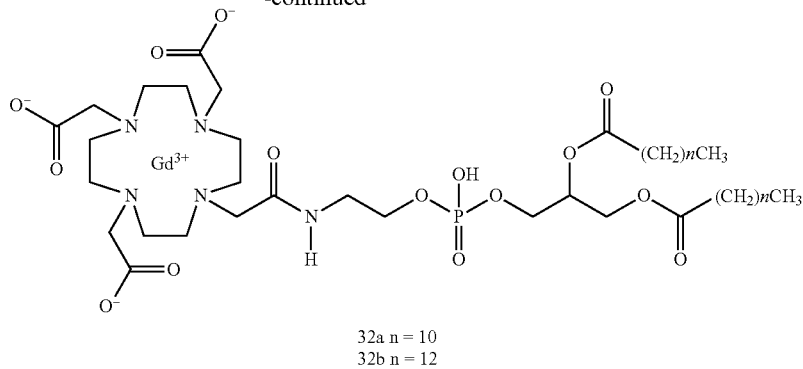

32a n = 10
32b n = 12

Example 6.1 Preparation of Compounds 30a-b—General Procedure

HBTU (1 eq) and DIPEA (1.7 eq) were sequentially added to a suspension of compound 26 in CH$_2$Cl$_2$ (concentration 1% w/v) and the mixture was kept under stirring at room temperature for 30 min; phosphoethanolamine (DLPE n=10 or DMPE n=12) (1 eq) was then added and the mixture was maintained under stirring at room temperature for 24 h. The reaction mixture was sequentially washed with H$_2$O (100 mL), acidified H$_2$O (pH 4-5 with HCl; 100 mL) and H$_2$O (100 mL). The organic layer was dried (Na$_2$SO$_4$), filtered and evaporated, and the so-obtained crude material was purified by flash chromatography to obtain compounds 30a-b.

Example 6.1a Preparation of 10-[(10R)-7-hydroxy-7-oxido-2,13-dioxo-10-[(1-oxododecyl)oxy]-6,8,12-trioxa-3-aza-7-phosphatetracos-1-yl]-1,4,7,10-tetraazacyclododecane-1,4,7-triacetic acid tris [(1,1-dimethyl)ethyl]ester 30a Reagents: Compound 26 (968 mg; 1.69 mmol); 1,2-didodecanoyl-sn-glycero-3-phosphoethanolamine (980 mg; 1.69 mmol).
Compound 30a (605 mg, 0.53 mmol); Yield 32%.
Analytical data
HPLC-ELSD: 40.6% (area %)
Mr: 1134.48 (C57H108N5O15P)
$^1$H- and $^{13}$C-NMR and MS are compatible with the structure.

Example 6.1b Preparation of 10-[(10R)-7-hydroxy-7-oxido-2,13-dioxo-10-[(1-oxotetradecyl)oxy-6,8,12-trioxa-3-aza-7-phosphaesacos-1-yl]-1,4,7,10-tetraazacyclododecane-1,4,7-triacetic acid tris[(1,1-dimethyl)ethyl]ester 30b Reagents: Compound 26 (1.43 g; 2.36 mmol), 1,2-ditetradecanoyl-sn-glycero-3-phosphoethanolamine (1.50 g; 2.36 mmol).
Compound 30b (2.18 g, 1.97 mmol). Yield 78%.
Analytical data
HPLC-ELSD: 82.4% (area %)
Mr: 1190.49 (C61H116N5O15P)
$^1$H- and $^{13}$C-NMR and MS are compatible with the structure.

Example 6.2 Preparation of Compounds 31a-b—General Procedure

TFA (6 eq) was added dropwise to a solution of compounds 30a-b in CH$_2$Cl$_2$ (concentration 1% w/v) cooled to 0° C. and the solution was stirred at room temperature for 1 h and then evaporated. The residue was dissolved in fresh TFA (30 eq) and the new solution was kept under stirring at room temperature for 96 h.

The reaction mixture was evaporated and the residue was treated with iPr$_2$O (150 mL) to yield a white solid material which was centrifuged and washed with iPr$_2$O (2×40 mL).

The crude product 31a was purified according to the following method. The crude product was suspended in H$_2$O and dissolved at pH 6-7 by addition of 5% aq. NaHCO$_3$ and subsequently re-precipitated at pH 3 by addition of 1M HCl. The so-obtained solid material was centrifuged and dried to obtain ligand 31a.

The crude product 31b was purified according to the following method. The crude product was suspended in H$_2$O, dissolved at pH 6-7 by addition of 1M NaOH and the so-obtained solution was purified by percolation on Amberlite® XAD1600 resin using a H$_2$O/CH$_3$CN gradient as eluent. Fractions containing the desired product were combined and lyophilized to obtain ligand 31b.

Example 6.2a Preparation of 10-[(10R)-7-hydroxy-7-oxido-2,13-dioxo-10-[(1-oxododecyl)oxy]-6,8,12-trioxa-3-aza-7-phosphatetracos-1-yl]-1,4,7,10-tetraazacyclododecane-1,4,7-triacetic acid (31a)

Reagents: Compound 30a (600 mg, 0.53 mmol)
Compound 31a (501 mg, 0.53 mmol). Yield 98%.
Analytical data
HPLC-ELSD: 61.3% (area %)
Mr: 966.16 (C45H84N5O15P)
$^1$H- and $^{13}$C-NMR and MS are compatible with the structure Example 6.2b Preparation of 10-[(10R)-7-hydroxy-7-oxido-2,13-dioxo-10-[(1-oxotetradecyl)oxy]-6,8,12-trioxa-3-aza-7-phosphaesacos-1-yl]-1,4,7,10-tetraazacyclododecane-1,4,7-triacetic acid (31b)

Reagents: Compound 30b (2.0 g, 1.68 mmol)
Compound 31b (1.1 g; 1.07 mmol). Yield 63%.
Analytical data
HPLC-ELSD: 99.9% (area %)
Mr: 1022.26 (C49H92N5O15P)

¹H- and ¹³C-NMR and MS are compatible with the structure

Example 6.3 Preparation of Compounds 32a-b—General Procedure

Pyridine (until neutralization) and a solution of $Gd(Ac)_3$ in $CH_3OH/H_2O$ 10:1 (1 eq) were added in portions to a suspension of ligands 31a-b in $CHCl_3$ (concentration 1% w/v) stirred at room temperature. The reaction mixture was evaporated and the residue was treated with $CH_3OH$/Toluene (3×50 mL) and $CHCl_3$ (3×50 mL) by evaporating to dryness after each solubilization. The final residue was suspended in $H_2O$ and lyophilized to obtain complexes 32a-b as white solid material.

Example 6.3a Preparation of [10-[(10R)-7-hydroxy-7-oxido-2,13-dioxo-10-[(1-oxododecyl)oxy]-6,8,12-trioxa-3-aza-7-phosphatetracos-1-yl]-1,4,7,10-tetraazacyclododecane-1,4,7-triacetate(3-)]gadolinium (32a)

Reagents: Compound 31a (423 mg, 0.44 mmol)
Compound 32a (472 mg, 0.42 mmol). Yield 96%

Analytical data
HPLC-ELSD: 69.5% (area %)
Mr: 1120.38 (C45H81GdN5O15P)
MS is compatible with the structure

Example 6.3b Preparation of [10-[(10R)-7-hydroxy-7-oxido-2,13-dioxo-10-[(1-oxotetradecyl)oxy]-6,8,12-trioxa-3-aza-7-phosphaesacos-1-yl]-1,4,7,10-tetraazacyclododecane-1,4,7-triacetate(3-)] gadolinium (32b)

Reagents: Compound 31b (900 mg, 0.85 mmol)
Compound 32b (991 mg, 0.84 mmol). Yield 99%.
Analytical data
HPLC-ELSD: 92.8% (area %)
Mr: 1176.49 (C49H89GdN5O15P)
MS is compatible with the structure

Example 7: Preparation of Complexes 37a-b

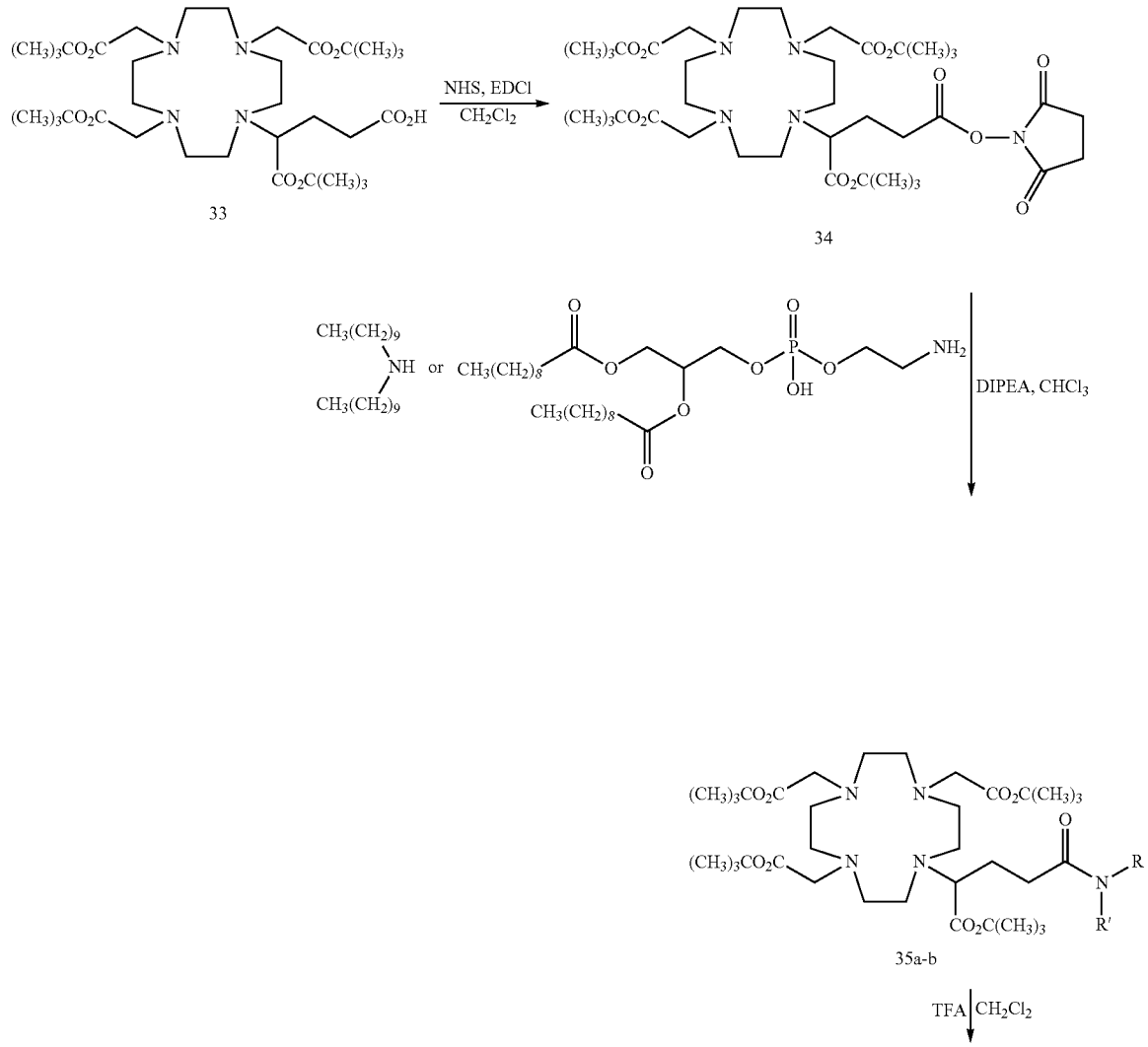

Schema 9

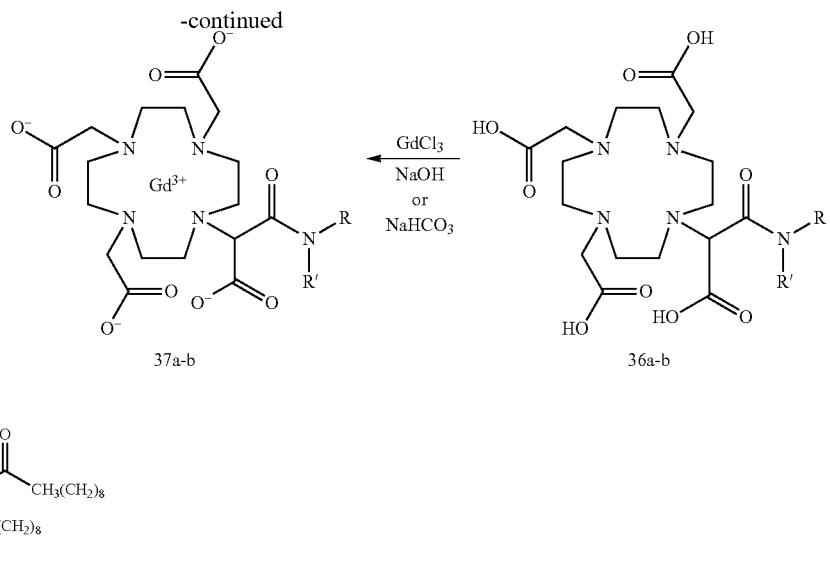

a R = R' = (CH₂)₉CH₃
b R = H

Compound 33, used as an initial reactant for the synthesis of metal complexes 37a-b, was synthesized according to a procedure known to the state of the art (Org. Process. Res Dev. 2009, 13(3), 535-542.

Example 7.1: Preparation of 10-[(4R)-7-(2,5-dioxo-1-pyrrolidinyl)oxy-2,2-dimethyl-3,7-dioxo-2-oxyept-4-yl]-1,4,7,10-tetraazacyclododecane-1,4,7-triacetic acid tris [(1,1-dimethyl)ethyl]ester (34)

A EDC solution (0.757 g; 3.95 mmol) in CH₂Cl₂ (30 mL) was added dropwise to a solution of compound 33 (2 g; 2.63 mmol) and NHS (0.455 g; 3.95 mmol) in CH₂Cl₂ (50 mL) cooled to 0° C., the reaction mixture was kept under stirring at room temperature for 20 h. The mixture was then washed with H₂O (3×60 mL) (until neutralization), dried (Na₂SO₄) and evaporated to give compound 34 (1.78 g; 2.22 mmol). Yield 84%.

Analytical data
Mr: 797.98 (C39H67N5O12)
¹H- and ¹³C-NMR and MS are compatible with the structure Example 7.2a: Preparation of 10-[(1S)-1-[[(1,1-dimethyl)ethoxy]carbonyl]-4-oxo-4-(didecylamino)but-1-yl]-1,4,7,10-tetraazacyclododecane-1,4,7-triacetic acid tris [(1,1-dimethyl)ethyl]ester (35a)

Didecylamine (0.665 g; 2.23 mmol) and DIPEA (646 microL; 3.79 mmol) were sequentially added to a solution of compound 34 (1.78 g; 2.23 mmol) in CHCl₃ (70 mL) and the solution was kept under stirring at room temperature for 72 h. The reaction mixture was sequentially washed with H₂O (1×50 mL), acidic H₂O (pH 4-5 with HCl, 1×50 mL) and H₂O (1×50 mL), dried (Na₂SO₄) and evaporated to obtain compound 35a (2.27 g; 2.23 mmol). Quantitative yield.

Analytical data
Mr: 980.46 (C55H105N5O9)
¹H- and ¹³C-NMR and MS are compatible with the structure Esempio 7.2b: Preparation of 10-[(1S)(12R)-1-[[(1,1-dimethyl)ethoxy]carbonyl]-9-hydroxy-9-oxido-4,15-dioxo-12-(1-oxodecyl)oxy]-8,10,14-trioxa-5-aza-9-phosphatetracos-1-yl]-1,4,7,10-tetraazacyclododecane-1,4,7-triacetic acid tris [(1,1-dimethyl)ethyl]ester (35b)

1,2-didecanoyl-sn-glycero-3-phosphoethanolamine (0.500 g; 0.955 mmol) and DIPEA [ ] (276 μL; 1.62 mmol) were sequentially added to a solution of compound 34 (0.762 g; 0.995 mmol) in CHCl₃ (25 mL) and the solution was kept under stirring at room temperature for 22 h. The reaction mixture was sequentially washed with H₂O (1×50 mL), acidic H₂O (pH 4-5 with HCl, 1×50 mL) and H₂O (1×50 mL), dried (Na₂SO₄) and evaporated, and the so-obtained crude residue was purified by flash chromatography to obtain compound 35b (0,725 g; 6.01 mmol). Yield 63%.

Analytical data
HPLC-ELSD: 79.7% (area %)
Mr: 1205.53 (C60H111N5O17P)
¹H- and ¹³C-NMR and MS are compatible with the structure Example 7.3 Preparation of Compounds 36a-b—General Procedure TFA (6 eq) was added dropwise to a solution of compounds 35a-b in CH₂Cl₂ (concentration 1% w/v) cooled to 0° C. and the solution was stirred at room temperature for 1 h and then evaporated. The residue was dissolved in fresh TFA (30 eq) and the resulting solution was kept under stirring at room temperature for 80-120 h. The reaction mixture was evaporated and the residue was treated with iPr₂O (80-100 mL) to give a white solid material which was centrifuged and washed with iPr₂O (2×30 mL). The crude compound 36a was purified by chromatography on Amberchrome® CG161 resin obtaining ligand 36a while the crude compound 36b was dried and used without further purification.

Example 7.3a: Preparation of 10-[(1S)-1-carboxy-4-oxo-4-(didecylamino)but-1-yl]-1,4,7,10-tetraazacyclododecane-1,4,7-triacetic acid (36a)

Reagents: Compound 35a (1.87 g, 1.91 mmol)
Compound 36a (688 mg, 0.91 mmol). Yield 48%.
Analytical data
HPLC-ELSD: 99.8% (area %)
Mr: 756.03 (C39H73N5O9)
$^1$H- and $^{13}$C-NMR and MS are compatible with the structure

Example 7.3b: Preparation of 10-[(1S)(12R)-1-carboxy-9-hydroxy-9-oxido-4,15-dioxo-12-(1-oxodecyl)oxy]-8,10,14-trioxa-5-aza-9-phosphatetracos-1-yl]-1,4,7,10-tetraazacyclododecane-1,4,7-triacetic acid (36b)

Reagents: Compound 35b (665 mg, 0.55 mmol)
Compound 36a (540 mg, 0.55 mmol). Quantitative yield
Analytical data
HPLC-ELSD: 99.8% (area %)
Mr: 981.10 (C44H79N5O17P)
$^1$H- and $^{13}$C-NMR and MS are compatible with the structure

Example 7.4 Preparation of Complexes 37a-b—General Procedure

Ligands 36a-b were suspended in H$_2$O and dissolved at pH 6-7 by addition of 2M NaOH (36a) or of 5% aq. NaHCO$_3$. (36b) then a solution of 0.1 M (1 eq) GdCl$_3$ was added in portions maintaining pH 7 by addition of 0.1M NaOH (36a) or of 5% aq. NaHCO$_3$ (36b). The crude complexes were obtained by freeze drying and were purified from salts by size exclusion chromatography on Sephadex® G10 resin to obtain complexes 37a-b.

Example 7.4 a Preparation of [[10-[(1S)-1-carboxy-4-oxo-4-(didecylamino)but-1-yl]-1,4,7,10-tetraazacyclododecane-1,4,7-triacetate(4-)]gadolinate(1-)] sodium. (37a)

Reagents: Compound 36a (400 mg, 0.529 mmol)
Compound 37a (326 mg, 035 mmol). Yield 66%.
Analytical data
HPLC-ELSD: 98.6% (area %)
Mr: 932.24 (C39H69GdN5NaO9)
MS is compatible with the structure

Example 7.4b: Preparation of [[10-[(1S)(12R)-1-carboxy-9-hydroxy-9-oxido-4,15-dioxo-12-(1-oxodecyl)oxy]-8,10,14-trioxa-5-aza-9-phosphatetracos-1-yl]-1,4,7,10-tetraazacyclododecane-1,4,7-triacetate(4-)]gadolinate(1-)]sodium 37b Reagents: Compound 36b (500 mg, 0.510 mmol)
Compound 37a (150 mg, 0.130 mmol). Yield 25%
Analytical data
HPLC-ELSD: 61.1% (area %)
Mr: 1158.32 (C44H76GdN5NaO17P)
MS is compatible with the structure.

Example 8.1 Preparation of pSLNs with Formula I Compound (9b) and DSPE-PEG-2000

An organic phase (O) was prepared by dissolving 200 mg of Epikuron 200® (Cargill Deutschland GmbH, Krefeld, Germany), 50 mg of [1,2-disteroyl-sn-glycero-3-phosphoethanolamine-N-(methoxy(polyethyleneglycol)-2000) ammonium salt DSPE-PEG-2000, 65 mg of complex 9b (titer 88%), 225 mg tripalmitin, 25 mg stearic acid in CH$_2$Cl$_2$. The organic phase was heated to 36° C. and kept under stirring until complete solubilization of the various components. An aqueous phase (W) containing 175 mg of sodium taurocholate, 0.2 mL of 1-butanol and 0.250 mL of water was added to the organic phase. The solution was stirred for 30 min at 36° C. until a stable and transparent microemulsion (W/O) was obtained (step c of the formulation process). Concurrently an aqueous solution W$_1$ containing 0.24% (weight/volume) Tween 80® (Serva, Heidelberg, Germany) was prepared and heated to 30° C. The microemulsion W/O was added dropwise to the aqueous phase W1 kept at 30° C. resulting in the multiple emulsion W/O/W$_1$ (step d of the formulation process). The organic solvent was then evaporated at atmospheric pressure maintaining the multiple emulsion under stirring for 45 min (step e). The temperature of the dispersion was then lowered to 10° C. to allow crystallization of the lipid core of pSLNs (step f). The so-obtained dispersion was then purified from the excess of emulsifier components by an ultrafiltration process by use of a regenerated cellulose membrane (Pellicon XL 30 kDa) and a solution of glucose 5.5% w/v. Finally the dispersion was concentrated to about 8 mL and filtered (0.22 μm filter). The amount of metal and phosphorus present in the final formulation was measured by ICP-MS (ELAN 6100 Perkin Elmer). The incorporation efficiency of the Gd(III) complex in the SLN was calculated as % Gd(III) weight in the final dispersion compared to the theoretical quantity. The characteristics of the dispersed particles, such as average hydrodynamic diameter (z-average) and the polydispersity index (PdI) were measured in PBS at a concentration of P=2 mM by DLS technique (Zetasizer Nano ZS, Malvern Instruments). The surface charge potential ζ-Potential) was always measured at a concentration of P=2 mM in a 5.5% glucose solution by ELS (Zetasizer Nano ZS, Malvern Instruments).

Moreover, the pSLN formulation was characterized for the relaxometric properties, according to the procedure described in Example 8.3. The relaxivity data in presence of albumin are reported in Table 3.

TABLE 1

Characterization of the pSLNs containing complex 9b.

| % incorporation efficiency | z-average (nm) | | PdI | | ζ-Potential (mV) | |
|---|---|---|---|---|---|---|
| | media | S.D. | media | S.D. | media | S.D. |
| 75 | 59.65 | 0.20 | 0.152 | 0.004 | −33.00 | 0.95 |

The P/Gd (III) ratio was calculated to be 6.22.

Example 8.2. pSLNs Preparation with Formula II Compound (B22286), DSPE-PEG-2000 and the Ligand 1,2-distearyl-sn-glycero-3-phosphoethanolamine-N-[folate (polyethylene glycol)-2000] ammonium salt (DSPE-PEG-2000-folate)

Synthesis of compound 622286 was described in MAGMA 2001.12 (2-3), 114-120). Its formula is reported herein below:

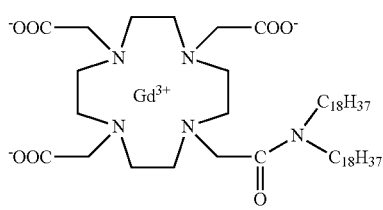

The complex was formulated in SLNs by using the same procedure described in example 8.1, replacing the complex 9b with an equivalent number of moles of 622286. The chemical-physical characterization of the dispersion was made as described in the previous example and the data are reported in Table 2.

TABLE 2

Characterization of the formulation containing B22286, DSPE-PEG2000 and DSPE-PEG2000-folate.

| % Incorporation efficiency | z-average (nm) media | S.D. | PdI media | S.D. | ζ-Potential media | S.D. |
|---|---|---|---|---|---|---|
| 75 | 56.60 | 0.34 | 0.160 | 0.007 | −23.61 | 0.60 |

The load of Gd(III) in pSLNs prepared with the derivative of formula II (B22286), DSPE-PEG-2000 was about 12000 molecular units of Gd complexes/particle. This value was obtained by measuring the volume fraction occupied by the particles (0%) by Turbiscan Lab Expert instrument.

The volume of a single particle ($V_p$) was calculated from the average diameter of the particle (50 nm) by approximating the volume of each particle to the volume of a perfect sphere. The number of np particles per cm³ was then derived from the relationship: $n_p = V_{tot}/V_p$,
(wherein $V_{tot}$ is the total volume occupied by the nanoparticles in one cm³ of formulation), from which the number of pSLNs/cm³ is estimated to be about $10^{14}$/cm³.

By deriving the number of molecules of the Gd(III) complex from the molar concentration it was possible to estimate that the number of molecules incorporated for each individual particle was about 12000 molecular units (payload).

The P/Gd (III) was calculated to be 5.13.

Example 8.3 Measurements of Relaxivity

Relaxivity measurements were performed using a Minispec instrumentation mq20 (Bruker Biospin, Germany). The $r_{1p}$ value for each complex incorporated in SLNs was determined from the measurement of T1 using the following equation:

$$R^i_{1obs} = 1/T^{i,j}_{1obs} = r^{i,j}_{1p} \cdot [Gd^{3+}] + 1/T^i_1$$

wherein $R^i_{1obs}$ is the relaxation time observed for the contrast agent formulated in SLNs, $T_{1obs}$ is the longitudinal relaxation time, while the indices i and j are respectively related to the incorporated contrast medium and to the medium. In detail, relaxivity measurements have been performed in presence of albumin (HSA4% in NaCl 0.9%) or human plasma (HP) at 20 MHz and 25° C. (pH 7.4).

TABLE 3

Relaxivity values $r_{1p}$ (mM$^{-1}$s$^{-1}$) of the amphiphilic complexes of Gd (III) of formula (I) incorporated in SLNs

| Incorporated complex | Incubation medium | Mean | S.D. |
|---|---|---|---|
| 9a | HSA 4% | 35.35 | 0.19 |
| 9b | HP | 40.99 | 0.34 |
| 9c | HP | 28.19 | 0.54 |
| 12d | HP | 40.31 | 0.67 |
|  | HSA 4% | 38.06 | 0.30 |
| 12e | HP | 39.37 | 0.39 |
| 25a | HSA 4% | 36.29 | 1.27 |
| 25c | HSA 4% | 34.95 | 0.24 |

TABLE 4

Relaxivity values $r_{1p}$ (mM$^{-1}$s$^{-1}$) of the amphiphilic complexes of Gd (III) of formula (II) incorporated in SLNs

| Incorporated complex | Incubation medium | Mean | S.D. |
|---|---|---|---|
| 29 | FBS | 25.9 | 0.15 |
| B22286 | HSA 4% | 30.19 | 0.63 |
| 37a | HSA 4% | 40.68 | 0.22 |
| 32a | HP | 19.54 | 0.11 |

Example 8.4. Physico-Chemical Characterization of pSLNs Formulations Containing Complexes of Formula (I) and of Formula (II)

Table 3 and 4 show examples of the physico-chemical characterization of formulations prepared as described in example 8.1 and 8.2. The efficiency of incorporation of Gd(III) complex in SLNs was calculated as % Gd(III) weight in the final dispersion compared to the theoretical quantity. The characteristics of the dispersed particles, such as the average hydrodynamic diameter (z-average) and the polydispersity index (PdI) are measured in PBS at a concentration of P=2 mM by using DLS technique (Zetasizer Nano ZS, Malvern Instruments). The surface charge potential (ζ-Potential) was always measured at a concentration of P=2 mM in a 5.5% glucose solution by ELS (Zetasizer Nano ZS, Malvern Instruments).

TABLE 5

Incorporation efficiency and Dynamic Light Scattering (DSC) characterization of particle distribution for pSLNs incorporating amphiphilic complexes of Gd (III) derivatives of formula (I).

| Incorporated complex | Incorpor. efficiency % | Z-average (nm) Media | S.D. | PdI Media | S.D. | ζ-Potential Media | S.D. |
|---|---|---|---|---|---|---|---|
| 12d | 70 | 63.71 | 1.12 | 0.16 | 0.020 | −31.43 | 1.16 |
| 12e | 65 | 49.90 | 0.43 | 0.12 | 0.002 | −31.51 | 1.18 |
| 9a | 50 | 67.75 | 1.28 | 0.263 | 0.005 | −35.65 | 0.77 |
| 9b | 75 | 59.65 | 0.20 | 0.152 | 0.004 | −33.00 | 0.95 |
| 9c | 81 | 69.45 | 1.17 | 0.172 | 0.012 | −30.48 | 0.81 |
| 25a | 82-75 | 55.79 | 0.80 | 0.179 | 0.001 | −31.02 | 2.39 |
| 25c | 55 | 64.51 | 0.03 | 0.274 | 0.002 | −34.16 | 0.45 |

TABLE 6

Incorporation efficiency and DLS characterization of
particle distribution for pSLNs incorporating amphiphilic complexes
of Gd(III) derivatives of Formula (II).

| Incorporated complex | % incorp. efficiency | Z-average | | PdI | | ζ-Potential (mV) | |
|---|---|---|---|---|---|---|---|
| | | mean | S.D. | mean | S.D. | mean | S.D. |
| 29 | 75 | 51.65 | 0.52 | 0.196 | 0.008 | −27.35 | 0.27 |
| B22286 | 80 | 52.78 | 0.16 | 0.141 | 0.011 | −27.81 | 0.36 |
| 37a | 75-80 | 56.63 | 0.91 | 0.207 | 0.004 | −37.40 | 0.54 |
| 32a | 60 | 60.48 | 0.01 | 0.150 | 0.020 | −26.30 | 0.26 |

Example 8.5. Calorimetric Measurements of pSLNs Incorporating complex 9b

Calorimetric studies were performed using a DSC 25 instrument (Mettler Toledo). In the experiment reported as an example, 30 mg of dispersion of pSLNs containing complex 9b were accurately weighed into a crucible of aluminium that was then hermetically closed. The sample was heated at a scan rate of 5° C./min from 25° C. to 85° C. and subsequently cooled at a rate of 1° C./min up to 25° C. Measurements were performed using a water containing crucible as reference. The same experiment was performed two months after the preparation of the formulation (stored at 4° C.) and no significant change was observed in the polymorphism of the crystalline core.

Example 9. MR Imaging with pSLNs

In vivo studies were performed using as tumor model human ovarian carcinoma (IGROV-1) implanted in the flank of Balb/C nu/nu mice. Images were acquired with a 7 Tesla MRI tomograph (Bruker Biospin, Germany). FIG. 4 shows the results obtained by intravenous administration of a pSLNs formulation prepared with complex B22286, used for comparison, at a dose of 50 μmol (Gd)/kg. It is possible to note the accumulation of pSLNs in tumor tissues detected by MRI 30 min after administration.

Example 10. In Vitro U937 Uptake of B22286 Loaded SLNs, B22286 Loaded Liposomes and Prohance®

Liposomes comprising B22286 were prepared using a thin-layer deposition/extrusion technique following the procedure described by Terreno et al. (Chemistry and Biodiversity, vol. 5, 2008: 1901-1912). The liposome formulation had the following composition: B22286 (15 mol %), POPC (59 mol %), cholesterol (23 mol %) and DSPE-Peg2000 (3 mol %). Cells of a Human leukemic monocyte lymphoma cell line (U937) were seeded (approx. 2×106/dish) in a 10 cm diameter Petri dishes with 10 mL of RPMI-1640 medium supplemented with 5% fetal bovine serum, 2 mM glutamine, 100 IU/mL penicillin and 100 μg/mL streptomycin. Differentiation to macrophages will be induced by the addition of TPA (20 ng/mL) and incubation over 48 h. Before further use, cells will be washed with 5 mL PBS and supplied with 3 mL of fresh RPMI-1640 medium supplemented with 5% fetal bovine serum, 2 mM glutamine, 100 IU/mL penicillin and 100 μg/mL streptomycin.

pSLNs prepared as described in the present invention (Example 8.1) and liposomes were incubated for 6 h at Gd(III) concentration of 0.15 mM. The same experiment was carried out using 1 mM of Prohance®. In each experiment, the medium was removed and cells were washed by PBS. Cell were lysed by sonication and mineralized in HCl 37% overnight at 120° C. for the determination of Gd(III) amount by measurement of the proton relaxation rate ($R_{1obs}$) of the solutions at 20 MHz (0.47 T) and at 25° C. on a PC 120 Minispec instrument (Bruker Biospin, Germany). The protein concentration of each sample was also determined from cell lysates by the Bradford method.

Figure 3:
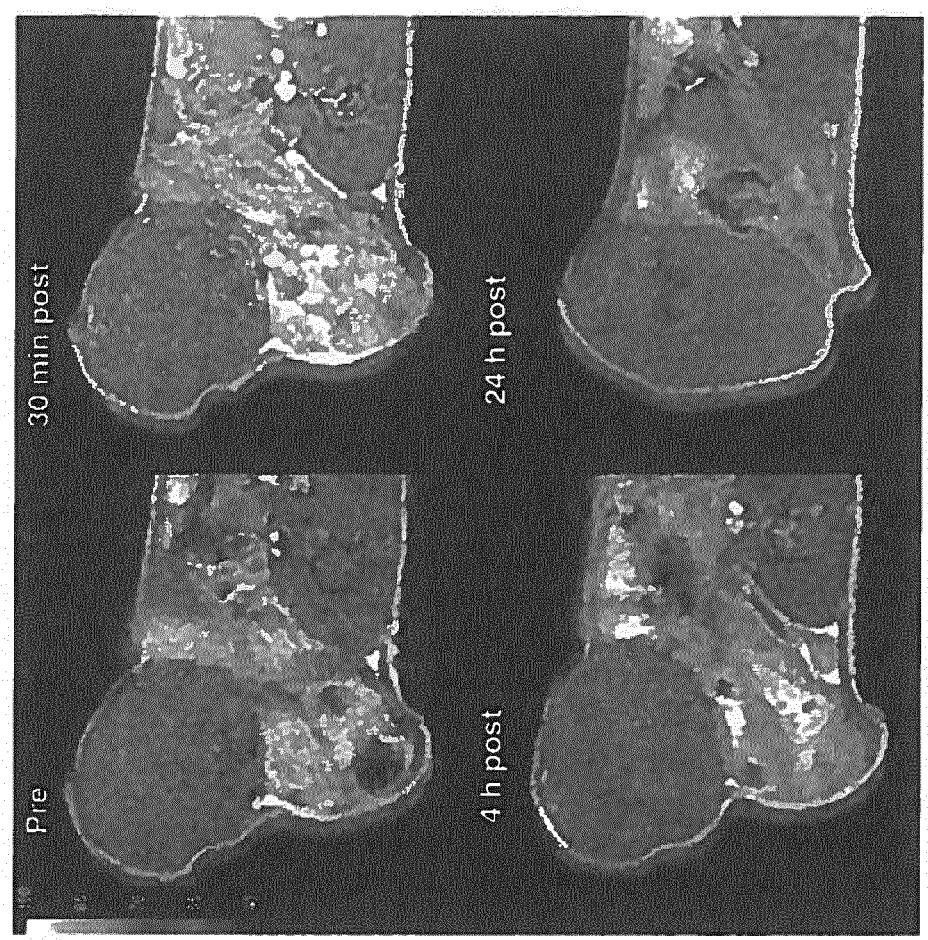
FIG. 3. U937 uptake of B22286 loaded SLNs, liposomes and Phohance®. The bars represent the Gd(III) mole/mg protein in U937 lysates after incubation with: B22286 loaded pSLNs and liposomes, and ProHance.

Results are shown in FIG. 3 where a lower uptake of the pSLNs as compared to liposomes by this monocytic-macrophage cell line has been observed.

Example 11. Biodistribution Studies of Paramagnetic Complexes of Formula (I) and (II) Incorporated in pSLNs The in vivo biodistribution of paramagnetic complexes of formula (I) and (II) incorporated into pSLNs, was studied in healthy C57BL/6 mice. pSLNs were administered to a n number of animals (wherein n is defined in Tables 7-8-9-10 for each study) at a dose of 50 μmol (Gd)/kg. Animals were sacrificed at different times following administration (see Tables 7-8-9-10). After sacrifice, the blood was stored in tubes containing a solution of sodium heparin (Clexane® 4000 IU/0.4 mL) in an approximately 1:100 (v/v) ratio with blood. After perfusion, liver, spleen and right kidney were excised and mineralized in nitric acid (65% w/v) using microwave mineralization (MDS-2000 CEM Corporation). Gd(III) content of was then measured by ICP-OES (OPTIMA 2100 DV Perkin Elmer) and reported in the studies as % ID calculated as described below:

% ID in an organ=(Gd micrograms in an organ/μg Gd administered dose)×100%

ID in blood=[(Gd micrograms/mL of blood)×(weight of the animal×72)/dose administered in μg Gd)× 100], wherein 72 corresponds to the blood volume in the mouse (mL/kg) pSLNs prepared as described in Example 8.1 were administered at doses described in the experimental scheme in Table 7 which also shows sampling times and sample number.

TABLE 7

Experimental scheme

| Dose (μmol/kg) | Sampling time | N. of animals treated for each sampling time |
|---|---|---|
| 10 | 30 s, 30 min, 60 min, 120 min, 180 min, 360 min, 24 h, 48 h, 72 h | 5 |
| | 1 month | 3 |
| 25 | 30 s, 30 min, 60 min, 120 min, 180 min, 360 min, 24 h, 48 h, 72 h | 5 |
| | 1 month | 3 |
| 50 | 30 s, 30 min, 60 min, 120 min, 180 min, 360 min, 24 h, 48 h, 72 h | 5 |
| | 1 month | 3 |

Biodistribution studies at 1 min, 6 h and 10 days after administration of 50 μmol/kg of Gd (III) complexes of formula (I) and formula (II) were repeated for various complexes prepared as described in the previous examples. Biodistribution values obtained for pSLNs prepared with different complexes at time points 1' (or immediately after administration), 6 hours, 10 (or 7) days after administration, are reported in tables 8-10 below.

TABLE 8

Biodistribution after administration (1') of pSLNs
containing amphiphilic complexes of formula (I) and (II).

| | % ID in blood | | | % ID in liver | | | % ID in spleen | | | % ID in kidney | | |
|---|---|---|---|---|---|---|---|---|---|---|---|---|
| | avg. | SD | n | avg. | SD | n | avg. | SD | n | avg. | SD | n |
| B22286 | 78 | 17 | 5 | 4.99 | 0.44 | 5 | 0.125 | 0.032 | 5 | 1.24 | 0.21 | 5 |
| 25a | 83.5 | 3.0 | 3 | 7.8 | 1.4 | 3 | 0.43 | 0.10 | 3 | 1.30 | 0.24 | 3 |
| 12d | 83.8 | 2.3 | 3 | 18.4 | 1.5 | 3 | 0.391 | 0.086 | 3 | 1.25 | 0.15 | 3 |
| 37a | 95.8 | 6.0 | 3 | 9.9 | 3.2 | 3 | 1.458 | 0.065 | 3 | 1.458 | 0.086 | 3 |
| 9c | 89.9 | 5.9 | 3 | 5.32 | 0.33 | 3 | 0.255 | 0.036 | 3 | 0.71 | 0.10 | 3 |
| 9b | 85.4 | 3.8 | 3 | 10.0 | 2.1 | 3 | 0.53 | 0.13 | 3 | 1.47 | 0.26 | 3 |

NQ (not quantifiable) <0.006%,
ND (not detectable) <0.002%

TABLE 9

Biodistribution at 6 h after administration of pSLNs
containing amphiphilic complexes of formula (I) and (II).

| | % ID in blood | | | % ID in liver | | | % ID in spleen | | | % ID in kidney | | |
|---|---|---|---|---|---|---|---|---|---|---|---|---|
| | avg. | SD | n | avg. | SD | n | avg. | SD | n | avg. | SD | n |
| B22286 | 4.32 | 0.12 | 2 | 76.7 | 3.5 | 3 | 0.582 | 0.049 | 5 | 0.61 | 0.100 | 5 |
| 25a | 3.1 | 1.8 | 4 | 35.4 | 7.7 | 4 | 1.17 | 0.66 | 4 | 0.31 | 0.130 | 4 |
| 12d | 2.3 | 1.6 | 3 | 27.0 | 15.0 | 3 | 0.63 | 0.46 | 3 | 0.164 | 0.043 | 3 |
| 37a | 4.80 | 0.10 | 3 | 14.7 | 2.6 | 3 | 0.57 | 0.11 | 3 | 0.463 | 0.069 | 3 |
| 9c | — | — | — | 39.0 | 6.9 | 3 | 1.58 | 0.25 | 3 | 0.283 | 0.086 | 3 |
| 9b | 1.74 | 0.14 | 3 | 57.9 | 1.5 | 3 | 0.542 | 0.046 | 3 | 0.470 | 0.018 | 3 |

NQ (not quantifiable) <0.006%,
ND (not detectable) <0.002%

TABLE 10

Biodistribution at 10 days after administration of
formulations containing amphiphilic complexes of formula (I) and (II).

| | % ID blood | | | % ID liver | | | % ID spleen | | | % ID kidney | | |
|---|---|---|---|---|---|---|---|---|---|---|---|---|
| | avg. | SD | n | avg. | SD | n | avg. | SD | n | avg. | SD | n |
| B22286 | 0.436 | 0.049 | 5 | 57.97 | 0.32 | 5 | 0.520 | 0.041 | 5 | 0.344 | 0.027 | 5 |
| 25a | — | — | — | 9.18 | 0.96 | 3 | 0.89 | 0.16 | 3 | NQ | — | 3 |
| 12d | — | — | — | 7.41 | 0.66 | 3 | 0.640 | 0.054 | 3 | ND | — | 3 |
| 37a | — | — | — | 6.53 | 0.59 | 3 | 0.517 | 0.016 | 3 | NQ | — | 3 |
| 9c | — | — | — | 12.28 | 0.97 | 3 | 1.08 | 0.59 | 3 | 0.06 | n/a | 1 |
| 9b | — | — | — | 8.95 | 0.18 | 3 | 0.379 | 0.017 | 3 | 0.106 | 0.0045 | 3 |

NQ (not quantifiable) <0.006%,
ND (not detectable) <0.002%

The results obtained, particularly at 10 days, indicate that, the accumulation of nanoparticles, and of gadolinium in liver and spleen, varies depending on the chain length and the nature of the amphiphilic complex, although with variable extents.

In particular for the preferred complexes, which are only exemplary embodiments of the complexes used in the invention, the accumulation in the liver of their corresponding pSLNs formulations, was always lower than for pSLNs with B22286, the Gd complex used as the model of an amphiphilic complexes with high liver accumulation due to a slow clearance from the hepatocytes. On the contrary the amount of Gd(III) ion accumulated in the spleen does not vary with respect to the chemical structure of the gadolinium complex upload in the pSLNs because the uptake of the phagocytic cells in the spleen is a process regulated by the surface properties of the nanoparticles that can be only slightly modified by the chemical structure of the uploaded gadolinium complex

The invention claimed is:

1. A paramagnetic Solid Lipid Nanoparticle (pSLN) comprising an inner solid lipid core and an amphiphilic component around said core, said amphiphilic component comprising a paramagnetic metal chelating moiety selected from the group consisting of a diazepine derivative of Formula I and salts thereof:

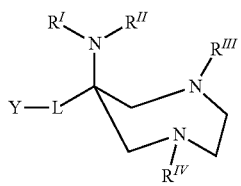

(I)

wherein:

Y is a group of formula Y'—NH— or (Y')$_2$—N—, where Y' is selected from the group consisting of:

a linear or branched saturated or unsaturated $C_8$-$C_{16}$ alkyl group; and a $C_1$-$C_{10}$ alkyl group interrupted by a phosphate group —O—(HO—P=O)—O— optionally substituted by one or more groups selected from: hydroxy —OH, carboxy —COOR$_1$, oxycarbonyl —($C_8$-$C_{16}$)alkyl and oxycarbonyl —($C_8$-$C_{16}$)alkenyl, where R$_1$ is hydrogen H or a $C_1$-$C_4$ linear or branched alkyl group; and a monophosphate ester of a substituted or partially substituted glycerol, having at least one functional group of said glycerol esterified with an aliphatic fatty acid with saturated or unsaturated carbon chains, and the phosphoric acid function is either free or salified with a alkali or earth alkali metal;

L is a bivalent linker selected from: an aliphatic $C_3$-$C_{10}$ cyclic or heterocyclic group and a $C_1$-$C_6$ alkyl, $C_2$-$C_6$ alkenyl or alkynyl, linear or branched group optionally substituted or interrupted with an atom or group selected from the group consisting of: carbonyl —C=O, thiocarbonyl —C=S, amino —NR$_1$—, carboxy —COO—, oxy-carbonyl —OCO—, amido —NR$_1$CO— or —CONR$_1$—, oxygen —O— and sulphur —S—, wherein R$_1$ is as defined above;

$R^{I\text{-}IV}$ and $R^{I\text{-}III}$ are each, independently a —($C_1$-$C_3$)alkylcarboxy group, wherein said chelating moiety is complexed with a paramagnetic metal ion selected from the group consisting of: Gd(III), Mn(II), Cr(III), Cu(II), Fe(III), Pr(III), Nd(III), Sm(III), Tb(III), Yb(III), Dy(III), Ho(III), Er(III), and a salt thereof.

2. The pSLN according to claim 1, wherein said solid lipid core comprises at least one glyceride selected from the group consisting of: a monoglyceride, a diglyceride, a triglyceride, and mixtures thereof, having a $C_{12}$-$C_{24}$ saturated or unsaturated linear or branched alkyl chain, where in the case of a di- and tri-glyceride, the alkyl chain can be the same or different, optionally further comprising a saturated or unsaturated fatty acid $C_{12}$-$C_{22}$, a fatty acid ester, or mixtures thereof.

3. The pSLN according to claim 2, wherein said glyceride is a triglyceride.

4. The pSLN according to claim 1, wherein said amphiphilic component further comprises at least one amphiphilic compound selected from the group consisting of: a $C_6$-$C_{24}$ linear or branched, saturated or unsaturated chain phospholipid, lysolipid and sphingolipid.

5. The pSLN of claim 1 comprising:

30-45% weight/weight of a lipid component, comprising at least one glyceride selected from the group consisting of: a monoglyceride, a diglyceride, a triglyceride, and mixtures thereof, having a $C_{12}$-$C_{24}$ saturated or unsaturated linear or branched alkyl chain, where in the case of a di- and tri-glyceride, the alkyl chain can be the same or different, optionally further comprising a saturated or unsaturated fatty acid $C_{12}$-$C_{22}$, a fatty acid ester, or mixtures thereof;

30-45% weight/weight of an amphiphilic component comprising a compound selected from the group consisting of: a $C_6$-$C_{24}$ linear or branched saturated or unsaturated chain phospholipid, a lysolipid, and a sphingolipid; and 4-10% weight/weight of the amphiphilic paramagnetic complex of Formula I or a salt thereof.

6. The pSLN according to claim 1, characterized by a relaxivity value $r_{1p}$ at 0.47 T higher than 25 mM$^{-1}$s$^{-1}$, measured in physiologic conditions.

7. The pSLN according to claim 1, having a particle distribution from 10 to 220 nm, an average hydrodynamic diameter below 100 nm and a polydispersity index (PdI) below 0.2.

8. The pSLN according to claim 7, wherein said average diameter is from 50-70 nm and the PdI is comprised from 0.12-0.18.

9. The pSLN according to claim 4, wherein the amphiphilic component comprises an amphiphilic compound which comprises a $C_6$-$C_{24}$ linear or branched, saturated or unsaturated chain phospholipid selected from the group consisting of: phosphatidylcholine, phosphatidylserine, phosphatidylethanolamine, phosphatidyl-inositol and mixtures thereof, optionally further comprising: a bile acid or a salt thereof, a glycolipid, a fatty acid, an aliphatic alcohol, a dialkyl ether or tocopherol.

10. The pSLN according to claim 9, wherein said phospholipid is of natural origin and is derived from soy or egg lecithin.

11. The pSLN according to claim 10, further comprising at least one component selected from the group consisting of: a) at least one of an ionic or a non-ionic surfactant; b) a "stealth" agent optionally chemically modified with a suitable specific ligand and/or an alkyl chain or an amphiphilic component; and c) an endogenous biomolecule optionally chemically modified, wherein said specific ligand or said endogenous biomolecule is selected from the group consisting of: vitamins, peptides and polypeptides.

12. The pSLN according to claim 1, wherein the amphiphilic paramagnetic complex is selected from the group consisting of the following compounds or salts thereof:

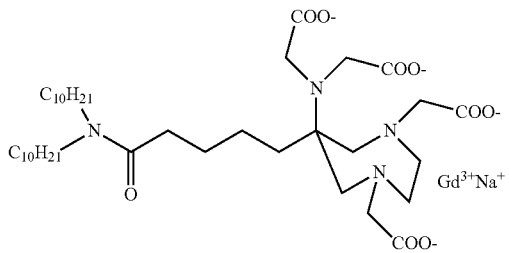

12d

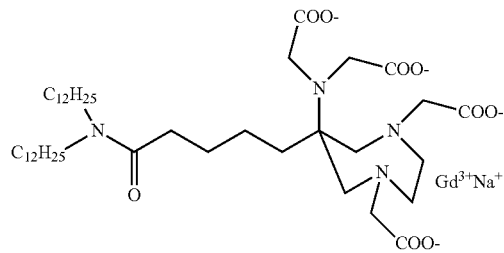

12e

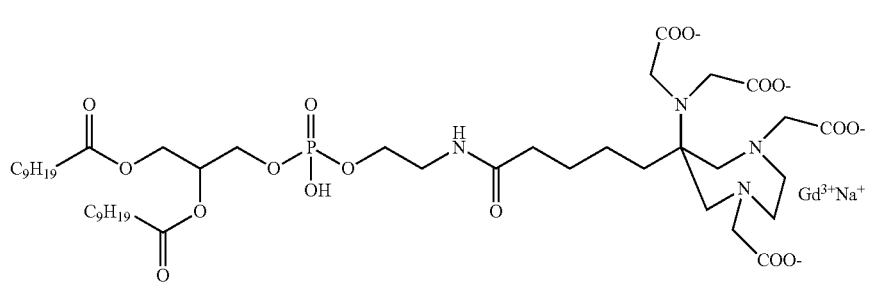
9a
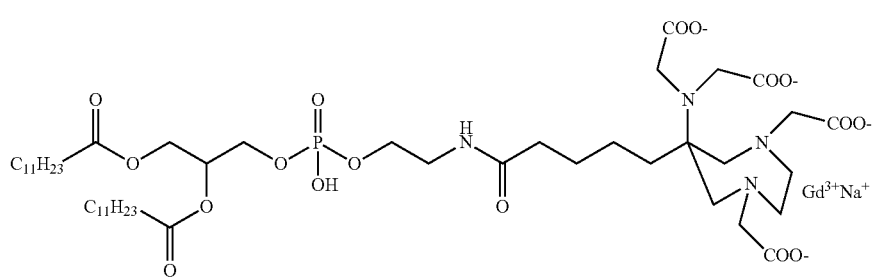
9b
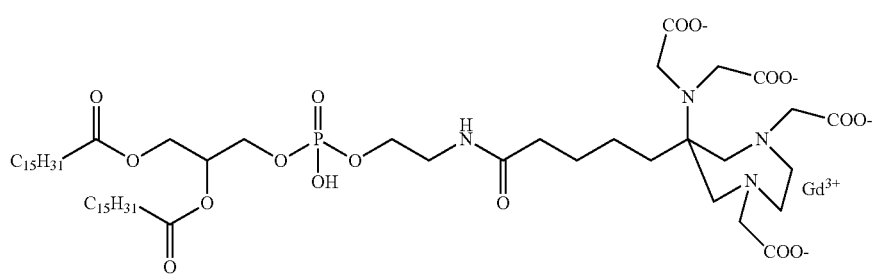
9c
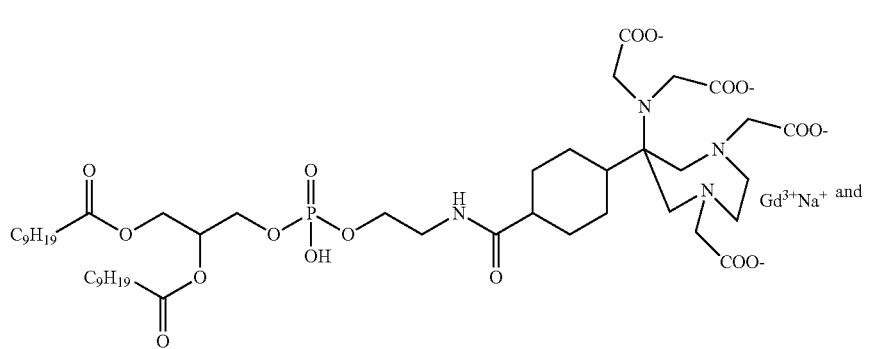
25c
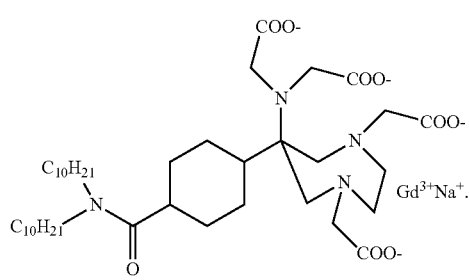
25a

13. The pSLN according to claim 11, wherein the "stealth agent" is polyethyleneglycol (PEG) optionally chemically modified with a phospholipid, a folate or a phospholipid and a folate.

14. A process for the preparation of the paramagnetic Solid Lipid Nanoparticle (pSLN) of claim 1, comprising the following steps:
a) preparing an organic phase (O) by admixing, in a low boiling solvent immiscible in water at least the following components:
an amphiphilic complex suitable for chelating metal ions selected from a diazepine derivative of Formula I and salts thereof:

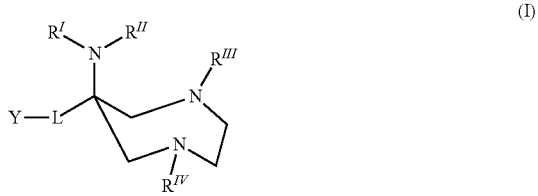

(I)

wherein:
Y is a group of formula Y'—NH— or (Y')$_2$—N—, where Y' is selected in from the group consisting of:
a linear or branched saturated or unsaturated $C_8$-$C_{16}$ alkyl group; and a $C_1$-$C_{10}$ alkyl group interrupted by a phosphate group —O—(HO—P=O)—O— optionally substituted by one or more groups selected from: hydroxy —OH, carboxy —COOR$_1$, oxycarbonyl —($C_8$-$C_{16}$)alkyl and oxycarbonyl —($C_8$-$C_{16}$)alkenyl, where R, is hydrogen H or a $C_1$-$C_4$ linear or branched alkyl group; and
a monophosphate ester of a substituted or partially substituted glycerol, having at least one functional group of said glycerol esterified with an aliphatic fatty acid with saturated or unsaturated carbon chains, and the phosphoric acid function is either free or salified with a alkali or earth alkali metal;
L is a bivalent linker selected from: an aliphatic $C_3$-$C_{10}$ cyclic or heterocyclic group and a $C_1$-$C_6$ alkyl, $C_2$-$C_6$ alkenyl or alkynyl, linear or branched group optionally substituted or interrupted with an atom or group selected from the group consisting of: carbonyl —C=O, thiocarbonyl —C=S, amino —NR$_1$—, carboxy —COO—, oxy-carbonyl —OCO—, amido —NR$_1$CO— or —CONR$_1$—, oxygen —O— and sulphur —S—, wherein R$_1$ is as defined above;
R$^{I-IV}$ and R$^{I-III}$ are each, independently a —($C_1$-$C_3$)alkylcarboxy group,
wherein said chelating moiety is complexed with a paramagnetic metal ion selected from the group consisting of: Gd(III), Mn(II), Cr(III), Cu(III), Fe(III), Pr(III), Nd(III), Sm(III), Tb(III), Yb(III), Dy(III), Ho(III) and Er(III);
a lipid wherein said lipid is a glyceride selected from the group consisting of: a monoglyceride, a diglyceride, a triglyceride and mixtures thereof, having a $C_{12}$-$C_{24}$ saturated or unsaturated linear and branched alkyl chain, where in the case of a di- and triglyceride the alkyl chain can be the same or different, optionally further comprising a saturated or unsaturated fatty acid $C_{12}$-$C_{22}$, a fatty acid ester, and mixtures thereof;
an amphiphilic surfactant selected from the group consisting of: a $C_6$-$C_{24}$ linear or branched saturated or unsaturated chain phospholipid, lysolipid, or sphingolipid, optionally further comprising: a bile acid or a salt thereof, a glycolipid, a fatty acid, an aliphatic alcohol, a dialkyl ether and tocopherol;
b) preparing an aqueous solution (W) comprising one or more of a ionic or non ionic surfactant and optionally a co-surfactant selected in the group consisting of: a $C_3$-$C_8$ poli-alkyl alcohol, and a fat saturated $C_5$-$C_{12}$ acid;
c) mixing the organic phase (0) prepared in a) with the aqueous solution (W) prepared in b), to obtain a micro-emulsion (W/O) stable and transparent at a temperature from 20° C. to 40° C.;
d) adding the micro-emulsion (W/O) according to step c) to a second aqueous solution (W$_1$) comprising at least a non-ionic or ionic tensioactive substance at a temperature from 20° C. to 40° C. to obtain a multiple emulsion (W/O/W$_1$);
e) evaporating the organic solvent from the multiple emulsion and obtaining a suspension of lipid nanoparticles; and
f) cooling the suspension obtained at step e) to a temperature lower than the crystallization point of the lipid component as defined in step a) to obtain pSLNs.

15. The process according to claim 14, wherein the lipid in step a) is a triglyceride and is selected from the group consisting of: tri-myristin, tri-palmitin, tri-stearin, triarachidin and mixtures thereof.

16. The process according to claim 14, wherein the immiscibile organic solvent in step a) is selected from the group consisting of: methylene chloride, diethyl-ether, ethyl acetate, ethyl formiate, 1,2 di-chloroethane, and mixtures thereof.

17. The process according to claim 16, wherein the solvent is methylene chloride.

18. The process according to claim 14, wherein the organic phase (O) in step a) is warmed to a temperature from 25° C. to 40° C.

19. The process according to claim 14, wherein the fatty acid in the lipid component in step a) is selected from the group consisting of: myristic acid, palmitic acid, stearic acid, and behenic acid.

20. The process according to claim 14, wherein the lipid component in a) comprises tripalmitin and stearic acid.

21. The process according to claim 14, wherein the amphiphilic surfactant in step a) comprises a phospholipid selected from the group consisting of: phosphatidyl choline, phosphatidyl serine, phosphatidyl ethanolamine, phosphatidyl inositol and their mixture, or is soy or egg lecithin.

22. The process according to claim 14, wherein the aqueous solution (W) as defined in step b) further comprises a low molecular weight ionic surfactant.

23. The process according to claim 14, wherein the organic phase (O) as defined in step a) or the aqueous solution (W) as defined in step b) further comprises at least one additional component selected from the group consisting of: a "stealth" agent optionally chemically modified with a suitable specific ligand and/or an alkyl chain or an amphiphilic component and an endogenous biomolecule optionally chemically modified, wherein said specific ligand or said endogenous biomolecule is selected from the group consisting of: vitamins, peptides and polypeptides.

24. The process according to claim 14, further comprising the following steps:
g) purification of the pSLN suspension; and
h) sterilization.

25. A pharmaceutical composition, comprising the pSLN according to claim 1.

26. The pSLN according to claim 3, wherein said triglyceride is selected from the group consisting of: trimyristin, tripalmitin, tristearin, triarachidin and mixtures thereof.

* * * * *